United States Patent
Adam et al.

Patent Number: 6,075,034
Date of Patent: Jun. 13, 2000

[54] SPIRO[PIPERIDINE-4,1'-PYRROLO [3,4-C] PYRROLE]DERIVATIVES

[75] Inventors: Geo Adam, Schopfheim; Frank Dautzenberg, Müllheim; Sabine Kolczewski, Lörrach; Stephan Röver, Inzlingen; Jürgen Wichmann, Steinen, all of Germany

[73] Assignee: Hoffmann-La Roche Inc., Nutley, N.J.

[21] Appl. No.: 09/330,857

[22] Filed: Jun. 11, 1999

[30] Foreign Application Priority Data

Jun. 12, 1998 [EP] European Pat. Off. ............ 98110803
Dec. 18, 1998 [EP] European Pat. Off. ............ 98124119

[51] Int. Cl.[7] ................... A01N 43/42; C07D 487/20
[52] U.S. Cl. ............................ 514/278; 546/17
[58] Field of Search ............................ 546/17; 514/278

[56] References Cited

PUBLICATIONS

Julius, *Nature* 377:476 (1995).
Meunier, *Eur. J. Pharmacol.*, 340:1–15 (1997).
Henderson et al., *Trends Pharmacol. Sci.*, 18:293–300 (1997).
Mogil et al., *Neuroscience*, 75:333–337 (1996).
Vanderah et al., *Eur. J. Pain*, 2:267–280 (1998).
Jenck et al., *Proc. Natl. Acad. Sci., USA*, 94:14854–14858 (1997).
Billington et al., *Neuroreport*, 8:369–371 (1996).
Manabe et al., *Nature*, 394:577–581 (1998).
Peluso et al., *J. Neuroimmmuno*, 81:184–192 (1998).
Döpp et al., *Chem. Ber.* 121:1651–1655 (1988).
Tsuge et al., *Chem. Lett.*, pp. 973–976 (1986).
Bunzow et al., *Febs Lett.* 347:284–288 (1994).
Cheng et al., *Biochem. Pharmacol.*, 22:3099–3108 (1973).

*Primary Examiner*—Fiona T. Powers
*Attorney, Agent, or Firm*—George W. Johnston; Dennis P. Tramaloni; Joseph P. Kirk, Jr.

[57] ABSTRACT

The present invention relates to compounds of the general formula

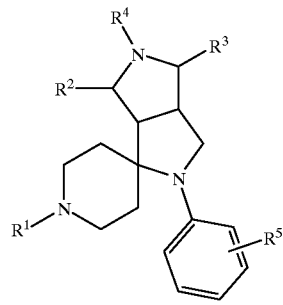

wherein $R^1$ is $C_{5-12}$-cycloalkyl, optionally substituted by lower alkyl; decahydro-naphthalen-1-yl; decahydro-naphthalen-2-yl; indan-1-yl or indan-2-yl, optionally substituted by lower alkyl; decahydro-azulen-2-yl; bicyclo[6.2.0]dec-9-yl; acenaphthen-1-yl; bicyclo[3.3.1]non-9-yl; 2,3-dihydro-1H-phenalen-1-yl; 2,3,3a,4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;

$R^2$, $R^3$ are hydrogen; hydroxy; lower alkyl; =O; or phenyl, optionally substituted by lower allyl, halogen or alkoxy;

$R^4$ is hydrogen; lower alkyl; —$(CH_2)_n$CH(OH)CF$_3$; —$(CH_2)_nC_{3-6}$-cycloalkyl; phenyl; benzyl; tetrahydrofuran-3-yl; —$(CH_2)_n$OCH$_2$C$_6$H$_5$; —$(CH_2)_n$morpholinyl; 3-methyl-oxetan-3-yl-methyl; —$(CH_2)_n$CH$_2$OH; —S(O)$_2$-lower alkyl; —C(O)-lower alkyl; —C(O)CF$_3$; —C(O)(CH$_2$)$_n$OCH$_3$; —$(CH_2)_n$C(O)N(lower alkyl)$_2$; —S(O)$_2$heteroaryl; —C(O)heteroaryl; —S(O)$_2$-phenyl; —S(O)$_2$—N(lower alkyl)$_2$; —C(O)—C$_{3-6}$-cycloalkyl; —C(O)O-phenyl; or —C(O)O-lower alkyl;

$R^5$ is hydrogen; halogen; lower alkyl; trifluoromethyl or lower alkoxy;

n is 0–3;

and to pharmaceutically acceptable acid addition salts thereof

The compounds of formula I and their salts are useful as in the treatment of psychiatric, neurological and physiological disorders.

53 Claims, No Drawings

SPIRO[PIPERIDINE-4,1'-PYRROLO [3,4-C] PYRROLE]DERIVATIVES

FIELD OF THE INVENTION

This invention relates to spiro[piperidine-4,1'-pyrrolo[3, 4-c]pyrrole derivatives particularly wherein $R^1$ is $C_{5-12}$-cycloalkyl which may be substituted or unsubstituted or wherein $R^1$ is decahydro-napthalen-2-yl and compositions and uses therof.

BACKGROUND

OFQ, a heptadeca peptide, has been isolated from rat brain and is a natural ligand to a G-protein coupled receptor (OFQ-R), found at high levels in brain tissue. OFQ exhibits agonistic activity at the OFQ-R both in vitro and in vivo.

Julius (Nature 377,476, [1995]) discusses the discovery of OFQ noting that this peptide shares greatest sequence homology with dynorphin A, an established endogenous ligand for opioid receptors. OFQ inhibits adenylate cyclase in CHO(LC 132$^+$) cells in culture and induces hyperalgesia when administered intra-cerebroventricularly to mice. The pattern of results indicate that this heptadecapeptide is an endogenous agonist of the LC 132 receptor and it appears to have pro-nociceptive properties. It has been described that when injected intra-cerebroventricularly in mice, OFQ slowes down locomotive activity and induces hyperalgesia and it has been concluded that OFQ may act as a brain neurotransmitter to modulate nociceptive and locomotive behavior.

In the following references these indications have been described:

Nociceptin/orphanin FQ and the opioid receptor-like ORL1 receptor, Eur. J. Pharmacol., 340: 1–15, 1997;

The orphan opioid receptor and its endogenous ligand nociceptin/orphanin FQ, Trends Pharmacol. Sci., 18:293–300, 1997;

Orphanin FQ is a functional anti-opioid peptide, Neuroscience, 75:333–337, 1996;

Orphanin FQ/nociceptin-lack of antinociceptive, hyperalgesic or allodynic effects in acute thermal or mechanical tests, following intracerebroventricular or intrathecal administration to mice or rats, Eur. J. pain, 2: 267–280, 1998;

Orphanin FQ acts as an anxiolytic to attenuate behavioral responses to stress, Proc. Natl. Acad. Sci., USA, 94: 14854–14858, 1997;

Orphanin FQ, an agonist of orphan opioid receptor ORL1, stimulates feeding in rats, Neuroreport, 8: 369–371, 1996;

Facilitation of long-term potentiation and memory in mice lacking nociceptin receptors, Nature, 394: 577–581, 1998;

Distribution of nociceptin/orphanin FQ receptor transcript in human central nervous system and immune cells, J. Neuroimmuno, 81: 184–192, 1998.

The compounds of the present invention intereact with the OFQ receptor and objects of the present invention are the compounds of formula I and pharmaceutically acceptable addition salts thereof, racemic mixtures and their corresponding enantiomers, the preparation of the above-mentioned compounds, medicaments containing them and their manufacture as well as the use of the above-mentioned compounds in the control or prevention of illnesses, especially of illnesses and disorders of the kind referred above, or in the manufacture of corresponding medicaments.

SUMMARY OF THE INVENTION

The present invention relates to compounds of the general formula

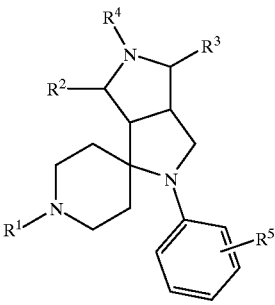

I wherein
  $R^1$ is $C_{5-12}$-cycloalkyl, optionally substituted by lower alkyl; decahydro-naphthalen-1-yl; decahydro-naphthalen-2-yl; indan-1-yl or indan-2-yl, optionally substituted by lower alkyl; decaydro-azulen-2-yl; bicyclo[6.2.0]dec-9-yl; acenaphthen-1-yl; bicyclo [3.3.1]non-9-yl; 2,3-dihydro-1H-phenalen-1-yl; 2,3,3a, 4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;
  $R^2$, $R^3$ are hydrogen; hydroxy; lower alkyl; =O; or phenyl, optionally substituted by lower alkyl, halogen or alkoxy;
  $R^4$ is hydrogen; lower akyl; —$(CH_2)_n$CH(OH)CF$_3$; —$(CH_2)_nC_{3-6}$-cycloalkyl; phenyl; benzyl; tetrahydrofuran-3-yl; —$(CH_2)_n$OCH$_2$C$_6$H$_5$; —$(CH_2)_n$ morpholinyl; 3-methyl-oxetan-3-yl-methyl; —$(CH_2)_n$ CH$_2$OH; —S(O)$_2$-lower alkyl; —C(O)-lower alkyl; —C(O)CF$_3$; —C(O)(CH$_2$)$_n$OCH$_3$; —$(CH_2)_n$C(O)N (lower alkyl)$_2$; —S(O)$_2$heteroaryl; —C(O)heteroaryl; —S(O)$_2$-phenyl; —S(O)$_2$—N(lower alkyl)$_2$; —C(O)-C$_{3-6}$-cycloalkyl; —C(O)O-phenyl; or —C(O)O-lower alkyl:
  $R^5$ is hydrogen; halogen; lower alkyl; trifluoromethyl or lower alkoxy;
  n is 0–3;
and to pharmaceutically acceptable acid addition salts thereof.

The compounds of formula I and their salts are characterized by valuable therapeutic properties. It has surprisingly been found that the compounds of the present invention are agonists of the orphanin FQ (OFQ) receptor. Consequently they are useful in the treatment of psychiatric, neurological and physiological disorders, especially, but not limited to, amelioration of symptoms of anxiety and stress disorders, depression, trauma, memory loss due to Alzheimer's disease or other dementias, deficits in cognition and learning, epilepsy and convulsions, acute and/or chronic pain conditions, symptoms of addictive drug withdrawal, control of water balance, Na$^+$ excretion, arterial blood pressure disorders and metabolic disorders such as obesity.

DETAILED DESCRIPTION OF THE INVENTION

The following definitions of the general terms used in the present description apply irrespective of whether the terms in question appear alone or in combination, such as lower alkyl and lower alkoxy.

The term "lower alkyl" denotes a straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "cycloalkyl" denotes a saturated carbocyclic group containing from 5–12 carbon atoms, preferred are cyclohexyl, cyclooctyl, cyclononyl and cyclodecyl.

The term "heteroaryl" includes an aromatic 5–6 membered ring, containing one to four heteroatoms selected from oxygen, sulfur and nitrogen. Examples of heteroaryl are furyl, thiophenyl, oxazolyl, isoxazolyl, thiazolyl, isothiazolyl, imidazolyl, triazolyl, pyrrazolyl, pyridinyl and pyrimidinyl.

The term "halogen" denotes chlorine, iodine, fluorine and bromine.

The term "pharmaceutically acceptable acid addition salts" embraces salts with inorganic and organic acids well-known in the art for pharmaceutic purposes, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present invention are those of formula I, in which $R^1$ is $C_{5-12}$-cycloalkyl, optionally substituted by lower alkyl, for example the following compounds:

(3'aRS,6'aSR)-1-Cyclononyl-5'-methyl-2'-phenyl-hexahydro-spiro[piperidine-4,1'(2'H)-pyrrolo[3,4-c]pyrrole];
(3'aRS,6'aSR)-1-Cyclodecyl-5'-methyl-2'-phenyl-hexahydro-spiro[piperidine-4,1'(2H)-pyrrolo[3,4-c]pyrrole]-4',6'-dione;
(3'aRS,6'aSR)-1-Cyclodecyl-5'-ethyl-2'-phenyl-hexahydro-spiro[piperidine-4,1'(2'H)-pyrrolo[3,4-c]pyrrole];
(3'aRS,6'aSR)1-(cis-4-Isopropyl-cyclohexyl)-5'-methyl-2'-phenyl-hexahydro-spiro[piperidine-4,1'-pyrrolo[3,4-c]pyrrole];
(3'aRS,6'aSR)1-(cis-4-Isopropyl-cyclohexyl)-5'-ethyl-2'-phenyl-hexahydro-spiro[piperidine-4,1'-pyrrolo[3,4-c]pyrrole];
(3'aRS,6'aSR)-4-(cis-4-Isopropyl-cyclohexyl)-5'-butyl-2'-phenyl-hexahydro-spiro[piperidine-4,1'(2'H)-pyrrolo[3,4-c]pyrrole];
(3'aRS,6'aSR)-4-(cis-4-Isopropyl-cyclohexyl)-5'-cyclopropylmethyl-2'-phenyl-hexahydro-spiro[piperidine-4,1'(2'H)-pyrrolo[3,4-c]pyrrole];
(3'aRS,4'SR,6'aRS)-1-(cis-4-Isopropyl-cyclohexyl)-4',5'-dimethyl-2'-phenyl-hexahydro-spiro[piperidine-4,1'-pyrrolo[3,4-c]pyrrole];
(3'aRS,6'aSR)-4-(cis-4-Isopropyl-cyclohexyl)-2'-phenyl-hexahydro-spiro[piperidine-4,1'(2'H)-pyrrolo[3,4-c]pyrrole];
(3'aRS,6'aSR)-1-Cyclodecyl-5'-methyl-2'-phenyl-hexahydro-spiro[piperidine-10 4,1'(2'H)-pyrrolo[3,4-c]pyrrole];
(3'aRS,6'aSR)-1-Cyclononyl-5'-ethyl-2'-phenyl-hexahydro-spiro[piperidine-4,1'(2'H)-pyrrolo[3,4-c]pyrrole];
(3'aRS,6'aSR)-1-(cis-4-Isopropyl-cyclohexyl)-5'-methyl-2'-phenyl-hexahydro-spiro[piperidine-4,1'-pyrrolo[3,4-c]pyrrole]-4',6'-dione;
(3'aRS,6'aSR)-1-(cis-4-Isopropyl-cyclohexyl)-5'-benzyl-2'-phenyl-hexahydro-spiro[piperidine-4,1'-pyrrolo[3,4-c]pyrrole]-4',6'-dione;
(3'aRS,6'aSR)-4-(cis-4-Isopropyl-cyclohexyl)-5'-benzyl-2'-phenyl-hexahydro-spiro[piperidine-4,1'(2'H)-pyrrolo[3,4-c]pyrrole];
(3'aRS,6'aSR)-4-(cis-4-Isopropyl-cyclohexyl)-5'-cyclohexyl-2'-phenyl-hexahydro-spiro[piperidine-4,1'(2'H)-pyrrolo[3,4-c]pyrrole];
(3'aS,6'aR)1-(cis-4-Isopropyl-cyclohexyl)-5'-methyl-2'-phenyl-hexahydro-spiro[piperidine-4,1'-pyrrolo[3,4-c]pyrrole];
(3'aR,6'aS)1-(cis-4-Isopropyl-cyclohexyl)-5'-methyl-2'-phenyl-hexahydro-spiro[piperidine-4,1'-pyrrolo[3,4-c]pyrrole];
(3aRS,6'aRS)-1-(cis-4-Isopropyl-cyclohexyl)-5'-(2-hydroxy-ethyl)-2'-phenyl-hexahydro-spiro[piperidine-4,1'-pyrrolo[3,4-c]pyrrole];
(3'aRS,6'aSR)-2-[1-(cis-4-Isopropyl-cyclohexyl)-2'-phenyl-hexahydro-spiro[piperidine-4,1'-pyrrolo[3,4-c]pyrrol]-5'-yl]-N,N-dimethyl-acetamide;
(3'aRS,6'aRS)-[1-(cis-4-Isopropyl-cyclohexyl)-2'-phenyl-hexahydro-spiro[piperidine-4,1'-pyrrolo[3,4-c]pyrrol]-5'-yl]-pyridin-3-yl-methanone; (3'aRS,6'aSR)-2'-(3-Fluoro-phenyl)-1-(cis-4-isopropyl-cyclohexyl)-5'-methyl-hexahydro-spiro[piperidine-4,1'-pyrrolo[3,4-c]pyrrole]-4',6'-dione;
(3'aS,6'aR)-1-Cyclononyl-5'-methyl-2'-phenyl-hexahydro-spiro[piperidine-4,1'-pyrrolo[3,4-c]pyrrole];
(3'aS,6'aR)-1-Cyclodecyl-2'-(2-fluoro-phenyl)-5'-methyl-hexahydro-spiro[piperidine-4,1'-pyrrolo[3,4-c]pyrrole];
(3'aRS,6'aSR)-1-Cyclononyl-2'-(4-fluoro-phenyl)-5'-methyl-hexahydro-spiro[piperidine-4,1'-pyrrolo[3,4-c]pyrrole];
(3'aRS,6'aSR)-1-Cylouononyl-2'-phenyl-hexahydro-spiro[piperidine-4,1'-pyrrolo[3,4-c]pyrrole];
(3'aRS,6'aSR)-(1-Cyclononyl-2'-phenyl-hexahydro-spiro[piperine-4,1'-pyrrolo[3,4-c]pyrrol]-5'-yl)-cyclopropyl-methanone; and
(3'aRS,6'aSR)-(1-Cyclodecyl-2'-phenyl-hexahydro-spiro[piperine-4,1'-pyrrolo[3,4-c]pyrrol]-5'-yl)-cyclopropyl-methanone;
(3'aRS,6'aRS)-1-(cis-4-Isopropyl-cyclohexyl)-2'-phenyl-hexahydro-spiro[piperidine-4,1'-pyrrolo[3,4-c]pyrrol]-5'-yl]-thiophen-2-yl-methanone Further preferred are compounds of formula I, in which $R^1$ is decahydro-naphthalen-2-yl.

Examples of such compounds are

Mixture of (3'aSR,6'aRS)- and (3'aRS,6'aSR)-1-[(2RS,4aSR,8aRS)-decahydro-naphthalen-2-yl]-5'-methyl-2'-phenyl-hexahydro-spiro[piperidine-4,1'-pyrrolo[3,4-c]pyrrole];

Mixture of (3'aSR,6'aRS)- and (3'aRS,6'aSR)-1-[(2RS,4aSR,8aRS)-decahydro-naphthalen-2-yl]-2'-phenyl-hexahydro-spiro[piperidine-4,1'-pyrrolo[3,4-c]pyrrole];

Mixture of (3'aSR,6'aRS)- and (3'aRS,6'aSR)-5'-ethyl-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione;

Mixture of (3'aSR,6'aRS)- and (3'aRS,6'aSR)-5'-methyl-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione;

Mixture of (3'aSR,6'aRS)- and (3'aRS,6'aSR)-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione; and Mixture of (3'aSR,6'aRS)- and (3'aRS,6'aSR)-5'-ethyl-1-[(2RS,4aSR,8aRS)-decahydro-naphthalen-2-yl]-2'-phenyl-hexahydro-spiro[piperidine-4,1'-pyrrolo[3,4-c]pyrrole].

Other preferred compounds of formula I are, for example

Mixture of (3'aRS,6'aSR)- and (3'aSR,6'aRS)-5'-methyl-1-[(RS)-4-methyl-indan-2-yl]-2'-phenyl-hexahydro-spiro[piperidine-4,1'-pyrrolo[3,4-c]pyrrole];

Mixture of (3'aRS,6'aSR)- and (3'aSR,6'aRS)-1-[(RS)-4-methyl-indan-2-yl]-2'-phenyl-hexahydro-spiro[piperidine-4,1'-pyrrolo[3,4-c]pyrrole];

(3'aS,6'aR)-5'-Ethyl-2'-phenyl-1-[(R)-1,2,3,4-tetrahydro-naphtalen 1-yl]-hexahydro-spiro[piperidine-4,1'-pyrrolo[3,4-c]pyrrole];

(3'aS,6'aR)-5'-Methyl-2'-phenyl-1-[(R)-1,2,3,4-tetrahydro-naphtaten-1-yl]-hexahydro-spiro[piperidine-4,1'-pyrrolo[3,4-c]pyrrole];

(3'aSR,6'aRS)-1-[(RS)-Acenaphthen-1-yl]-5'-methyl-1'-phenyl-hexahydro-spiro[piperidine-4,1'(2'H)-pyrrolo[3,4-c]pyrrole];

(3'aRS,6'aSR)-1-[(1RS,3aRS)-2,3,3a,4,5,6-Hexahydro-1H-phenalen-1-yl]-5'-methyl-2'-phenyl-hexahydro-spiro[piperidine-4,1'(2'H)-pyrrolo[3,4-c]pyrrole]; and Mixture of (3'aRS,6'aSR)- and (3'aSR,6'aRS)-1-[(RS)-2,3-dihydro-1H-phenalen-1-yl]-5'-methyl-2'-phenyl-hexahydro-spiro[piperidine-4,1'(2'H)-pyrrolo[3,4-c]pyrrole.

The present compounds of formula I and their pharmaceutically acceptable salts can be prepared by methods known in the art, for example, by the processes described below, which comprise a) reductively aminating a compound of formula

II with a compound of formula

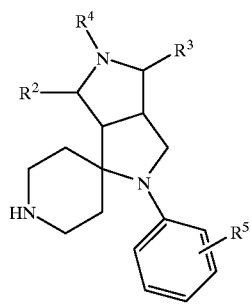

III wherein $R^1$–$R^5$ have the significances given above, or b) reducing a compound of formula

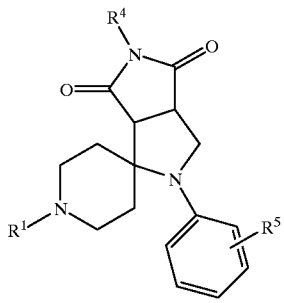

I-1 to a compound of one of the formulae

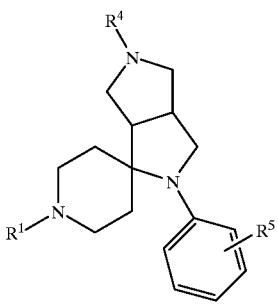

I-2

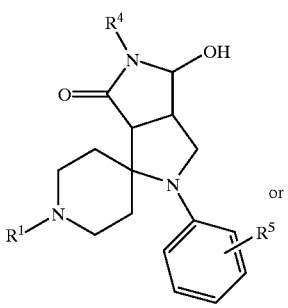

I-3 or

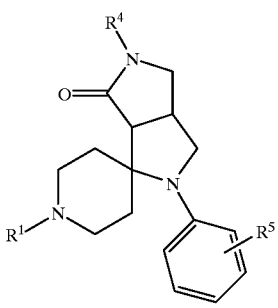

I-4 wherein $R^1$, $R^4$ and $R^5$ have the significances given above, or c) acylating or sulfonylating a compound of formula

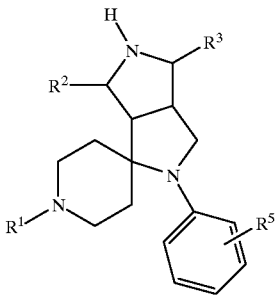
I-5 to a compound of formula

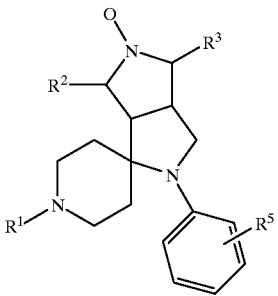
I-6 wherein R¹–R³ and R⁵ have the significances given above and Q is —S(O)₂-lower alkyl; —C(O)-lower alkyl; —C(O)CF₃; —C(O)(CH₂)$_n$OCH₃; —C(O)N (lower alkyl)₂; —S(O)₂-heteroaryl; —C(O)-heteroaryl; —S(O)₂-phenyl; —C(O)-C$_{3-6}$-cycloalkyl; or —C(O)O-lower alkyl and n is 0–3, or d) debenzylating a compound of formula

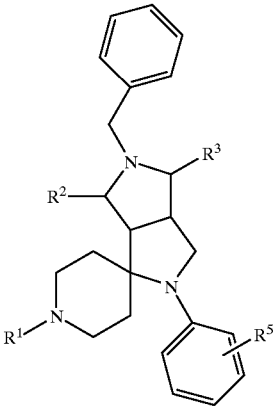
I-7 to a compound of formula

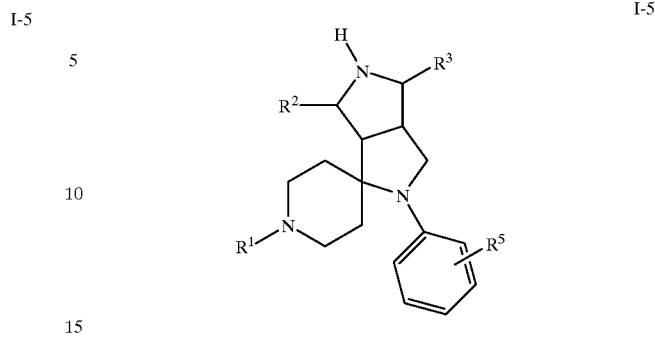
I-5 wherein R¹–R³ and R⁵ have the significances given above, except that R² and R³ are not =O or hydoxy, e) reacting a ketone of formula

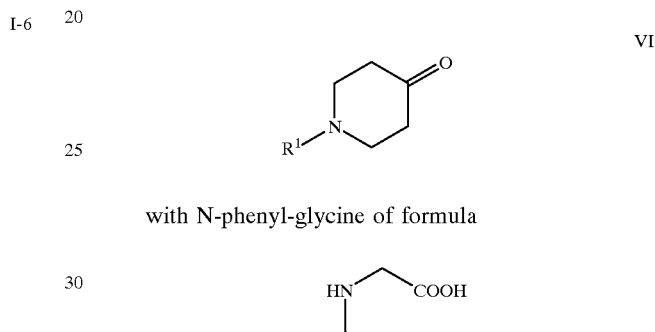
VI with N-phenyl-glycine of formula

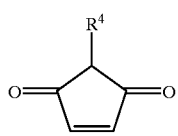

and trapping the forming azomethine-ylides of formula

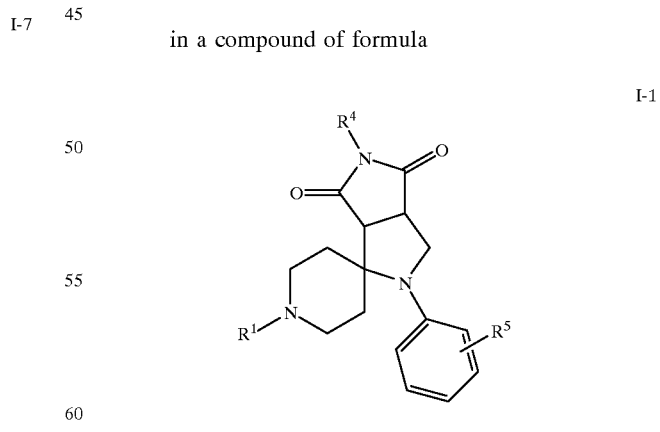
I-1 wherein the substituents have the significances given above, or, if desired, converting a racemic mixture into its enantiomeric components thus obtaining optically pure compounds, and converting a compound of formula I obtained into a pharmaceutically acceptable acid addition salt.

In accordance with process variant a) the reductive amination of a keto compound of formula II with an amine of formula III is carried out by stirring with a dehydrating agent in the presence of molecular sieves (4 Å), in an inert solvent, such as toluene or tetrahydrofuran (THF), at reflux temperature. An alternative method is the dehydration in the presence of an acidic catalyst with removal of water, e.g. with azeotropic removal of water, or with tetraisopropylorthotitanate in THF.

The obtained intermediate enamine or imine is then reduced with a reducing agent, such as metal hydrides or hydrogen in the presence of a hydrogenating catalyst, preferably with sodium cyanoborohydride in a protic solvent, for example in a mixture of THF and ethanol at acidic pH.

Examples for corresponding keto compounds of formula II are the following:

2-indanone, bicyclo[6.2.0]dec-9-one or $C_{5-12}$-cycloalkanone, optionally substituted by lower alkyl.

In accordance with process variant b) a compound of formula I-1 is reduced to one of the compounds of formulae I-2. I-3 and I-4. This process is carried out in conventional manner with a reducing agent, preferably a metal hydride, such as lithium aluminium hydride or sodium borohydride in an aprotic solvent, for example in diethylether, tetrahydrofuran or dichloromethane.

In accordance with process variant c) a compound of formula I-5 is acylated or sulfonylated with a corresponding acid chloride, acid anhydride, sulfonyl chloride, carbamoyl chloride or carbonyl chloride in the presence of triethylamine in a solvent, such as dichloromethane. This reaction is carried out in conventional manner.

The process for preparation of a compound of formula I-5 in accordance with process variant d) is carried out in conventional manner with catalytic amounts of 10% Pd/C with hydrogen at 1 atm in methanol and acetic acid, preferrably in a ratio of 10:1.

The process according to variant e) is carried out by reacting a ketone with a slight excess of N-phenyl-glycine in an inert solvent like for example toluene at elevated temperatures in the presence of a base, such as triethylamin and trapping the forming azomethine-ylides in situ with the desired dipolarophile compound of formula I-1.

Racemic mixtures can be converted into its enantiomeric components in conventional manner, for example by preparative HPLC or via diastereomeric salts.

The salt formation is effected at room temperatures in accordance with methods which are known per se and which are familiar to any person skilled in the art. Not only salts with inorganic acids, but also salts with organic acids come into consideration. Hydrochlorides, hydrobrornides, sulphates, nitrates, citrates, acetates, maleates, succinates, methanesulphonates, p-toluenesulfonates and the like are examples of such salts.

The compounds of formula II, III and IV, which are used as starting materials, are known compounds or can be prepared by methods known per se.

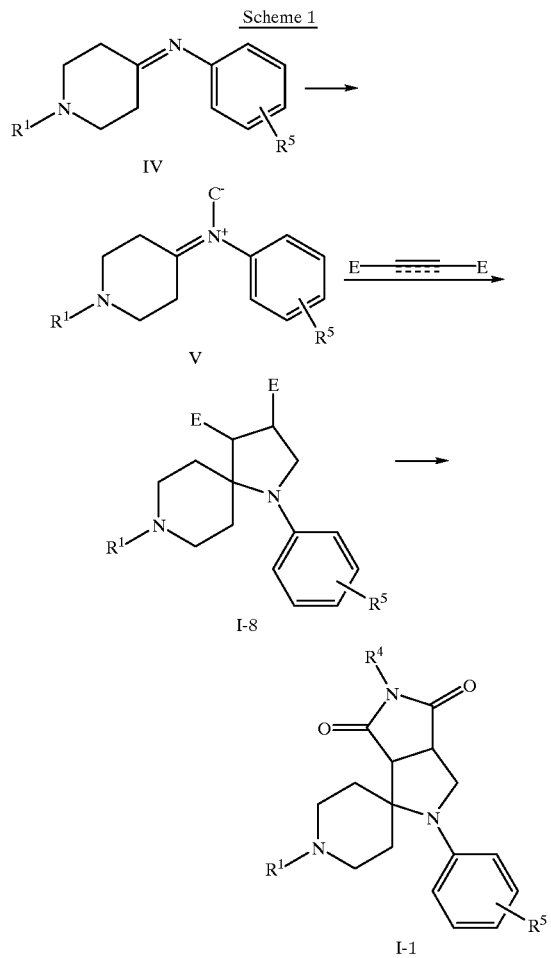

In this scheme $R^1$, $R^4$ and $R^5$ have the significances given above and E is an electron withdrawing group, for example E/E is —C(O)N(CH$_3$)C(O)—.

The cycloaddition with azomethine ylides is described in Doepp et al, Chem. Ber. 121, 1988, 1651–1655. The process is carried out by treating an imine with equimolar amouts of (trimethylsilyl)methyl-trifluoromethane sulfonate and caesium fluoride in an inert solvent, preferably 1,2-dimethoxyethane. The azomethine ylide is in situ trapped with a dipolarophile, for example with N-methyl maleimide, dimethyl maleate or dimethyl acetylenedicarboxylate. Another method suitable to prepare these compounds is described in Tsuge et al., Chem. Lett., 1986, S. 973.

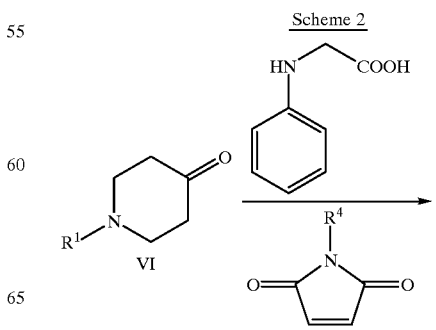

Scheme 2

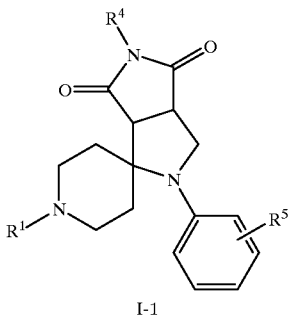

I-1

This process is carried out by reacting a ketone of formula VI with a slight excess of N-phenyl-glycine in an inert solvent, such as toluene, at elevated temperatures in the presence of a base, such as triethylamine and trapping the forming ylides in situ with the desired dipolarophile.

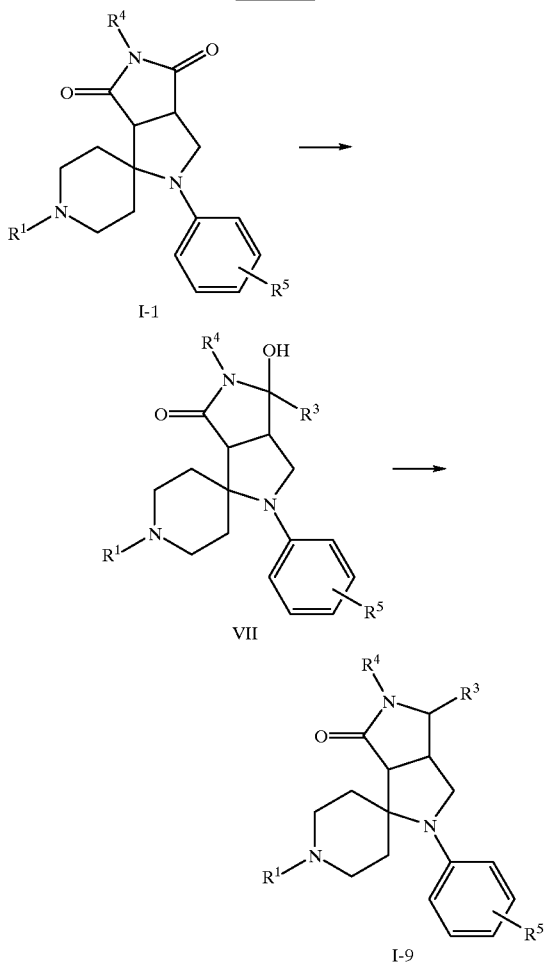

Scheme 3 describes a process for preparation of a compound of formula I-9, wherein a compound of formula I-1 is treated with a Grignard reagent ($R^3MgCl$ or $R^3MgBr$) in an inert solvent, such as diethyl ether or tetrahydrofuran. The resulting compound of formula VII is then reduced with sodium cyanoborohydride in a solution of methanol and trifluoroacetic acid.

As mentioned earlier, the compounds of formula I and their pharmaceutically usuable addition salts possess valuable pharmacodynamic properties. It has been found that the compounds of the present invention are agonists of the OFQ receptor and have effects in animal models of psychiatric, neurological and physiological disorders, such as anxiety, stress disorders, depression, trauma, memory loss due to Alzheimer's disease or other dementias, deficits in cognition and learning, epilepsy and convulsions, acute and/or chronic pain conditions, symptoms of addictive drug withdrawal, control of water balance, $Na^+$ excretion, arterial blood pressure disorders and metabolic disorders such as obesity.

The compounds were tested for pharmacologic activity in accordance with the methods given hereinafter:

Methods of OFQ-R Binding Assay

Cell Culture

HEK-293 cells adapted to suspension growth (293s) were cultured in HL medium plus 2% FBS. The cells were transfected with the rat OFQ receptor cDNA (LC132), FEBS Lett. 347, 284–288, 1994, cloned in the expression vector pCEP4 (Invitrogen, SanDiego, Calif., USA) using lipofectin (Life Technologies, Bethesda, Md., USA). Transfected cells were selected in the presence of hygromycin (1000 U/ml) (Calbiochem, SanDiego, Calif., USA). A pool of resistant cells was tested for OFQ-R expression by binding of [$^3$H]-OFQ (Amersham PLC, Buckinghamshire, England). These cells (293s-OFQ-R) were expanded for large scale culture and membrane preparation.

Membrane preparation

293s-OFQ-R cells were harvested by centrifugation, washed 3 times with phosphate buffered saline (PBS) before resuspension in buffer A (50 mM Tris-HCl, pH 7.8, 5 mM $MgCl_2$, 1 mM EGTA) and disruption with a tissue homogenizer (30 seconds, setting 4, Pt 20, Kinematica, Kriens-Lucern, Switzerland). A total membrane fraction was obtained by centrifugation at 49,000×g at 4° C. This procedure was repeated twice and the pellet was resuspended in buffer A. Aliquots were stored at −70° C. and protein concentrations were determined using the BCA™ Protein Assay Reagent (Pierce, Rockford, Ill.) following the manufacturer's recommendations.

Binding Assays

[$^3$H]-OFQ competition studies were carried out with 77 μg membrane protein in a final assay volume of 0.5 ml buffer A plus 0.1% BSA and 0.01% bacitracin (Boehringer-Mannheim, Mannheim, Germany) for one hour at room temperature. 50 nM unlabeled OFQ was used to define the non-specific binding. The assays were terminated by filtration through Whatman GF/C filters (Unifilter-96, Canberra Packard S.A., Zurich, Switzerland) pretreated with 0.3% polyethyleneimine (Sigma, St Louis, Mo., USA) and 0.1% BSA (Sigma) for 1 hour. The filters were washed 6 times with 1 ml of ice cold 50 mM Tris-HCl pH 7.5. The retained radioactivity was counted on a Packard Top-Count microplate scintillation counter after addition of 40 μl of Microscint 40 (Canberra Packard). The effects of compounds were determined using at least 6 concentrations in triplicate, and determined twice. $IC_{50}$ values were determined by curve fitting and these calues were converted to $K_i$ values by the method of Cheng and Prusoff, Biochem. Pharmacol., 22, 3099, 1973.

The affinity to the OFQ-receptor, given as pKi, is in the range of 7.5 to 10.0.

GTPγS Binding Assay

This assay was used to define whether the compounds of this invention are agonists or antagonists of the OFQ receptor.

Agonist-mediated binding of GTPγS was investigated in 96-well plates using a Scintillation Proximity Assay (SPA) using either hOFQR membranes or membranes prepared from cells transfected with the various human opiate receptors (μ, δ and κ). Binding was performed in 200 μl 20 mM HEPES-buffer (pH 7.4, plus 6 mM $MgCl_2$ and 100 mM NaCl), supplemented with 20 μM GDP, 10 μm cold GTPγS and 0.3 nM GTP[$γ^{35}$]S (1130 Ci/mmol). Twenty μg membranes, 1 mg wheatgerm agglutinin SPA beads (Amersham, Little Chalfont, UK) and either OFQ ($10^{-5}$ M to $10^{-10}$ M) or synthetic compounds ($10^{-4}$ M to $10^{-9}$ M) were added.

The reaction mixture was incubated on a shaker for 60 min at 22° C. and then centrifuged for 5 min at 1500 rpm in an Eppendorf 5403 centrifuge. Finally the plates were read in a Top counter (Packard).

Compounds of this invention have been shown to be agonists of the OFQ receptor having $PEC_{50}$ ranges from about 4.7 to about 7.1.

The preparation of the following compounds is described in Examples 1–166:

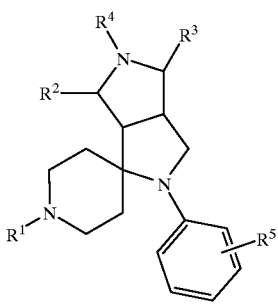

I

| Example | $R^1$ | $R^2$ | $R^3$ | $R^4$ | $R^5$ |
|---|---|---|---|---|---|
| 1 | 4-methylindan-2-yl | =O | =O | $CH_3$ | H |
| 2 | 4-methylindan-2-yl | =O | =O | H | H |
| 3 | indan-1-yl (methyl) | =O | =O | $CH_3$ | H |
| 4 | indan-1-yl (methyl) | =O | =O | H | H |
| 5 | (S)-1,2,3,4-tetrahydronaphthalen-1-yl | =O | =O | $CH_3CH_2$ | H |

-continued
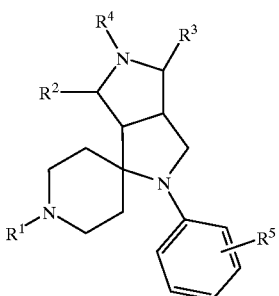
I
| Example | R¹ | R² | R³ | R⁴ | R⁵ |
|---|---|---|---|---|---|
| 6 | tetrahydronaphthyl | =O | =O | CH₃CH₂ | H |
| 7 | tetrahydronaphthyl | =O | =O | CH₃ | H |
| 8 | tetrahydronaphthyl | =O | =O | CH₃ | H |
| 9 | tetrahydronaphthyl | =O | =O | H | H |
| 10 | tetrahydronaphthyl | =O | =O | H | H |
| 11 | decahydronaphthyl | =O | =O | CH₃CH₂ | H |
| 12 | decahydronaphthyl | =O | =O | CH₃ | H |

-continued
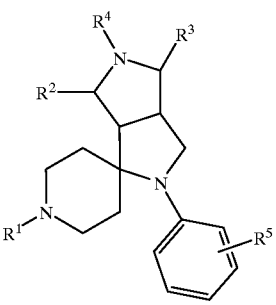
I
| Example | R¹ | R² | R³ | R⁴ | R⁵ |
|---|---|---|---|---|---|
| 13 | (trans-decalin-2-yl, methyl) | =O | =O | H | H |
| 14 | (4-methylindan-2-yl) | H₂ | H₂ | CH₃CH₂ | H |
| 15 | (4-methylindan-2-yl) | H₂ | H₂ | CH₃ | H |
| 16 | (4-methylindan-2-yl) | H₂ | H₂ | H | H |
| 17 | (1,2,3,4-tetrahydronaphthalen-1-yl) | H₂ | H₂ | CH₃CH₂ | H |
| 18 | (1,2,3,4-tetrahydronaphthalen-1-yl) | H₂ | H₂ | CH₃CH₂ | H |
| 19 | (1,2,3,4-tetrahydronaphthalen-1-yl) | H₂ | H₂ | CH₃ | H |

-continued
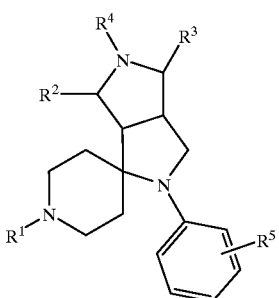
I
| Example | R¹ | R² | R³ | R⁴ | R⁵ |
|---|---|---|---|---|---|
| 20 | 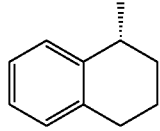 | H₂ | H₂ | CH₃ | H |
| 21 | 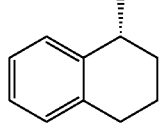 | H₂ | H₂ | H | H |
| 22 | 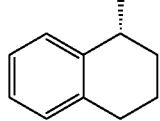 | H₂ | H₂ | H | H |
| 23 | 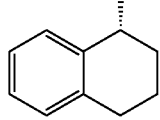 | H₂ | H₂ | 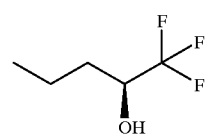 | H |
| 24 | 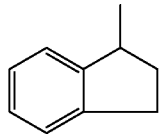 | H₂ | H₂ | CH₃CH₂ | H |
| 25 | 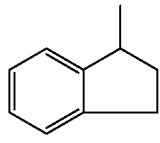 | H₂ | H₂ | CH₃ | H |
| 26 | 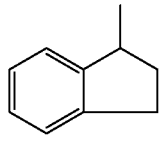 | H₂ | H₂ | CH₃ | H |

-continued
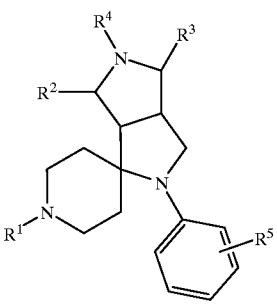
I
| Example | R¹ | R² | R³ | R⁴ | R⁵ |
|---|---|---|---|---|---|
| 27 | *trans-decalin-2-yl (with methyl)* | H₂ | H₂ | CH₃CH₂ | H |
| 28 | *trans-decalin-2-yl (with methyl)* | H₂ | H₂ | CH₃ | H |
| 29 | *trans-decalin-2-yl (with methyl)* | H₂ | H₂ | H | H |
| 30 | *2-(naphth-2-yl)ethyl* | =O | =O | H | H |
| 31 | *2-cyclononyl-methyl* | H₂ | H₂ | CH₃ | H |
| 32 | *2-(naphth-2-yl)ethyl* | H₂ | H₂ | H | H |
| 33 | *2-(naphth-1-yl)ethyl* | H₂ | H₂ | H | H |

-continued
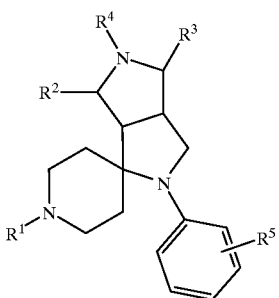
I
| Example | R¹ | R² | R³ | R⁴ | R⁵ |
|---|---|---|---|---|---|
| 34 | acenaphthyl (methyl) | =O | =O | CH₃ | H |
| 35 | acenaphthyl (methyl) | =O | =O | CH₃ | H |
| 36 | acenaphthyl (methyl) | H₂ | H₂ | CH₃ | H |
| 37 | acenaphthyl (methyl) | H₂ | H₂ | CH₃ | H |
| 38 | perhydrophenalenyl (methyl) | =O | =O | CH₃ | H |
| 39 | perhydrophenalenyl (methyl) | =O | =O | CH₃ | H |

-continued
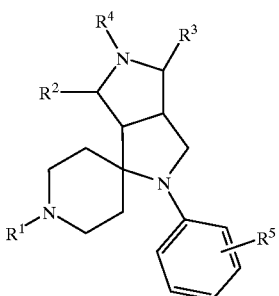
I
| Example | R¹ | R² | R³ | R⁴ | R⁵ |
|---|---|---|---|---|---|
| 40 | (2,3,3a-H perhydrophenalenyl, methyl wedge) | H₂ | H₂ | CH₃ | H |
| 41 | (2,3,3a-H perhydrophenalenyl, methyl dash) | H₂ | H₂ | CH₃ | H |
| 42 | (methylcyclohexyl) | =O | =O | CH₃ | H |
| 43 | (methylcycloheptyl) | =O | =O | CH₃ | H |
| 44 | (methylcycloheptyl) | H₂ | H₂ | CH₃ | H |
| 45 | (methylcyclooctyl) | =O | =O | CH₃ | H |
| 46 | (methylcyclooctyl) | H₂ | H₂ | CH₃ | H |

-continued
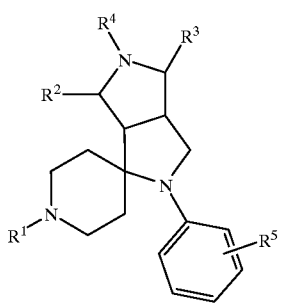
I
| Example | R¹ | R² | R³ | R⁴ | R⁵ |
|---|---|---|---|---|---|
| 47 | decalinyl | =O | =O | CH₃ | H |
| 48 | perhydrophenalenyl | H₂ | H₂ | CH₃ | H |
| 49 | decalinyl | H₂ | H₂ | CH₃ | H |
| 50 | cyclododecyl | =O | =O | CH₃ | H |
| 51 | cycloheptyl | H₂ | H₂ | CH₃ | H |
| 52 | cyclododecyl | H₂ | H₂ | CH₃ | H |
| 53 | cyclododecyl | =O | =O | CH₃ | H |

-continued
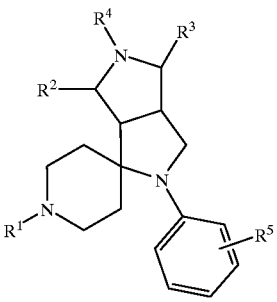
| Example | R¹ | R² | R³ | R⁴ | R⁵ |
|---|---|---|---|---|---|
| 54 | 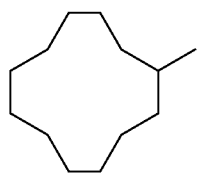 | H₂ | H₂ | CH₃ | H |
| 55 | 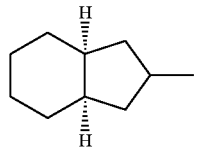 | =O | =O | CH₃ | H |
| 56 | 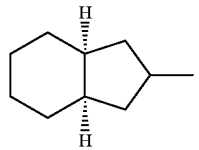 | H₂ | H₂ | CH₃ | H |
| 57 | 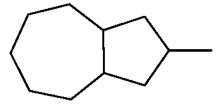 | =O | =O | CH₃ | H |
| 58 | 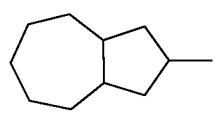 | H₂ | H₂ | CH₃ | H |
| 59 | 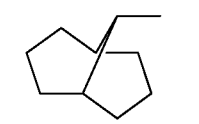 | =O | =O | CH₃ | H |
| 60 | 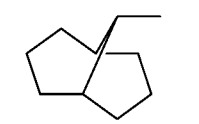 | H₂ | H₂ | CH₃ | H |

-continued

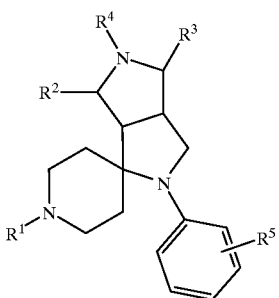

I

| Example | R¹ | R² | R³ | R⁴ | R⁵ |
|---|---|---|---|---|---|
| 61 | (bicyclic structure with H stereochemistry, methyl) | =O | =O | CH₃ | H |
| 62 | (bicyclic structure with H stereochemistry, methyl) | H₂ | H₂ | CH₃ | H |
| 63 | (bicyclic structure with H, methyl) | H₂ | H₂ | CH₃ | H |
| 64 | (tetrahydronaphthalenyl with methyl) | =O | =O | CH₃ | H |
| 65 | (tetrahydronaphthalenyl with methyl) | H₂ | H₂ | CH₃ | H |
| 66 | (bicyclic structure with CH₃ and isopropyl) | =O | =O | CH₃ | H |
| 67 | (bicyclic structure with CH₃ and isopropyl) | H₂ | H₂ | CH₃ | H |

-continued
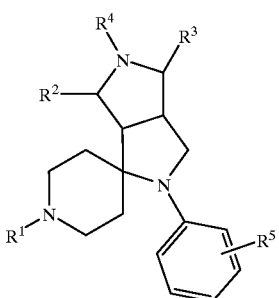
I
| Example | R¹ | R² | R³ | R⁴ | R⁵ |
|---|---|---|---|---|---|
| 68 | cyclodecyl-CH- | =O | =O | CH₃CH₂ | H |
| 69 | cyclodecyl-CH- | H₂ | H₂ | CH₃CH₂ | H |
| 70 | cyclononyl-CH- | =O | =O | CH₃CH₂ | H |
| 71 | cyclononyl-CH- | H₂ | H₂ | CH₃CH₂ | H |
| 72 | cyclodecyl-CH- | H₂ | H₂ | cyclohexyl | H |
| 73 | acenaphthyl-CH- | H₂ | H₂ | CH₃ | H |
| 74 | acenaphthyl-CH- | H₂ | H₂ | CH₃ | H |
| 75 | cyclodecyl-CH- | =O | =O | benzyl | H |

-continued

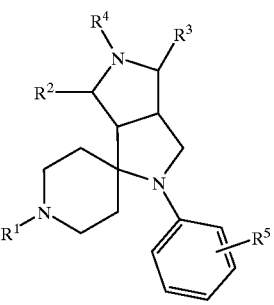

I

| Example | R¹ | R² | R³ | R⁴ | R⁵ |
|---|---|---|---|---|---|
| 76 | cyclodecyl | H₂ | H₂ | benzyl | H |
| 77 | 4-isopropylcyclohexyl | =O | =O | CH₃ | H |
| 78 | 4-isopropylcyclohexyl | =O | =O | phenyl | H |
| 79 | 4-isopropylcyclohexyl | =O | =O | H | H |
| 80 | 4-isopropylcyclohexyl | =O | =O | CH₃CH₂ | H |
| 81 | 4-isopropylcyclohexyl | =O | =O | cyclopropylmethyl | H |
| 82 | 4-isopropylcyclohexyl | =O | =O | cyclohexyl | H |
| 83 | 4-isopropylcyclohexyl | =O | =O | benzyl | H |
| 84 | 4-isopropylcyclohexyl | =O | =O | n-butyl | H |
| 85 | 4-isopropylcyclohexyl | =O | =O | tetrahydrofuran-3-yl | H |

-continued

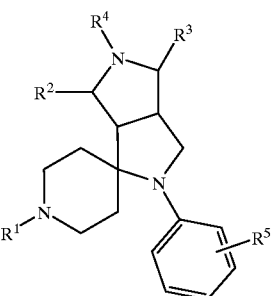

| Example | R¹ | R² | R³ | R⁴ | R⁵ |
|---|---|---|---|---|---|
| 86 | 4-isopropylcyclohexyl | =O | =O | 3-benzyloxypropyl | H |
| 87 | 4-isopropylcyclohexyl | =O | =O | (3-methyl-3-ethyl-oxetanyl)methyl | H |
| 88 | 4-isopropylcyclohexyl | =O | =O | 3-morpholinopropyl | H |
| 89 | 4-isopropylcyclohexyl | H₂ | H₂ | CH₃ | H |
| 90 | 4-isopropylcyclohexyl | H₂ | H₂ | CH₃CH₂ | H |
| 91 | 4-isopropylcyclohexyl | H₂ | H₂ | phenyl | H |
| 92 | 4-isopropylcyclohexyl | H₂ | H₂ | (3-methyl-3-ethyl-oxetanyl)methyl | H |
| 93 | 4-isopropylcyclohexyl | H₂ | H₂ | 3-benzyloxypropyl | H |
| 94 | 4-isopropylcyclohexyl | H₂ | H₂ | benzyl | H |
| 95 | 4-isopropylcyclohexyl | H₂ | H₂ | 3-methyltetrahydrofuranyl | H |

-continued

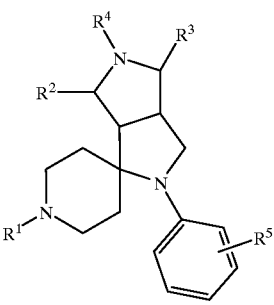

I

| Example | R¹ | R² | R³ | R⁴ | R⁵ |
|---|---|---|---|---|---|
| 96 | isopropylcyclohexyl | H₂ | H₂ | cyclohexyl | H |
| 97 | isopropylcyclohexyl | H₂ | H₂ | n-butyl | H |
| 98 | isopropylcyclohexyl | H₂ | H₂ | cyclopropylmethyl | H |
| 99 | isopropylcyclohexyl | H₂ | H₂ | CH₃ | H |
| 100 | isopropylcyclohexyl | H₂ | H₂ | CH₃ | H |
| 101 | isopropylcyclohexyl | =O | OH | CH₃ | H |
| 102 | isopropylcyclohexyl | =O | H₂ | CH₃ | H |
| 103 | isopropylcyclohexyl | =O | ◄CH₃ | CH₃ | H |
| 103 | isopropylcyclohexyl | =O | ⋯CH₃ | CH₃ | H |
| 104 | isopropylcyclohexyl | =O | ⋯phenyl | CH₃ | H |

-continued

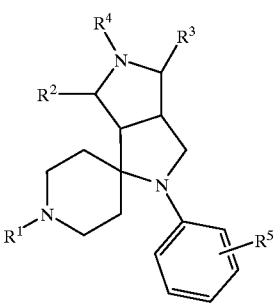

I

| Example | R¹ | R² | R³ | R⁴ | R⁵ |
|---|---|---|---|---|---|
| 105 | (4-isopropylcyclohexyl) | H₂ | ⋯⫽CH₃ | CH₃ | H |
| 106 | (4-isopropylcyclohexyl) | H₂ | H₂ | H | H |
| 107 | (4-isopropylcyclohexyl) | H₂ | H₂ | −CH₂CH₂CH₂OH | H |
| 108 | (4-isopropylcyclohexyl) | H₂ | H₂ | −S(O)₂CH₃ | H |
| 109 | (4-isopropylcyclohexyl) | H₂ | H₂ | −C(O)CH₃ | H |
| 110 | (4-isopropylcyclohexyl) | H₂ | H₂ | −C(O)CF₃ | H |
| 111 | (4-isopropylcyclohexyl) | H₂ | H₂ | −C(O)CH₂OCH₃ | H |
| 112 | (4-isopropylcyclohexyl) | H₂ | H₂ | −C(O)N(CH₂CH₃)₂ | H |
| 113 | (4-isopropylcyclohexyl) | H₂ | H₂ | −C(O)CH₂CH₂N(CH₃)₂ | H |

-continued
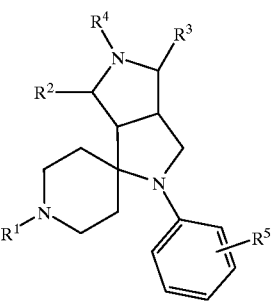
I
| Example | R¹ | R² | R³ | R⁴ | R⁵ |
|---|---|---|---|---|---|
| 114 | 4-isopropylcyclohexyl | H₂ | H₂ | -SO₂-(2-thienyl) | H |
| 115 | 4-isopropylcyclohexyl | H₂ | H₂ | -C(O)-(3-pyridyl) | H |
| 116 | 4-isopropylcyclohexyl | H₂ | H₂ | -SO₂-phenyl | H |
| 117 | 4-isopropylcyclohexyl | H₂ | H₂ | -C(O)-cyclopropyl | H |
| 118 | 4-isopropylcyclohexyl | H₂ | H₂ | -C(O)-(2-furyl) | H |
| 119 | 4-isopropylcyclohexyl | H₂ | H₂ | -C(O)-O-t-Bu | H |
| 120 | cyclodecyl | H₂ | H₂ | H | H |
| 121 | cyclodecyl | =O | =O | CH₃ | 4-F |
| 122 | 4-isopropylcyclohexyl | =O | =O | CH₃ | 4-F |

-continued
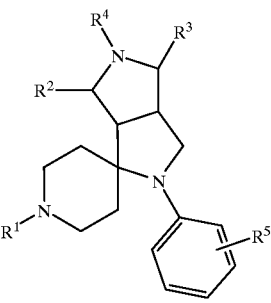
I
| Example | R¹ | R² | R³ | R⁴ | R⁵ |
|---|---|---|---|---|---|
| 123 | (isopropyl-cyclohexyl) | H₂ | H₂ | CH₃ | 4-F |
| 124 | (decalinyl) | H₂ | H₂ | CH₃ | 3-F |
| 125 | (decalinyl) | H₂ | H₂ | CH₃ | 4-F |
| 126 | (isopropyl-cyclohexyl) | =O | =O | CH₃ | 3-F |
| 127 | (decalinyl) | =O | =O | CH₃ | 4-CH₃ |
| 128 | (isopropyl-cyclohexyl) | H₂ | H₂ | CH₃ | 3-F |
| 129 | (cyclononyl) | H₂ | H₂ | CH₃ | H |
| 130 | (decalinyl) | H₂ | H₂ | CH₃ | 2-F |
| 131 | (decalinyl) | H₂ | H₂ | CH₃ | 4-CH₃ |
| 132 | (decalinyl) | =O | =O | CH₃ | 4-F |

-continued
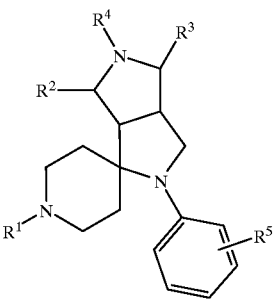
I
| Example | R¹ | R² | R³ | R⁴ | R⁵ |
|---|---|---|---|---|---|
| 133 | cyclohexylmethyl | =O | =O | CH₃ | 3-CH₃ |
| 134 | cyclohexylmethyl | =O | =O | CH₃ | 4-Cl |
| 135 | cyclohexylmethyl | H₂ | H₂ | CH₃ | 4-Cl |
| 136 | trans-4-isopropylcyclohexyl | H₂ | H₂ | CH₃ | 4-CH₃ |
| 137 | trans-4-isopropylcyclohexyl | H₂ | H₂ | CH₃ | 2-F |
| 138 | cyclohexylmethyl | H₂ | H₂ | CH₃ | 3-CH₃ |
| 139 | cyclooctylmethyl | H₂ | H₂ | CH₃ | 4-F |
| 140 | cyclooctylmethyl | H₂ | H₂ | benzyl | H |
| 141 | cyclooctylmethyl | H₂ | H₂ | H | H |
| 142 | cyclohexylmethyl | =O | =O | H | 4-F |

-continued
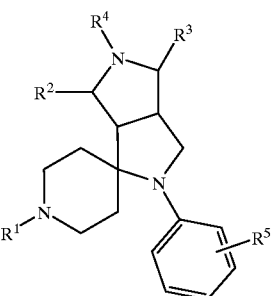
I
| Example | R¹ | R² | R³ | R⁴ | R⁵ |
|---|---|---|---|---|---|
| 143 | 4-isopropylcyclohexyl | =O | =O | CH₃ | 4-Cl |
| 144 | 4-isopropylcyclohexyl | H₂ | H₂ | CH₃ | 4-Cl |
| 145 | 4-isopropylcyclohexyl | =O | =O | CH₃ | 4-OCH₃ |
| 146 | 4-isopropylcyclohexyl | H₂ | H₂ | CH₃ | 4-OCH₃ |
| 147 | cyclodecyl | =O | =O | cyclopropylmethyl | 4-F |
| 148 | cyclodecyl | =O | =O | cyclobutylmethyl | 4-F |
| 149 | cyclodecyl | H₂ | H₂ | cyclobutylmethyl | 4-F |
| 150 | cyclodecyl | H₂ | H₂ | cyclopropylmethyl | 4-F |
| 151 | cyclodecyl | H₂ | H₂ | t-butyl | H |

-continued

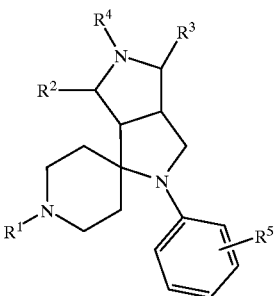

I

| Example | R¹ | R² | R³ | R⁴ | R⁵ |
|---|---|---|---|---|---|
| 152 | cyclodecyl-methyl | H₂ | H₂ | cyclopropyl-C(=O)- | H |
| 153 | cyclodecyl-methyl | H₂ | H₂ | CH₃-S(=O)₂- | H |
| 154 | 4-isopropylcyclohexyl | H₂ | H₂ | cyclopropyl-CH₂- | 4-F |
| 155 | 4-isopropylcyclohexyl | H₂ | H₂ | cyclopropyl-CH₂- | 3-F |
| 156 | cyclodecyl-methyl | =O | =O | cyclopropyl-CH₂- | H |
| 157 | cyclodecyl-methyl | H₂ | H₂ | phenyl-C(=O)- | H |
| 158 | cyclodecyl-methyl | H₂ | H₂ | cyclopropyl-C(=O)- | H |
| 159 | cyclodecyl-methyl | H₂ | H₂ | CH₃-C(=O)- | H |
| 160 | cyclodecyl-methyl | H₂ | H₂ | cyclopropyl-CH₂- | H |

-continued
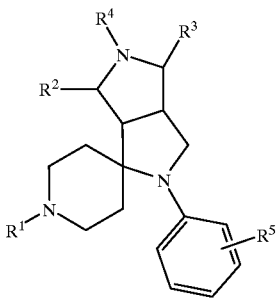
I
| Example | R¹ | R² | R³ | R⁴ | R⁵ |
|---|---|---|---|---|---|
| 161 | 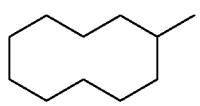 | H₂ | H₂ | 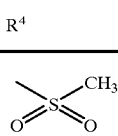 | H |
| 162 | 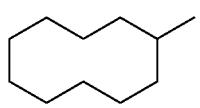 | H₂ | H₂ | 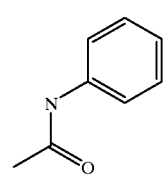 | H |
| 163 | 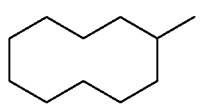 | H₂ | H₂ | 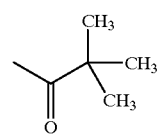 | H |
| 164 | 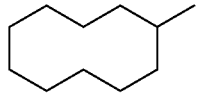 | H₂ | H₂ | 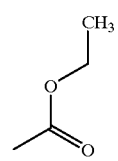 | H |
| 165 | 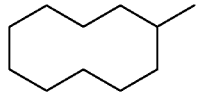 | H₂ | H₂ | 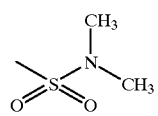 | H |
| 166 | 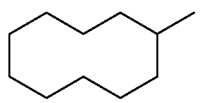 | H₂ | H₂ | 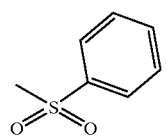 | H |
| 167 | 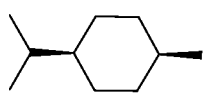 | H₂ | H₂ | 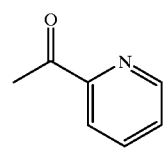 | H |

-continued

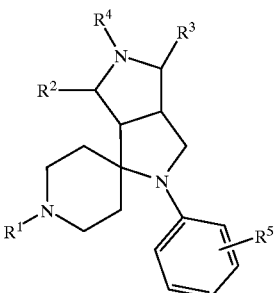

I

| Example | R¹ | R² | R³ | R⁴ | R⁵ |
|---|---|---|---|---|---|
| 168 | iPr-cyclohexyl | H₂ | H₂ | C(O)-2-thienyl | H |
| 169 | iPr-cyclohexyl | H₂ | H₂ | C(O)-morpholinyl | H |
| 170 | iPr-cyclohexyl | H₂ | H₂ | C(O)-4-pyridyl | H |
| 171 | iPr-cyclohexyl | H₂ | H₂ | C(O)-O-phenyl | H |
| 172 | iPr-cyclohexyl | H₂ | H₂ | C(O)-3-pyridyl | 4-F |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or supensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragees and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, the effective dosage for oral or parenteral administration is 0,01–20 mg/kg/day, preferred as a dosage of 0,1–10 mg/kg/day for all described indications. The dayly dosage for an adult of 70 kg weight is therefore between 0,7–1400 mg/day, preferred is 7–700 mg/day, although the above upper limit can also be exceeded when necessary.

The following Examples illustrate the present invention without limiting it. All temperatures are given in degrees Celsius.

EXAMPLE 1

Mixture of (3'aRS,6'aSR)-5'-methyl-1-[(RS)- and -[(SR)-4-methyl-indan-2-yl]-2'-phenyl-hexahydro-spiro[piperidine-4,1'-pyrrolo[3,4-c]pyrrole]-4',6'-dione hydrochloride (1:1)

A mixture of (3'aRS,6'aSR)-5'-methyl-1'-phenyl-hexahydro-spiro[piperidine-4,1'(2'H)-pyrrolo[3,4-c]pyrrole]-4',6'-dione (0.51 g, 1.7 mmol), 1,3-dihydro-4-methyl-2H-inden-2-one (1.7 mmol) and molecular sieves (4 Å, 5.0 g) in toluene (120 ml) was boiled for 16 h. The mixture was filtered while hot, the molecular sieves were washed thoroughly with hot toluene, and the filtrate was evaporated. The residue was dissolved in a mixture of THF (45 ml) and ethanol (5 ml), sodium cyanoborohydride (1.7 mmol) was added and the pH was adjusted to 4. The reaction mixture was stirred for 16 h at room temperature. Ice-water (30 ml) and potassium carbonate solution (50%, 10 ml) were added. The mixture was extracted with dichloromethane (3×60 ml), organic phases were pooled, washed with brine (40 ml), dried with $Na_2SO_4$ and the solvents were evaporated. Chromatography on silica gel (dichloromethane/methanol 2%) yielded the desired product (0.65 g, 83%) which was crystallized as its HCl-salt from ethylacetate to yield a colorless solid with m.p.>250° C. and MS: m/e=430.5 (M+H$^+$).

EXAMPLE 2

Mixture of (3'aRS,6'aSR)-1-[(RS)- and -[(SR)-4-methyl-indan-2-yl]-2'-phenyl-hexahydro-spiro [piperidine-4,1'-pyrrolo[3,4-c]pyrrole]-4',6'-dione fumarate (1:1)

The title compound, m.p.>230° C. dec. and MS: m/e=416.3 (M+H$^+$) was prepared in accordance with the general method of example 1 from 1,3-dihydro-4-methyl-2H-inden-2-one and (3'aRS,6'aSR)-2'-phenyl-hexahydro-spiro[piperidine-4,1'(2'H)-pyrrolo[3,4-c]pyrrole]-4',6'-dione.

EXAMPLE 3

Mixture of (3'aRS,6'aSR)-1-[(RS)- and -[(SR)-indan-1-yl]-5'-methyl-2'-phenyl-hexahydro-spiro [piperidine-4,1'-pyrrolo[3,4-c]pyrrole]-4',6'-dione hydrochloride (1:1)

A mixture of (3'aRS,6'aSR)-5'-methyl-1'-phenyl-hexahydro-spiro[piperidine-4,1'(2'H)-pyrrolo[3,4-c] pyrrole]-4',6'-dione (0.5 g, 1.7 mmol), 1-indanone (1.7 mm and tetraisopropyl-orthotitanate (2.1 mmol) in THF (30 ml) was stirred at room temperature for 16 h. The solvent was removed in vacuo the residue was dissolved in ethanol (10 ml), sodium cyanoborohydride was added and the mixture was stirred for 16 h at room temperature. Water was added, the suspension was filtered and the filtrate was evaporated. Chromatography on silica gel (dichloromethane/methanol 2%) yielded the desired product (0.35 g, 50%) which was crystallized as its HCl-salt from ethylacetate to yield a colorless solid with m.p.>171° C. dec. and MS: m/e=416.2 (M+H$^+$).

EXAMPLE 4

Mixture of (3'aRS,6'aSR)-1-[(RS)- and -[(SR)-indan-1-yl]-2'-phenyl-hexahydro-spiro[piperidine-4,1'-pyrrolo[3,4-c]pyrrole]-4',6'-dione fumarate (1:2)

The title compound, m.p.>148° C. dec. and MS: m/e=402.5 (M+H$^+$) was prepared in accordance with the general method of example 3 from 1-indanone and (3'aRS,6'aSR)-2'-phenyl-hexahydro-spiro[piperidine-4,1'(2'H)-pyrrolo[3,4-c]pyrrole]-4',6'-dione.

EXAMPLE 5

(3'aS,6'aR)-5'-Ethyl-1-(R)-1,2,3,4-tetrahydro-naphtalen-1-yl]-2'-phenyl-hexahydro-spiro [piperidine-4,1'-pyrrolo[3,4-c]pyrrole]-4',6'-dione A mixture of (R)-1-(1,2,3,4-tetrahydro-naphthalen-1-yl)-piperidinine (0.75 g, 3.2 mmol), aniline (3.2 mmol) and p-toluenesulfonic acid (10 mg) in toluene (30 ml) was boiled with separation of water for 20 h. The solvent was removed in vacuo and the residue was dissolved in dimethoxyethane (25 ml) and cooled to 0° C. To the cold solution was added (tnrmethylsilyl)-methyl-trifluoromethanesulfonate (3.2 mmol), the mixture was allowed to warm and stirred for 2 h at room temperature. Cesium fluoride (3.2 mmol) and N-ethyl maleimide (9 mmol) was added and the mixture was stirred for 20 h at room temperature. The solvent was removed in vacuo and the residue was partitioned between sodium bicarbonate and dichloromethane. Organic phases were pooled, dried with $Na_2SO_4$ and evaporated. Chromatography on silica gel (ethylacetate/hexane 1:2) yielded the desired product (0.64 g, 45%) as a yellow foam with MS: m/e=444.4 (M+H$^+$).

EXAMPLE 6

(3'aR,6'aS)-5'-Ethyl-2'-phenyl-1-[(R)-1,2,3,4-tetrahydro-naphtalen-1-yl]-hexahydro-spiro [piperidine-4,1'-pyrrolo[3,4-c]pyrrole]-4',6'-dione fumarate (1:1)

The title compound, m.p. 222–224° C. and MS: m/e=444.4 (M+H$^+$), was prepared in accordance with the general method of example 5 from (R)-1-(1,2,3,4-tetrahydro-naphthalen-1-yl)-piperidin-4-one, aniline, (trimethylsilyl)-methyl-trifluoromethanesulfonate and N-ethyl maleimide and separated from its diastereomer (example 5) by chromatography on silica gel with ethylacetate/hexane (1:2).

EXAMPLE 7

(3'aS,6'aR)-5'-Methyl-2'-phenyl-1-[(R)-1,2,3,4-tetrahydro-naphtalen-1-yl]-hexahydro-spiro [piperidine-4,1'-pyrrolo[3,4-c]pyrrole]-4',6'-dione The title compound, MS: m/e=430.5 (M+H$^+$), was prepared in accordance with the general method of example 5 from (R)-1-(1,2,3,4-tetrahydro-naphthalen-1-yl)-piperidin-4-one, aniline, (trimethylsilyl)-methyl-trifluoromethanesulfonate and N-methyl maleimide.

EXAMPLE 8

(3'aR,6'aS)-5'-Methyl-2'-phenyl-1-[(R)-1,2,3,4-tetrahydro-naphtalen-1-yl]-hexahydro-spiro[piperidine-4,1'-pyrrolo[3,4-c]pyrrole]-4',6'-dione The title compound, MS: m/e=430.5 (M+H$^+$), was prepared in accordance with the general method of example 5 from (R)-1-(1,2,3,4-tetrahydro-naphthalen-1-yl)-piperidin-4-one, aniline, (trimethylsilyl)-methyl-trifluoromethanesulfonate and N-methyl maleimide and separated from its diastereomer (example 7) by chromatography on silica gel with ethylacetate/hexane (1:2).

EXAMPLE 9

(3'aS,6'aR)-2'-Phenyl-1-(R)-1,2,3,4-tetrahydro-naphtalen-1-yl]-hexahydro-spiro[piperidine-4,1'-pyrrolo[3,4-c]pyrrole]-4',6'-dione The title compound, MS: m/e=416.2 (M+H$^+$), was prepared in accordance with the general method of example 5 from (R)-1-(1,2,3,4-tetrahydro-naphthalen-1-yl)-piperidin-4-one, aniline, (trimethylsilyl)-methyl-trifluoromethanesulfonate and maleimide.

EXAMPLE 10

(3'aR,6'aS)-2'-Phenyl-1-(R)-1,2,3,4-tetrahydro-naphtalen-1-yl]-hexahydro-spiro[piperidine-4,1'-pyrrolo[3,4-c]pyrrole]-4',6'-dione The title compound, MS: m/e=416.2 (M+H$^+$), was prepared in accordance with the general method of example 5 from (R)-1-(1,2,3,4-tetrahydro-naphthalen-1-yl)-piperidin-4-one, aniline, (trimethylsilyl)-methyl-trifluoromethanesulfonate and maleimide and separated from its diastereomer (example 9) by chromatography on silica gel with ethylacetate/hexane (1:2).

EXAMPLE 11

Mixture of (3'aSR,6'aRS)- and (3'aRS,6'aSR)-5'-ethyl-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione fumarate (1:1)

The title compound, m.p. 177–180° C. and MS: m/e=450.4 (M+H$^+$), was prepared in accordance with the general method of example 5 from (2RS,4aSR,8aRS)-1-(decahydro-naphthalen-2-yl)-piperidin-4-one, aniline, (trimethylsilyl)-methyl-trifluoromethanesulfonate and N-ethyl maleimide.

EXAMPLE 12

Mixture of (3'aSR,6'aRS)- and (3'aRS,6'aSR)-5'-methyl-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione hydrochloride (1:1)

The title compound, m.p. 168–171° C. and MS: m/e=436.5 (M+H$^+$), was prepared in accordance with the general method of example 5 from (2RS,4aSR,8aRS)-1-(decahydro-naphthalen-2-yl)-piperidin-4-one, aniline, (trimethylsilyl)-methyl-trifluoromethanesulfonate and N-methyl maleimide.

EXAMPLE 13

Mixture of (3'aSR,6'aRS)- and (3'aRS,6'aSR)-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione fumarate (1:1)

The title compound, m.p. 247–250° C. dec. and MS: m/e=422.5 (M+H$^+$), was prepared in accordance with the general method of example 5 from (2RS,4aSR,8aRS)-1-(decahydro-naphthalen-2-yl)-piperidin-4-one, aniline, (trimethylsilyl)-methyl-trifluoromethanesulfonate and maleimide.

EXAMPLE 14

Mixture of (3'aRS,6'aSR)- and (3'aSR,6'aRS)-5'-ethyl-1-[(RS)-4-methyl-indan-2-yl]-2'-phenyl-hexahydro-spiro[piperidine-4,1'-pyrrolo[3,4-c]pyrrole]fumarate (1:2)

The title compound, m.p.>165° C. dec. and MS: m/e=416.3 (M+H$^+$) was prepared in accordance with the general method of example 1 from 1,3-dihydro-4-methyl-2H-inden-2-one and (3'aRS,6'aSR)-5'-ethyl-2'-phenyl-hexahydro-spiro[piperidine-4,1'-pyrrolo[3,4-c]pyrrole].

EXAMPLE 15

Mixture of (3'aRS,6'aSR)- and (3'aSR,6'aRS)-5'-methyl-1-[(RS)-4-methyl-indan-2-yl]-2'-phenyl-hexahydro-spiro[piperidine-4,1'-pyrrolo[3,4-c]pyrrole]fumarate (1:2)

A mixture of (3'aRS,6'aSR)-5'-methyl-1-[(RS)- and -[(SR)-4-methyl-indan-2-yl]-2'-phenyl-hexahydro-spiro[piperidine-4,1'-pyrrolo[3,4-c]pyrrole]-4',6'-dione (0.49 g, 1.1 mol) and lithium aluminiumhydride (3.4 mmol) in diethylether (12 ml) and THF (10 ml) was stirred for 0.5 h at room temperature and boiled for another 1.5 h. The reaction mixture was quenched with water (40 μl), sodium hydroxide solution (15%, 40 μl) and water (120 μl), stirred for 1 h, filtered and the filtrate was evaporated. Chromatography on silica gel deactivated with triethylamine (dichloromethane/methanol 5%) yielded the desired product (0.37 g, 81%) which was crystallized as its fumarate-salt from ethylacetate to yield a colorless solid with m.p.>146° C. dec. and MS: m/e=402.5 (M+H$^+$).

EXAMPLE 16

Mixture of (3'aRS,6'aSR)- and (3'aSR,6'aRS)-1-[(RS)-4-methyl-indan-2-yl]-2'-phenyl-hexahydro-spiro[piperidine-4,1'-pyrrolo[3,4-c]pyrrole]fumarate (1:2.1)

The title compound, m.p.>181° C. dec. and MS: m/e=388.4 (M+H$^+$) was prepared in accordance with the general method of example 15 from (3'aRS,6'aSR)-1-[(RS)- and -[(SR)-4-methyl-indan-2-yl]-2'-phenyl-hexahydro-spiro[piperidine-4,1'-pyrrolo[3,4-c]pyrrole]-4',6'-dione.

EXAMPLE 17

(3'aR,6'aS)-5'-Ethyl-2'-phenyl-1-[(R)-1,2,3,4-tetrahydro-naphtalen-1-yl]-hexahydro-spiro[piperidine-4,1'-pyrrolo[3,4-c]pyrrole]

The title compound, MS: m/e=416.3 (M+H$^+$) was prepared in accordance with the general method of example 15 from (3'aS,6'aR)-5'-ethyl-1-[(R)-1,2,3,4-tetrahydro-naphtalen-1-yl]-2'-phenyl-hexahydro-spiro[piperidine-4,1'-pyrrolo[3,4-c]pyrrole]-4',6'-dione.

EXAMPLE 18

(3'aS,6'aR)-5'-Ethyl-2'-phenyl-1-[(R)-1,2,3,4-tetrahydro-naphtalen-1-yl]-hexahydro-spiro [piperidine-4,1'-pyrrolo[3,4-c]pyrrole]

The title compound, MS: m/e=416.3 (M+H$^+$) was prepared in accordance with the general method of example 15 from (3'aR,6'aS)-5'-ethyl-1-[(R)-1,2,3,4-tetrahydro-naphtalen-1-yl]-2'-phenyl-hexahydro-spiro[piperidine-4,1'-pyrrolo[3,4-c]pyrrole]-4',6'-dione.

EXAMPLE 19

(3'aR,6'aS)-5'-Methyl-2'-phenyl-1-[(R)-1,2,3,4-tetrahydro-naphtalen-1-yl]-hexahydro-spiro [piperidine-4,1'-pyrrolo[3,4-c]pyrrole]

The title compound, MS: m/e=402.5 (M+H$^+$) was prepared in accordance with the general method of example 15 from (3'aS,6'aR)-5'-methyl-2'-phenyl-1-[(R)-1,2,3,4-tetrahydro-naphtalen-1-yl]-hexahydro-spiro[piperidine-4,1'-pyrrolo[3,4-c]pyrrole]-4',6'-dione.

EXAMPLE 20

(3'aS,6'aR)-5'-Methyl-2'-phenyl-1-f(R)-1,2,3,4-tetrahydro-naphtalen-1-yl]-hexahydro-spiro] piperidine-4,1'-pyrrolo[3,4-c]pyrrole]

The title compound, MS: m/e=402.5 (M+H$^+$) was prepared in accordance with the general method of example 15 from (3'aR,6'aS)-5'-methyl-2'-phenyl-1-[(R)-1,2,3,4-tetrahydro-naphtalen-1-yl]-hexahydro-spiro[piperidine-4,1'-pyrrolo[3,4-c]pyrrole]-4',6'-dione.

EXAMPLE 21

(3'aS,6'aR)-2'-Phenyl-1-[(R)-1,2,3,4-tetrahydro-naphtalen-1-yl]-hexahydro-spiro[piperidine-4,1'-pyrrolo[3,4-c]pyrrole]

The title compound, MS: m/e=388.3 (M+H$^+$) was prepared in accordance with the general method of example 15 from (3'aR,6'aS)-2'-phenyl-1-[(R)-1,2,3,4-tetahydro-naphtalen-1-yl]-hexahydro-spiro[piperidine-4,1'-pyrrolo[3,4-c]pyrrole]-4',6'-dione.

EXAMPLE 22

(3'aR,6'aS)-2'-Phenyl-1-[(R)-1,2,3,4-tetrahydro-naphtalen-1-yl]-hexahydro-spiro[piperidine-4,1'-pyrrolo[3,4-c]pyrrole]

The title compound, MS: m/e=388.3 (M+H$^+$) was prepared in accordance with the general method of example 15 from (3'aS,6'aR)-2'-phenyl-1-[(R)-1,2,3,4-tetrahydro-naphtalen-1-yl]-hexahydro-spiro[piperidine-4,1'-pyrrolo[3,4-c]pyrrole]-4',6'-dione.

EXAMPLE 23

(3'aR,6'aS)-2'-Phenyl-1-[(R)-1,2,3,4-tetrahydro-naphthalen-1-yl]-5'-[(S)-4,4,4-trifluoro-3-hydroxy-butyl]-hexahydro-spiro[piperidine-4,1'-pyrrolo[3,4-c]pyrrole]

A mixture of (3aR,6'aS)-2-phenyl-1-[(R)-1,2,3,4-tetrahydro-naphtalen-1-yl]-hexahydro-spiro[piperidine-4,1'-pyrrolo[3,4-c]pyrrole] (45 mg, 0.12 mmol), (S)-toluene-4-sulfonic acid 4,4,4-trifluoro-3-hydroxy-butyl ester (0.13 mmol) and potassium carbonate (0.23 mmol) in 2-butanone (2 ml) was boiled for 16 h. Water (10 ml) was added and the mixture was extracted with ethylacetate (2×10 ml). Organic phases were pooled, dried with Na$_2$SO$_4$ and the solvents were evaporated. Chromatography on silica gel (dichloromethane/methanol 2%) yielded the desired product (32 mg, 54%) as a beige foam with MS: m/e=514.4 (M+H$^+$).

EXAMPLE 24

Mixture of (3'aRS,6'aSR)- and (3'aSR,6'aRS)-5'-ethyl-1-[(RS)-indan-1-yl]-2'-phenyl-hexahydro-spiro [piperidine-4,1'-pyrrolo[3,4-c]pyrrole]fumarate (1:1.75)

The title compound, m.p.>132° C. dec. and MS: m/e=402.5 (M+H$^+$) was prepared in accordance with the general method of example 3 from 1-indanone and (3'aRS,6'aSR)-5'-ethyl-2'-phenyl-hexahydro-spiro[piperidine-4,1'-pyrrolo [3,4-c]pyrrole].

EXAMPLE 25

(3'aRS,6'aSR)-1-[(RS)- or -[(SR)-indan-1-yl]-5'-methyl-2'-phenyl-hexahydro-spiro[piperidine-4,1'-pyrrolo[3,4-cipyrrole]fumarate (1:3)

The mixture of (3'aRS,6'aSR)-1-[(RS)- and -[(SR)-indan-1-yl]-5'-methyl-2'-phenyl-hexahydro-spiro[piperidine-4,1'-pyrrolo[3,4-c]pyrrole]-4',6'-dione was separated by chromatography on silica gel with dichloromethane/methanol 2% into its diastereoisomers and reduced following the general procedure of example 15 to yield the title compound, m.p.>128° C. dec. and MS: m/e=388.3 (M+H$^+$).

EXAMPLE 26

(3'aRS,6'aSR)-1-[(SR)- or -[(RS)-indan-1-yl]-5'-methyl-2'-phenyl-hexahydro-spiro[piperidine-4,1'-pyrrolo[3,4-c]pyrrole]

The mixture of (3'aRS,6'aSR)-1-[(RS)- and -[(SR)-indan-1-yl]-5'-methyl-2'-phenyl-hexahydro-spiro[piperidine-4,1'-pyrrolo[3,4-c]pyrrole]-4',6'-dione was separated by chromatography on silica gel with dichloromethane/methanol 2% into its diastereoisomers and reduced following the general procedure of example 15 to yield the title compound, MS: m/e=388.3 (M+H$^+$).

EXAMPLE 27

Mixture of (3'aSR,6'aRS)- and (3'aRS,6'aSR)-5'-ethyl-1-[(2RS,4aSR,8aRS)-decahydro-naphthalen-2-yl]-2'-phenyl-hexahydro-spiro[piperidine-4,1'-pyrrolo[3,4-c]pyrrole]fumarate (1:2.3)

The title compound, m.p.>130° C. dec. and MS: m/e=422.5 (M+H$^+$) was prepared in accordance with the general method of example 15 from the mixture of (3'aSR,6'aRS)- and (3'aRS,6'aSR)-5'-ethyl-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione.

EXAMPLE 28

Mixture of (3'aSR,6'aRS)- and (3'aRS,6'aSR)-1-[(2RS,4aSR,8aRS)-decahydro-naphthalen-2-yl]-5'-methyl-2'-phenyl-hexahydro-spiro[piperidine-4,1'-pyrrolo[3,4-c]pyrrole]fumarate (1:2.4)

The title compound, m.p.>152° C. dec. and MS: m/e=408.5 (M+H$^+$) was prepared in accordance with the general method of example 15 from the mixture of (3'aSR,6'aRS)- and (3'aRS,6'aSR)-5'-methyl-1-[(2RS,4aSR,aRS)-decahydro-naphthalen-2-yl]-2'-phenyl-hexahydro-spiro[piperidine-4,1'-pyrrolo[3,4-c]pyrrole]-4',6'-dione.

EXAMPLE 29

Mixture of (3'aSR,6'aRS)- and (3'aRS,6'aSR)-1-[(2RS,4aSR,8aRS)-decahydro-naphthalen-2-yl]-2'-phenyl-hexahydro-spiro[piperidine-4,1'-pyrrole 3,4-c]pyrrole]

The title compound, MS: m/e=394.4 (M+H$^+$) was prepared in accordance with the general method of example 15 from the mixture of (3'aSR,6'aRS)- and (3'aRS,6'aSR)-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione.

EXAMPLE 30

(3'aRS,6'aSR)-1-(2-Naphtalenylmethyl)-2'-phenyl-hexahydro-spiro[piperidine-4,1'-pyrrolo[3,4-c]pyrrole]-4',6'-dione hydrochloride A mixture of 2-bromomethylnaphtalene (1 mmol), (3'aRS,6'aSR)-2'-phenyl-hexahydro-spiro[piperidine-4,1'(2'H)-pyrrolo[3,4-c]pyrrole]-4',6'-dione (1 mmol) and sodium bicarbonate (2 mmol) in 2-butanone (10 ml) was boiled with stirring overnight. The solvent was removed in vacuo and the residue purified by chromatography on silica gel (ethylacetate) to yield the desired product (0.29 g, 97%) which was crystallized as its HCl-salt from ethylacetate to yield a colorless solid with m.p.>234° C. dec. and MS: m/e=426.4 (M+H$^+$).

EXAMPLE 31

(3'aR,6'aS)-1-Cyclononyl-5'-methyl-2'-phenyl)-hexahydro-spiro[piperine-4,1'-pyrrolo[3,4-c]pyrrole] fumarate (1:3.2)

The title compound, light red solid, m.p. 178° C. (dec.); [α]$_D^{20}$+76.4° (c=0.0772 in MeOH) and MS: m/e=396.6 (M+H$^+$) was prepared by reduction of (3'aR,6aS)-1-cyclononyl-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 89.

(3'aR,6'aS)-1-Cyclononyl-5'-methyl-2'-phenyl-hexahydro-spiro[piperidine-4,1'(2'H)-pyrrolo[3,4-c]pyrrole]-4',6'-dione was prepared from (3'aR,6'aS)-5'-methyl-1'-phenyl-hexahydro-spiro[piperidine-4,1'(2'H)-pyrrolo[3,4-c]pyrrole]-4',6'-dione and cyclononanone in accordance with the general method of example 3.

EXAMPLE 32

(3'aSR,6'aRS)-1-(2-Naphtalenylmethyl)-2'-phenyl-hexahydro-spiro[piperidine-4,1'-pyrrolo[3,4-c]pyrrole]fumarate (1:2)

Lithium aluminiumhydride (3.8 mmol) was added to a stirred solution of (3'aRS,6'aSR)-1-(2-naphtalenylmethyl)-2'-phenyl-hexahydro-spiro[piperidine-4,1'-pyrrolo[3,4-c]pyrrole]-4',6'-dione (0.5 mmol) in THF (10 ml). The mixture was stirred at room temperature for half an hour and then boiled with stirring overnight. The cooled mixture was hydrolyzed by addition of water (0.14 ml), sodium hydroxide solution (0.28 ml, 15%) and water (0.42 ml) and dried by addition of Na$_2$SO$_4$. Filtration and removal of the solvent in vacuo yielded a residue which was purified by chromatography on silica gel (dichlormethane/methanol 5%) to yield the desired product (0.11 g, 59%) as a colorless solid which was crystallized as its fumarate-salt from ethylacetate/ethanol to yield a colorless solid with m.p.>161° C. dec. and MS: m/e=398.5 (M+H$^+$).

EXAMPLE 33

(3'aSR,6'aRS)-1-(1-Naphtalenylmethyl)-2'-phenyl-hexahydro-spiro[piperidine-4,1'-pyrrolo[3,4-c]pyrrole]fumarate (1:1.5)

The title compound, m.p.192–194° C. (dec.) and MS: m/e=398.5 (M+H$^+$) was prepared in accordance with the general method of example 32 from (3'aRS,6'aSR)-1-(1-naphtalenylmethyl)-2'-phenyl-hexahydro-spiro[piperidine-4,1'-pyrrolo[3,4-c]pyrrole]-4',6'-dione.

EXAMPLE 34

(3'aSR,6'aRS)-1-[(RS)-Acenaphthen-1-yl]-5'-methyl-1'-phenyl-hexahydro-spiro[piperidine-4,1'(2'H)-pyrrolo[3,4-c]pyrrole]-4',6'-dione fumarate (1:3)

The title compound, white solid, m.p. 199° C. (dec.) and MS: m/e=452.4 (M+H$^+$) was prepared in accordance with the general method of example 5 from (RS)-1-acenaphthen-1-yl-piperidin-4-one, aniline and N-methyl-maleimide and subsequent formation of the fumarate.

EXAMPLE 35

(3'aRS,6'aSR)-1-(RS)-Acenaphthen-1-yl]-5'-methyl-1-phenyl-hexahydro-spiro[piperidine-4,1'(2'H)-pyrrolo[3,4-c]pyrrole]-4',6'-dione fumarate (1:0.72)

The title compound, white solid, m.p. 234° C.(dec.) and MS: m/e=452.4 (M+H$^+$) was prepared in accordance with the general method of example 5 from (RS)-1-acenaphthen-1-yl-piperidin-4-one, aniline and N-methyl-maleimide and subsequent formation of the fumarate.

EXAMPLE 36

(3'aRS,6'aSR)-1-[(RS-Acenaphthen-1-yl]-5'-methyl-1'-phenyl-hexahydro-spiro[piperidine-4,1'(2'H)-pyrrolo[3,4-c]pyrrole]fumarate (1:2.5)

The title compound, white solid, m.p. 180° C. (dec.) and MS: m/e=424.4 (M+H$^+$) was prepared by reduction of (3'aSR,6'aRS)-1-[(RS)-acenaphthen-1-yl]-5'-methyl-1'-phenyl-hexahydro-spiro[piperidine-4,1'(2'H)-pyrrolo[3,4-c]pyrrole]-4',6'-dione and formation of the fumarate in accordance with the general method of example 15.

EXAMPLE 37

(3'aSR,6'aRS)-1-[(RS)-Acenaphthen-1-yl]-5'-methyl-1'-phenyl-hexahydro-spiro[piperidine-4,1'(2'H)-pyrrolo[3,4-c]pyrrole]fumarate (1:2)

The title compound, light red solid, m.p. 180° C. (dec.) and MS: m/e=424.5 (M+H$^+$) was prepared by reduction of (3'aRS,6'aSR)-1-[(RS)-acenaphthen-1-yl]-5'-methyl-1'-phenyl-hexahydro-spiro[piperidine-4,1'(2'H)-pyrrolo[3,4-c]pyrrole]-4',6'-dione and formation of the fumarate in accordance with the general method of example 15.

EXAMPLE 38

(3'aRS,6'aSR)-1-[(1RS,3aRS)-2,3,3a,4,5,6-Hexahydro-1H-phenalen-1-yl]-5'-methyl-2'-phenyl-hexahydro-spiro[piperidine-4,1'(2'H)-pyrrolo[3,4-c]pyrrole]-4',6'-dione fumarate (1:2)

The title compound, white solid, m.p. 181° C. and MS: m/e=470.3 (M+H$^+$) was prepared in accordance with the general method of example 5 from (1RS,3aRS)-1-(2,3,3a,4,5,6-hexahydro-1H-phenalen-1-yl)-piperidin-4-one, aniline and N-methyl-maleimide and subsequent formation of the fumarate.

EXAMPLE 39

(3'aSR,6'aRS)-1-[(1RS,3aRS)-2,3,3a,4,5,6-Hexahydro-1H-phenalen-1-yl]-5'-methyl-2'-phenyl-hexahydro-spiro[piperidine-4,1'(2'H)-pyrrolo[3,4-c]pyrrole]-4',6'-dione fumarate (1:4)

The title compound, white solid, m.p. 219° C. and MS: m/e=470.3 (M+H$^+$) was prepared in accordance with the general method of example 5 from (1RS,3aRS)-1-(2,3,3a,4,5,6-hexahydro-1H-phenalen-1-yl)-piperidin-4-one, aniline and N-methyl-maleimide and subsequent formation of the fumarate.

EXAMPLE 40

(3'aSR,6'aRS)-1-[(1RS,3aRS)-2,3,3a,4,5,6-Hexahydro-1H-phenalen-1-yl]-5'-methyl-2'-phenyl-hexahydro-spiro[piperidine-4,1'(2'H)-pyrrolo[3,4-c]pyrrole]fumarate (1:2.35)

The title compound, light yellow solid, m.p. 158° C. (dec.) and MS: m/e=442.4 (M+H$^+$) was prepared by reduction of (3'aRS,6'aSR)-1-[(1RS,3aRS)-2,3,3a,4,5,6-hexahydro-1H-phenalen-1-yl]-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 41

(3'aRS,6'aSR)-1-[(1RS,3aRS)-2,3,3a,4,5,6-Hexahydro-1H-phenalen-1-yl]-5'-methyl-2'-phenyl-hexahydro-spiro[piperidine-4,1'(2'H)-pyrrolo[3,4-c]pyrrole]fumarate (1:2.2)

The title compound, off-white solid, m.p. 184° C. and MS: m/e=442.5 (M+H$^+$) was prepared by reduction of (3'aSR,6'aRS)-1-[(1RS,3aRS)-2,3,3a,4,5,6-hexahydro-1H-phenalen-1-yl]-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 42

(3'aRS,6'aSR)-1-Cyclooctyl-5'-methyl-2'-phenyl-hexahydro-spiro[piperidine-4,1'(2'H)-pyrrolo[3,4-c]pyrrole]-4',6'-dione fumarate (1:1)

The title compound, pale yellow solid, m.p. 213° C. (dec.) and MS: m/e=410.5 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and cyclooctanone and subsequent formation of the fumarate in accordance with the general method of example 3.

EXAMPLE 43

(3'aRS,6'aSR)-1-Cycloheptyl-5'-methyl-2'-phenyl-hexahydro-spiro[piperidine-4,1'(2'H)-pyrrolo[3,4-c]pyrrole]-4',6'-dione fumarate (1:1.17)

The title compound, white solid, m.p. 211° C. (dec.) and MS: m/e=396.3 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and cycloheptanone and subsequent formation of the fumarate in accordance with the general method of example 3.

EXAMPLE 44

(3'aRS,6'aSR)-1-Cyclooctyl-5'-methyl-2'-phenyl-hexahydro-spiro[piperidine-4,1'(2'H)-pyrrolo[3,4-c]pyrrole]fumarate (1:2.27)

The title compound, pale pink solid, m.p. 235° C. and MS: m/e=382.4 (M+H$^+$) was prepared by reduction of (3'aRS,6'aSR)-1-cyclooctyl-5'-methyl-2'-phenyl-hexahydro-spiro[piperidine-4,1'(2'H)-pyrrolo[3,4-c]pyrrole]-4',6'-dione and formation of the fumarate in accordance with the general method of example 15.

EXAMPLE 45

(3'aRS,6'aSR)-1-Cyclononyl-5'-methyl-2'-phenyl-hexahydro-spiro[piperidine-4,1'(2'H)-pyrrolo[3,4-c]pyrrole]-4',6'-dione fumarate (1:1)

The title compound, white solid, m.p. 238° C. (dec.) and MS: m/e=424.5 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and cyclononanone and subsequent formation of the fumarate in accordance with the general method of example 3.

EXAMPLE 46

(3'aRS,6'aSR)-1-Cyclononyl-5'-methyl-2'-phenyl-hexahydro-spiro[piperidine-4,1'(2'H)-pyrrolo[3,4-c]pyrrole]fumarate (1:2.25)

The title compound, white solid, m.p. 242° C. (dec.) and MS: m/e=396.4 (M+H$^+$) was prepared by reduction of (3'aRS,6'aSR)-1-cyclononyl-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 47

(3'aRS,6'aSR)-1-Cyclodecyl-5'-methyl-2'-phenyl-hexahydro-spiro[piperidine-4,1'(2'H)-pyrrolo[3,4-c]pyrrole]-4',6'-dione fumarate (1:1)

The title compound, white solid, m.p. 234° C. and MS: m/e=438.5 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and cyclodecanone and subsequent formation of the fumarate in accordance with the general method of example 3.

EXAMPLE 48

Mixture of (3'aRS,6'aSR)- and (3'aSR,6'aRS)-1-[(RS)-2,3-dihydro-1H-phenalen-1-yl]-5'-methyl-2'-phenyl-hexahydro-spiro[piperidine-4,1'(2'H)-pyrrolo[3,4-c]pyrrole]fumarate (1:3)

The title compound, pale brown solid, m.p. 173° C. and MS: m/e=438.5 (M+H$^+$) was prepared by reduction of a mixture of (3'aRS,6'aSR)- and (3'aSR,6'aRS)-1-[(RS)-2,3-dihydro-1H-phenalen-1-yl]-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 49

(3'aRS,6'aSR)-1-Cyclodecyl-5'-methyl-2'-phenyl-hexahydro-spiro[piperidine-4,1'(2'H)-pyrrolo[3,4-c]pyrrole]fumarate (1:2.2)

The title compound, pale pink solid, m.p. 240° C. and MS: m/e=410.5 (M+H$^+$) was prepared by reduction of (3'aRS,6'aSR)-1-cyclodecyl-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 50

(3'aRS,6'aSR)-1-Cycloundecyl-5'-methyl-2'-phenyl-hexahydro-spiro[piperidine-4,1'(2'H-pyrrolo[3,4-c]pyrrole]-4',6'-dione fumarate (1:1.1

The title compound, white solid, m.p. 209° C. and MS: m/e=452.5 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and cycloundecanone and subsequent formation of the fumarate in accordance with the general method of example 3.

EXAMPLE 51

(3'aRS,6'aSR)-1-Cycloheptyl-5'-methyl-2'-phenyl-hexahydro-spiro[piperidine-4,1'(2'H)-pyrrolo[3,4-c]pyrrole]fumarate (1:2.4)

The title compound, orange solid, m.p. 172° C. (dec.) and MS: m/e=368.4 (M+H$^+$) was prepared by reduction of (3'aRS,6'aSR)-1-cycloheptyl-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 52

(3'aRS,6'aSR)-1-Cycloundecyl-5'-methyl-2'-phenyl-hexahydro-spiro[piperidine-4,1'(2'H)-pyrrolo[3,4-c]pyrrole]fumarate (1:2)

The title compound, white solid, m.p. 237° C. (dec.) and MS: m/e=424.5 (M+H$^+$) was prepared by reduction of (3'aRS,6'aSR)-1-cycloundecyl-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 53

(3'aRS,6'aSR)-1-Cyclododecyl-5'-methyl-2'-phenyl-hexahydro-spiro[piperidine-4,1'(2'H)-pyrrolo[3,4-c]pyrrole]-4',6'-dione fumarate (1:1)

The title compound, white solid, m.p. 206° C. and MS: m/e=466.4 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and cyclododecanone and subsequent formation of the fumarate in accordance with the general method of example 3.

EXAMPLE 54

(3'aRS,6'aSR)-1-Cyclododecyl-5'-methyl-2'-phenyl-hexahydro-spiro[piperidine-4,1'(2'H)-pyrrolo[3,4-c]pyrrole]fumarate (1:2)

The title compound, white solid, m.p. 220° C. and MS: m/e=438.5 (M+H$^+$) was prepared by reduction of (3'aRS,6'aSR)-1-cyclododecyl-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 55

(3'aRS,6'aSR)-1-(cis-Octahydro-inden-2-yl)-5'-methyl-2'-phenyl-hexahydro-spiro[piperidine-4,1'(2'H)-pyrrolo[3,4-c]pyrrole]-4',6'-dione fumarate (1:1)

The title compound, white solid, m.p. 204° C. (dec.) and MS: m/e=422.4 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and cis-octahydro-inden-2-one and subsequent formation of the fumarate in accordance with the general method of example 3.

EXAMPLE 56

(3'aRS,6'aSR)-1-(cis-Octahydro-inden-2-yl)-5'-methyl-2'-phenyl-hexahydro-spiro[piperidine-4,1'(2'H)-pyrrolo[3,4-c]pyrrole]fumarate (1:2.2)

The title compound, orange solid, m.p. 150° C. (dec.) and MS: m/e=394.4 (M+H$^+$) was prepared by reduction of (3'aRS,6'aSR)-1-(cis-octahydro-inden-2-yl)-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 57

(3'aRS,6'aSR)-1-(Decahydro-azulen-2-yl)-5'-methyl-2'-phenyl-hexahydro-spiro[piperidine-4,1'(2'H)-pyrrolo[3,4-c]pyrrole]-4',6'-dione fumarate (1:1) (config. in azulene moiety cis and trans)

The title compound, white solid, m.p. 225° C. (dec.) and MS: m/e=436.4 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and decahydro-azulen-2-one (cis-trans-mixture) and subsequent formation of the fumarate in accordance with the general method of example 3.

EXAMPLE 58

(3'aRS,6'aSR)-1-(Decahydro-azulen-2-yl)-5'-methyl-2'-phenyl-hexahydro-spiro[piperidine-4,1'(2'H)-pyrrolo[3,4-c]pyrrole]fumarate (1:2) (config. in azulene moiety cis and trans)

The title compound, white solid, m.p. 170° C. (dec.) and MS: m/e=408.5 (M+H$^+$) was prepared by reduction of (3'aRS,6'aSR)-1-(decahydro-azulen-2-yl)-5'-methyl-2'-phenyl-hexahydro-spiro[piperidine-4,1'(2'H)-pyrrolo[3,4-c]pyrrole]-4',6'-dione (config. in azulene moiety cis and trans) and subsequent formation of the fumarate in accordance with the general method of example 15.

EXAMPLE 59

(3'aRS,6'aSR)-1-Bicyclo[3.3.1]non-9-yl-5'-cyclohexyl-2'-phenyl-hexahydro-spiro[piperidine-4,1'(2'H)-pyrrolo[3,4-c]pyrrole]-4',6'-dione fumarate (1:1.2)

The title compound, light brown solid, m.p. 241° C. and MS: m/e=422.4 (M+H$^+$) was prepared in accordance with the general method of example 5 from 1-bicyclo[3.3.1]non-9-yl-piperidin-4-one, aniline and N-methyl-maleimide and subsequent formation of the fumarate.

EXAMPLE 60

(3'aRS,6'aSR)-1-Bicyclo[3.3.1]non-9-yl-5'-cyclohexyl-2'-phenyl-hexahydro-spiro[piperidine-4,1'(2'H)-pyrrolo[3,4-c]pyrrole]fumarate (1:2.2)

The title compound, pale brown solid, m.p. 229° C. (dec.) and MS: m/e=394.4 (M+H$^+$) was prepared by reduction of (3'aRS,6'aSR)-1-bicyclo[3.3.1]non-9-yl-5'-cyclohexyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 61

(3'aRS,6'aSR)-1-(Octahydro-inden-2-yl)-5'-methyl-2'-phenyl-hexahydro-spiro[piperidine-4,1'(2'H)-pyrrolo[3,4-c]pyrrole]-4',6'-dione fumarate (1:1.7) (mixture of diastereoisomers; config. in indene moiety at C3a and C7a cis)

The title compound, light yellow solid, m.p. 160° C. (dec.) and MS: m/e=422.4 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and cis-octahydro-inden-2-one and subsequent formation of the fumarate in accordance with the general method of example 3.

EXAMPLE 62

(3'aRS,6'aSR)-1-(Octahydro-inden-2-yl)-5'-methyl-2'-phenyl-hexahydro-spiro[piperidine-4,1'(2'H)-pyrrolo[3,4-c]pyrrole]fumarate (1:1.9) (mixture of diastereoisomers; config. in indene moiety at C3a and C7a cis)

The title compound, light orange solid, m.p. 190° C. (dec.) and MS: m/e=394.4 (M+H$^+$) was prepared by reduction of (3'aRS,6'aSR)-1-(octahydro-inden-2-yl)-5'-methyl-2'-phenyl-hexahydro-spiro[piperidine-4,1'(2'H)-pyrrolo[3,4-c]pyrrole]-4',6'-dione (mixture of diastereoisomers; config. in indene moiety at C3a and C7a cis) and subsequent formation of the fumarate in accordance with the general method of example 15.

EXAMPLE 63

(3'aRS,6'aSR)-1-Bicyclo[6.2.0]dec-9-yl-5'-methyl-2'-phenyl-hexahydro-spiro[piperidine-4,1'(2'H)-pyrrolo[3,4-c]pyrrole]fumarate (1:2.52) (mixture of diastereoisomers; config. in bicyclodecane moiety at C1 and C8 cis)

The title compound, pale brown solid, m.p. 177° C. (dec.) and MS: m/e=339.4 (M+H$^+$) was prepared by reduction of (3'aRS,6'aSR)-1-bicyclo[6.2.0]dec-9-yl-5'-methyl-2'-phenyl-hexahydro-spiro[piperidine-4,1'(2'H)-pyrrolo[3,4-c]pyrrole]-4',6'-dione (mixture of diastereoisomers; config. in bicyclodecane moiety at C1 and C8 cis) and subsequent formation of the fumarate in accordance with the general method of example 15.

(3'aRS,6'aSR)-1-Bicyclo[6.2.0]dec-9-yl-5'-methyl-2'-phenyl-hexahydro-spiro[piperidine-4,1'(2'H)-pyrrolo[3,4-c]pyrrole]-4',6'-dione (mixture of diastereoisomers; config. in bicyclodecane moiety at C1 and C8 cis) was prepared from (3'aRS,6'aSR)-5'-methyl-1'-phenyl-hexahydro-spiro[piperidine-4,1'(2'H)-pyrrolo[3,4-c]pyrrole]-4',6'-dione and cis-bicyclo[6.2.0]dec-9-one in accordance with the general method of example 3.

EXAMPLE 64

Mixture of (3'aRS,6'aSR)- and 3'aSR,6'aRS)-5'-methyl-2'-phenyl-1-[(RS)-1,2,3,4-tetrahydro-naphthalen-2-yl]-hexahydro-spiro[piperidine-4,1'(2'H)-pyrrolo[3,4-c]pyrrole]-4',6'-dione fumarate (1:1)

The title compound, white solid, m.p. 206° C. and MS: m/e=430.5 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and 1,2,3,4-tetrahydro-naphthalen-2-one and subsequent formation of the fumarate in accordance with the general method of example 3.

EXAMPLE 65

Mixture of (3'aRS,6'aSR)- and (3'aRS,6'aSR)-5'-methyl-2'-phenyl-1-[(RS)-1,2,3,4-tetrahydro-naphthalen-2-yl]-hexahydro-spiro[piperidine-4,1'(2'H)-pyrrolo[3,4-c]pyrrole]fumarate (1:2.2)

The title compound, white solid, m.p. 166° C. (dec.) and MS: m/e=402.5 (M+H$^+$) was prepared by reduction of a mixture of (3'aRS,6'aSR)- and (3'aSR,6'aRS)-5'-methyl-2'-phenyl-1-[(RS)-1,2,3,4-tetrahydro-naphthalen-2-yl]-hexahydro-spiro[piperidine-4,1'(2'H)-pyrrolo[3,4-c]pyrrole]-4',6'-dione and subsequent formation of the fumarate in accordance with the general method of example 15.

EXAMPLE 66

(3'aRS,6'aSR)-1-(5-Isopropyl-2-methyl-bicyclof3.1.0]hex-3-yl)-5'-methyl-2'-phenyl-hexahydro-spiro[piperidine-4,1'(2'H)-pyrrolo[3,4-c]pyrrole]-4',6'-dione fumarate (1:3) (mixture of diastereoisomers)

The title compound, light yellow solid, m.p. 197° C. (dec.) and MS: m/e=436.5 (M+H$^+$) was prepared from (3'aRS,6'aSR)-5'-methyl-1'-phenyl-hexahydro-spiro[piperidine-4,1'(2'H)-pyrrolo[3,4-c]pyrrole]-4',6'-dione and 5-isopropyl-2-methyl-bicyclo[3.1.0]hex-3-one (mixture of diastereoisomers) and subsequent formation of the fumarate in accordance with the general method of example 3.

EXAMPLE 67

(3'aRS,6'aSR)-1-(5-Isopropyl-2-methyl-bicyclo[3.1.0hex-3-yl)-5'-methyl-2'-phenyl-hexahydro-spiro[piperidine-4,1'(2'H)-pyrrolo[3,4-c]pyrrole]fumarate (1:2.2) (mixture of diastereoisomers)

The title compound, orange solid, m.p. 182° C. (dec.) and MS: m/e=408.5 (M+H$^+$) was prepared by reduction of (3'aRS,6'aSR)-1-(5-isopropyl-2-methyl-bicyclo[3.1.0]hex-3-yl)-5'-methyl-2'-phenyl-hexahydro-spiro[piperidine-4,1'(2'H)-pyrrolo[3,4-c]pyrrole]-4',6'-dione (mixture of diastereoisomers) and subsequent formation of the fumarate in accordance with the general method of example 15.

EXAMPLE 68

(3'aRS,6'aSR)-1-Cyclodecyl-5'-ethyl-2'-phenyl-hexahydro-spiro[piperidine-4,1'(2'H)-pyrrolo[3,4-c]pyrrole]-4',6'-dione fumarate (1:1)

The title compound, white solid, m.p. 235° C. and MS: m/e=452.5 (M+H$^+$) was prepared from (3'aRS,6'aSR)-5'- ethyl-1'-phenyl-hexahydro-spiro[piperidine-4,1'(2'H)-pyrrolo[3,4-c]pyrrole]-4',6'-dione and cyclodecanone and subsequent formation of the fumarate in accordance with the general method of example 3.

EXAMPLE 69

(3'aRS,6'aSR)-1-Cyclodecyl-5'-ethyl-2'-phenyl-hexahydro-spiro[piperidine-4,1'(2'H)-pyrrolo[3,4-c] pyrrole]fumarate (1:2.2)

The title compound, light orange solid, m.p. 232° C. (dec.) and MS: m/e=424.5 (M+H$^+$) was prepared by reduction of (3'aRS,6'aSR)-1-cyclodecyl-5'-ethyl-2'-phenyl-hexahydro-spiro[piperidine-4,1'(2'H)-pyrrolo[3,4-c] pyrrole]-4',6'-dione and subsequent formation of the fumarate in accordance with the general method of example 15.

EXAMPLE 70

(3'aRS,6'aSR)-1-Cyclononyl-5'-ethyl-2'-phenyl-hexahydro-spiro[piperidine-4,1'(2'H)-pyrrolo[3,4-c] pyrrole]-4',6'-dione fumarate (1:1.2)

The title compound, white solid, m.p. 238° C. (dec.) and MS: m/e=438.5 (M+H$^+$) was prepared from (3'aRS,6'aSR)-5'-ethyl-1'-phenyl-hexahydro-spiro[piperidine-4,1'(2'H)-pyrrolo[3,4-c]pyrrole]-4',6'-dione and cyclononanone and subsequent formation of the fumarate in accordance with the general method of example 3.

EXAMPLE 71

(3'aRS,6'aSR)-1-Cyclononyl-5'-ethyl-2'-phenyl-hexahydro-spiro[piperidine-4,1'(2'H)-pyrrolo[3,4-c] pyrrole]fumarate (1:2)

The title compound, orange solid, m.p. 229° C. (dec.) and MS: m/e=410.5 (M+H$^+$) was prepared by reduction of (3'aRS,6'aSR)-1-cyclononyl-5'-ethyl-2'-phenyl-hexahydro-spiro[piperidine-4,1'(2'H)-pyrrolo[3,4-c]pyrrole]-4',6'-dione and subsequent formation of the fumarate in accordance with the general method of example 15.

EXAMPLE 72

(3'aRS,6'aSR)-5'-Cyclohexyl-1-cyclononyl-2'-phenyl-hexahydro-spiro[piperidine-4,1'(2'H)-pyrrolo [3,4-c]pyrrole]fumarate (1:2.2)

The title compound, white solid, m.p. 164° C. (dec.) and MS: m/e=378.5 (M+H$^+$) was prepared by reduction of (3'aRS,6'aSR)-5'-cyclohexyl-1-cyclononyl-2'-phenyl-hexahydro-spiro[piperidine-4,1'(2'H)-pyrrolo[3,4-c] pyrrole]-4',6'dione and subsequent formation of the fumarate in accordance with the general method of example 15.

(3'aRS,6'aSR)-5'-cyclohexyl-1-cyclononyl-2'-phenyl-hexahydro-spiro[piperidine-4,1'(2'H)-pyrrolo[3,4-c] pyrrole]-4',6'-dione was prepared in accordance with the general method of example 5 from N-cyclononyl-piperidin-4-one, aniline and N-cyclohexyl-maleimide and subsequent formation of the fumarate.

EXAMPLE 73

(3'aS,6'aR)-1-[R)-acenaphthen-1-yl]-2'-metyl-2'-phenyl-hexahydro-spiro[piperidine-4,1'(2'H)-pyrrolo [3,4-c]pyrrole]fumarate (1)

The title compound, light red solid, m.p. 180° C. (dec.); [α]$_D^{20}$=−48.5° (c=0.1030 in MeOH) and MS: m/e=424.4 (M+H$^+$) was prepared by reduction of (3'aS,6'aR)-1-[(R)-acenaphthen-1-yl]-5'-methyl-1'-phenyl-hexahydro-spiro [piperidine-4,1'(2'H)-pyrrolo[3,4-c]pyrrole]-4',6'-dione and formation of the fumarate in accordance with the general method of example 15.

(3'aS,6'aR)-1-[(R)-Acenaphthen-1-yl]-5'-methyl-1'-phenyl-hexahydro-spiro[piperidine-4,1'(2'H)-pyrrolo[3,4-c] pyrrole]-4',6'-dione was prepared in accordance with the general method of example 5 from (R)-1-acenaphthen-1-yl-piperidin-4-one, aniline and N-methyl-maleimide.

EXAMPLE 74

(3'aR,6'aS)-1-[R)-acenaphthen-1-yl -2'-methyl-2'-phenyl-hexahydro-spiro[piperidine-4,1'(2'H)-pyrrolo [3,4-c]pyrrole]fumarate (1:2.6)

The title compound, light red solid, m.p. 150° C. (dec.); [α]$_D^{20}$+41.3° (c 0.1091 in MeOH) and MS: m/e=424.4 (M+H$^+$) was prepared by reduction of (3'aR,6'aS)-1-[(R)-acenaphthen-1-yl]-5'-methyl-1'-phenyl-hexahydro-spiro [piperidine-4,1'(2'H)-pyrrolo[3,4-c]pyrrole]-4',6'-dione and formation of the fumarate in accordance with the general method of example 15.

(3'aR,6'aS)-1-[(R)-Acenaphthen-1-yl]-5'-methyl-1'-phenyl-hexahydro-spiro[piperidine-4,1'(2'H)-pyrrolo[3,4-c] pyrrole]-4',6'-dione was prepared in accordance with the general method of example 5 from (R)-1-acenaphthen-1-yl-piperidin-4-one, aniline and N-methyl-maleimide.

EXAMPLE 75

(3'aRS,6'aSR)-5'-Benzyl-1-cyclodecyl-2'-phenyl-hexahydro-spiro[piperidine-4,1'-pyrrolo[3,4-c] pyrrole]-4',6'-dione fumarate (1:1)

The title compound, light yellow solid, m.p. 174° C. and MS: m/e=514.4 (M+H$^+$) was prepared in accordance with the general method of example 5 from 1-cyclodecyl-piperidin-4-one, aniline and N-benzyl-maleimide and subsequent formation of the fumarate.

EXAMPLE 76

(3'aRS,6'aSR)-5'-Benzyl-1-cyclodecyl-2'-phenyl-hexahydro-spiro[piperidine-4,1'-pyrrolo[3,4-c] pyrrole]fumarate (1:1)

The title compound, white solid, m.p. 215° C. (dec.) and MS: m/e=486.5 (M+H$^+$) was prepared by reduction of (3'RS, SR)-5'-benzyl-1-cyclodecyl-2'-phenyl-hexahydro-spiro[piperidine-4,1'-pyrrolo[3,4-c]pyrrole]-4',6'-dione and subsequent formation of the fumarate in accordance with the general method of example 15.

EXAMPLE 77

(3'aRS,6'aSR)-1-(cis-4-Isopropyl-cyclohexyl)-5'-methyl-2'-phenyl-hexahydro-spiro[piperidine-4,1'-pyrrolo[3,4-c]pyrrole]-4',6'-dione hydrochloride (1:1.6)

cis-[1-(4-Isopropyl-cyclohexyl)-piperidin-4-ylidene] phenyl-amine (2.00 g, 6.70 mmol) was dissolved in 1,2-dimethoxy ethane (35 ml) and treated at 0° C. with (trimethylsilyl)methyl trifluoromethane sulfonate (1.90 g, 8.04 mmol). After stirring at room temperature for 2 h N-methyl maleimide (2.10 g, 18.0 mmol) followed by caesium fluoride (1.2 g, 8.04 mmol) were added and the reaction mixture was stirred at room temperature for 40 h. The desired product (960 mg, 34%) precipitated from the reaction mixture, m.p. 184° C. (basic compound) and MS: m/e=424.5 (M+H⁺)⁺. The HCl salt was optained by treating an etheral solution of the free base with an excess HCl in diethyl ether.

EXAMPLE 78

(3'aRS,6'aSR)-1-(cis-4-Isopropyl-cyclohexyl)-2',5'-diphenyl-hexahydro-spiro[piperidine-4,1'-pyrrolo[3,4-c]pyrrole]-4',6'-dione fumarate (1:0.9)

The title compound, m.p. 155° C. and MS: m/e=468.4 (M+H⁺) was prepared in accordance with the general method of example 77 from cis-[1-(4-isopropyl-cyclohexyl)-piperidin-4-ylidene]phenyl-amine and N-phenyl maleimide.

EXAMPLE 79

(3'aRS,6'aSR)-1-(cis-4-Isopropyl-cyclohexyl)-2'-phenyl-hexahydro-spiro[piperidine-4,1'-pyrrolo[3,4-c]pyrrole]-4',6'-dione fumarate (1:0.9)

The title compound, dec>200° C. and MS: m/e=410.5 (M+H⁺) was prepared in accordance with the general method of example 77 from cis-[1-(4-isopropyl-cyclohexyl)-piperidin-4-ylidene]phenyl-amine and maleimide.

EXAMPLE 80

(3'aRS,6'aSR)-1-(cis-4-Isopropyl-cyclohexyl)-5'-ethyl-2'-phenyl-hexahydro-spiro[piperidine-4,1'-pyrrolo[3,4-c]pyrrole]-4',6'-dione fumarate (1:1.15)

The title compound, m.p.214° C. and MS: m/e=438.4 (M+H⁺) was prepared in accordance with the general method of example 77 from cis-[1-(4-isopropyl-cyclohexyl-piperidin-4-ylidene]phenyl-amine and N-ethyl maleimide.

EXAMPLE 81

(3'aRS,6'aSR)-1-(cis-4-Isopropyl-cyclohexyl)-5'-cyclopropylethyl -2'-phenyl-hexahydro-spiro[piperidine-4,1'-pyrrolo[3,4-c]pyrrole4',6'-dione fumarate (1:1)

1.0 g (2.44 mmol) (3'aRS,6'aSR)-1-(cis-4-Isopropyl-cyclohexyl)-2'-phenyl-hexahydro-spiro[piperidine-4,1'-pyrrolo[3,4-c]pyrrole]-4',6'-dione was dissolved in 15 mL dry tetrahydrofuran. Triphenylphosphine (640 mg, 2.44 mmol), hydroxymethyl cyclopropane (1176 mg, 2.44 mmol) and diethyl azodicarboxylate (425 mg, 2.44 mmol) in 5 mL tetrahydrofuran were added subsequently and the mixture was stirred at room temperature for 24 h. The tetrahydrofuran was evaporated and the residue purified by column chromatography (hexane/ethyl acetate/triethylamine 40:10:1). The desired product was obtained as a yellow solid (725 mg, 64%) which was precipitated as its fumarate salt from diethylether, m.p. 184° C. (salt) and MS: m/e=464.4 (M+H⁺).

EXAMPLE 82

(3aRS,6'aSR)-1-(cis-4-Isopropyl-cyclohexyl)-5'-cyclohexyl-2'-phenyl-hexahydro-spiro[piperidined-4,1'-pyrrolo[3,4-c]pyrrole]-4',6'-dione fumarate (1:1.1)

The title compound, dec>195° C. and MS: m/e=492.4 (M+H⁺) was prepared in accordance with the general method of example 81 from (3'aR,6'aSR)-1-(cis-4-isopropyl-cyclohexyl)-2'-phenyl-hexahydro-spiro[piperidine-4,1'-pyrrolo[3,4-c]pyrrole]-4',6'-dione and cyclohexanol.

EXAMPLE 83

(3'aRS,6'aSR)-1-(cis-4-Isopropyl-cyclohexyl)-5'-benzyl-2'-phenyl-hexahydro-spiro[piperidine-4,1'-pyrrolo[3,4-c]pyrrole]-4',6'-dione fumarate (1:1)

The title compound, m.p. 103° C. and MS: m/e=492.4 (M+H⁺) was prepared in accordance with the general method of example 81 from (3'aRS,6'aSR)-1-(cis-4-isopropyl-cyclohexyl)-2'-phenyl-hexahydro-spiro[piperidine-4,1'-pyrrolo[3,4-c]pyrrole]-4',6'-dione and benzyl alcohol.

EXAMPLE 84

(3'aRS,6'aSR)-1-(cis-4-Isopropyl-cyclohexyl)-5'-butyl-2'-phenyl-hexahydro-spiro[piperidine-4,1'-pyrrolo[3,4-c]pyrrole]-4',6'-dione frmarate (1:1)

The title compound, m.p. 184° C. and MS: m/e=466.4 (M+H⁺) was prepared in accordance with the general method of example 81 from (3'aRS,6'aSR)-1-(cis-4-isopropyl-cyclohexyl)-2'-phenyl-hexahydro-spiro[piperidine-4,1'-pyrrolo[3,4-c]pyrrole]-4',6'-dione and n-butanol.

EXAMPLE 85

(3'aRS,6'aSR)-1-(cis-4-Isopropyl-cyclohexyl)-2'-phenyl-5'-(tetrahydro-furan-3-yl)-hexahydro-spiro[piperidine-4,1'-pyrrolo[3,4-c]pyrrole]-4',6-dione fumarate (1:1)

The title compound, m.p. 188–190° C. and MS: m/e= 480.5 (M+H⁺) was prepared in accordance with the general method of example 81 from (3'aRS,6'aSR)-1-(cis-4-isopropyl-cyclohexyl)-2'-phenyl-hexahydro-spiro[piperidine-4,1'-pyrrolo[3,4-c]pyrrole]-4',6'-dione and rac-3-hydroxy-tetmhydrofuran.

EXAMPLE 86

(3'aRS,6'aSR)-5'(2-Benzyloxy-ethyl)-1-(cis-4-isopropyl-cyclohexyl)-2'-phenyl-hexahydro-spiro[piperidine-4,1'-pyrrolo[3,4-c]pyrrole]-4',6'-dione fumarate (1:1)

The title compound, m.p. 155° C. and MS: m/e=544.3 (M+H⁺) was prepared in accordance with the general method of example 81 from (3'aRS,6'aSR)-1-(cis-4-isopropyl-cyclohexyl)-2'-phenyl-hexahydro-spiro[piperidine-4,1'-pyrrolo[3,4-c]pyrrole]-4',6'-dione and 2-benzyloxy ethanol.

EXAMPLE 87

(3'aRS,6'aSR)-4-(cis-4-Isopropyl-cyclohexyl)-5'-(3-methyl-oxetan-3-ylmethyl)-2'-phenyl-hexahydro-spiro[piperidine-4,1'(2'H)-pyrrolo[3,4-c]pyrrole-4',6'-dione fumarate (1:1)

The title compound, m.p. 171° C. and MS: m/e=494.4 (M+H⁺) was prepared in accordance with the general method of example 81 from (3'aRS,6'aSR)-1-(cis-4-isopropyl-cyclohexyl)-2'-phenyl-hexahydro-spiro

[piperidine-4,1'-pyrrolo[3,4-c]pyrrole]-4',6'-dione and 3-hydroxy-methyl-3-methyl-oxetan.

EXAMPLE 88

(3'aRS,6'aSR)-1-(cis-4-Isopropyl-cyclohexyl)-5'-(2-morpholin-4-yl-ethyl)-2'-phenyl-hexahydro-spiro[piperidine-4,1'-pyrrolo[3,4-c]pyrrole]-4',6'-dione fumarate (1:2.2)

The title compound, m.p. 170–175° C. and MS: m/e=523.3 (M+H$^+$) was prepared in accordance with the general method of example 81 from (3'aRS,6'aSR)-1-(cis-4-isopropyl-cyclohexyl)-2'-phenyl-hexahydro-spiro[piperidine-4,1'-pyrrolo[3,4-c]pyrrole]-4',6'-dione and N-(2-hydroxyethyl)-morpholine.

EXAMPLE 89

(3'aRS,6'aSR)1-(cis-4-Isopropyl-cyclohexyl)-5'-methyl-2'-phenyl-hexahydro-spiro[piperidine-4,1'-pyrrolo[3,4-c]pyrrole]fumarate (1:1.5)

(3'aRS,6'aSR)1-(cis-4-Isopropyl-cyclohexyl)-5'-methyl-2'-phenyl-hexahydro-spiro[piperidine-4,1'-pyrrolo[3,4-c]pyrrol]-4',6'-dione (212 mg, 0.5 mmol) was dissolved in methylene chloride (4 ml) and diethylether (5 ml) and lithium aluminium hydride (55 mg, 1.45 mmol) was added. The reaction mixture was stirred at room temperature for 1.5 h. The reaction mixture was then subsequently treated with 0.05 ml water, 0.05 ml 15% sodium hydroxide solution and 0.15 ml water. The solid material was filtered off and the filtrate was evaporated. Column chromatography (hexane/ethyl acetate/triethylamine 10:10:1) of the residue gave the desired product (140 mg, 70%) which was precipitated as its fumarate salt from a mixture of methanol and diethylether, dec.>165° C., MS: m/e=396.4 (M+H$^+$).

EXAMPLE 90

(3'aRS,6'aSR)1-(cis-4-Isopropyl-cyclohexyl)-5'-ethyl-2'-phenyl-hexahydro-spiro[piperidine-4,1'-pyrrolo[3,4-c]pyrrole]fumarate (1:1.5)

The title compound, dec>200° C. and MS: m/e=410.5 (M+H$^+$) was prepared in accordance with the general method of example 89 from (3'aRS,6'aSR)1-(cis-4-isopropyl-cyclohexyl)-5'-ethyl-2'-phenyl-hexahydro-spiro[piperidine-4,1'-pyrrolo[3,4-c]pyrrol]-4',6'-dione.

EXAMPLE 91

(3'aRS,6'aSR)1-(cis-4-Isopropyl-cyclohexyl)-2',5'-diphenyl-hexahydro-spiro[piperidine-4,1'-pyrrolo[3,4-c]pyrrole]fumarate (1:1.5)

The title compound, dec>255° C. and MS: m/e=410.5 (M+H$^+$) was prepared in accordance with the general method of example 89 from (3'aRS,6'aSR)1-(cis-4-isopropyl-cyclohexyl)-2',5'-diphenyl-hexahydro-spiro[piperidine-4,1'-pyrrolo[3,4-c]pyrrol]-4',6'-dione.

EXAMPLE 92

(3'aRS,6'aRS)-1-(cis-4-Isopropyl-cyclohexyl)-5'-(3-methyl-oxetan-3-ylmethyl)-2'-phenyl-hexahydro-spiro[piperidine-4,1'-pyrrolo[3,4-c]pyrrole]fumarate (1:1)

The title compound, m.p. 213–215° C. and MS: m/e=466.4 (M+H$^+$) was prepared in accordance with the general method of example 89 from (3'aRS,6'aSR)-4-(cis-4-isopropyl-cyclohexyl)-5'-(3-methyl-oxetan-3-ylmethyl)-2'-phenyl-hexahydro-spiro[piperidine-4,1'(2'H)-pyrrolo[3,4-c]pyrrole-4',6'-dione.

EXAMPLE 93

(3'aRS,6'aRS)-5'-(2-Benzyloxy-ethyl)-1-(cis-4-isopropyl-cyclohexyl)-2'-phenyl-hexahydro-spiro[piperidine-4,1'-pyrrolo[3,4-c]pyrrole]fumarate (1:2.05)

The title compound, m.p. 168–170° C. and MS: m/e=516.4 (M+H$^+$) was prepared in accordance with the general method of example 89 (3'aRS,6'aSR)-5'(2-benzyloxy-ethyl)-1-(cis-4-isopropyl-cyclohexyl)-2'-phenyl-hexahydro-spiro[piperidine-4,1'-pyrrolo[3,4-c]pyrrole]-4',6'-dione.

EXAMPLE 94

(3'aRS,6'aSR)-4-(cis-4-Isopropyl-cyclohexyl)-5'-benzyl-2'-phenyl-hexahydro-spiro[piperidine-4,1'(2'H)-pyrrolo[3,4-c]pyrrole]hydrochloride (1:2.3)

The title compound, dec>190° C. and MS: m/e=427.4 (M+H$^+$) was prepared in accordance with the general method of example 89 (3'aRS,6'aSR)-1-(cis-4-isopropyl-cyclohexyl)-5'-benzyl-2-phenyl-hexahydro-spiro[piperidine-4,1'-pyrrolo[3,4-c]pyrrole]-4',6'-dione.

EXAMPLE 95

(3'aRS,6'aRS)-1-(cis-4-Isopropyl-cyclohexyl)-2'-phenyl-5'-(tetrahydro-furan-3-yl)-hexahydro-spiro[piperidine-4,1'-pyrrolo[3,4-c]pyrrole]fumarate (1:2)

The title compound, dec>205° C. and MS: m/e=452.6 (M+H$^+$) was prepared in accordance with the general method of example 89 (3'aRS,6'aSR)-1-(cis-4-isopropyl-cyclohexyl)-2'-phenyl-5'-(tetrahydro-furan-3-yl)-hexahydro-spiro[piperidine-4,1'-pyrrolo[3,4-c]pyrrole]-4',6'-dione.

EXAMPLE 96

(3'aRS,6'aSR)-4-(cis-4-Isopropyl-cyclohexyl)-5'-cyclohexyl-2'-phenyl-hexahydro-spiro[piperidine-4,1'(2'H)-pyrrolo[3,4-c]pyrrole]fumarate (1:2.18)

The title compound, dec>190° C. and MS: m/e=464.5 (M+H$^+$) was prepared in accordance with the general method of example 89 (3'aRS,6'aSR)-1-(cis-4-isopropyl-cyclohexyl)-5'-cyclohexyl-2'-phenyl-hexahydro-spiro[piperidine-4,1'-pyrrolo[3,4-c]pyrrole]-4',6'-dione.

EXAMPLE 97

(3'aRS,6'aSR)-4-(cis-4-Isopropyl-cyclohexyl)-5'-butyl-2'-phenyl-hexahydro-spiro[piperidine-4,1'(2'H)-pyrrolo[3,4-c]pyrrole]fumarate (1:2.2)

The title compound, dec.>220° C. and MS: m/e=438.5 (M+H$^+$) was prepared in accordance with the general method of example 89 (3'aRS,6'aSR)-1-(cis-4-isopropyl-cyclohexyl)-5'-butyl-2'-phenyl-hexahydro-spiro[piperidine-4,1'-pyrrolo[3,4-c]pyrrole]-4',6'-dione.

EXAMPLE 98

(3'aRS,6'aSR)-4-(cis-4-Isopropyl-cyclohexyl)-5'-cyclopropylmethyl-2'-phenyl-hexahydro-spiro[piperidine-4,1'(2'H)-pyrrolo[3,4-c]pyrrole]fumarate (1:1.8)

The title compound, dec>215° C. and MS: m/e=436.5 (M+H$^+$) was prepared in accordance with the general method of example 89 (3'aRS,6'aSR)-1-(cis-4-isopropyl-cyclohexyl)-5'-cyclopropylmethyl-2'-phenyl-hexahydro-spiro[piperidine-4,1'-pyrrolo[3,4-c]pyrrole]-4',6'-dione.

EXAMPLE 99

(3'aS,6'aR)1-(cis-4-Isopropyl-cyclohexyl)-5'-methyl-2'-phenyl-hexahydro-spiro[piperidine-4,1'-pyrrolo[3,4-c]pyrrole]fumarate (1:2.1)

3.04 g (7.68 mmol) of the racemic mixture (3'aSR,6'aRS) 1-(cis-4-isopropyl-cyclohexyl)-5'-methyl-2'-phenyl-hexahydro-spiro[piperidine-4,1'-pyrrolo[3,4-c]pyrrole] were dissolved in 70 ml methanol and water (95:5) and 1.65 g (4.61 mmol) (−)-O,O-dibenzoyl-L-tartaric acid were added. The mixture was refluxed until complete solution and the solvent was partly distilled off until the first precipitate occured. Slow cooling resulted in the precipitation of 1.3 g (22%) crystals. The enantiomeric excess was determined by chiral HPLC to be 98.6%, $[\alpha]_{589}^{20}$=+101.08, $[\alpha]_{546}^{20}$=+124.22 (fumarate salt, c=0.9982, methanol).

EXAMPLE 100

(3'aR,6'aS)1-(cis-4-Isopropyl-cyclohexyl)-5'-methyl-2'-phenyl-hexahydro-spiro[piperidine-4,1'-pyrrolo[3,4-c]pyrrole]fumarate (1:1.85)

The title compound was prepared in accordance with the method of example 99 from the racemic mixture (3'aSR,6'aRS)1-(cis-4-isopropyl-cyclohexyl)-5'-methyl-2'-phenyl-hexahydro-spiro[piperidine-4,1'-pyrrolo[3,4-c]pyrrole] and (+)-O,O-dibenzoyl-D-tartaric acid. The enantiomeric excess was determined by chiral HPLC to be 98.4%, $[\alpha]_{589}^{20}$=−112.49, $[\alpha]_{546}^{20}$=−137.91 (fumarate salt, c=0.7947, methanol).

EXAMPLE 101

(3'aRS,4'RS,6'aSR)- and (3'aRS,4'SR,6'aSR)-4'-Hydroxy-1-(cis-4-isopropyl-cyclohexyl)-5'-methyl-2'-phenyl-hexahydro-spiro[piperidine-4,1'-pyrrolo[3,4-c]pyrrole]-6'-one hydrochloride (1:1), mixture of diastereomers (3'aRS,6'aSR)1-(cis-4-Isopropyl-cyclohexyl)-5'-methyl-2'-phenyl-hexahydro-spiro[piperidine-4,1'-pyrrolo[3,4-c]pyrrole]-4',6'-dione (846 mg, 2.0 mmol) was dissolved in isopropanol (12 ml) and water (2 ml) and sodium borohydride (515 mg, 13.6 mmol) was added. The reaction mixture was stirred at room temperature for 16 h. The solid material was filtered off and the filtrate was evaporated. Column chromatography (methylene chloride/methanol/ammonium hydroxide 250:10:1) of the residue gave the desired product (450 mg, 53%) as a colourless oil which was precipitated as its HCl salt from a mixture of methanol and diethylether, dec.>115° C., MS: m/e=426.5 (M+H⁺).

EXAMPLE 102

(3'aRS,6'aSR)-1-(cis-4-Isopropyl-cyclohexyl)-5'-methyl-2'-phenyl-hexahydro-spiro[piperidine-4,1'-pyrrolo[3,4-c]pyrrole]-6'-one (3'aRS,4'RS,6'aSR)- and (3'aRS,4'SR,6'aSR)-4'-Hydroxy-1-(cis-4-isopropyl-cyclohexyl)-5'-methyl-2'-phenyl-hexahydro-spiro[piperidine-4,1'-pyrrolo[3,4-c]pyrrole]-6'-one (mixture of diastereomers, 3.02 g, 7.10 mmol) was dissolved in 30 mL dichloromethane and 8.25 g (71.0 mmol) triethylsilane and 40.5 g (355 mmol) trifluoro acetic acid were added subsequently. After stirring at room temperature for 3 days the reaction mixture was poured into 100 mL 2N sodium carbonate solution and extracted with dichloromethane. The organic phase was dried with MgSO₄ and concentrated. Chromatography on silica gel (hexane/ethyl acetate/triethylamine 10:10:1) gave 2.6 g (89%) of the desired product as a white solid, m.p. 153° C., MS: m/e=410.6 (M+H⁺).

EXAMPLE 103

(3'aRS,4'RS,6'aSR)1-(cis-4-Isopropyl-cyclohexyl)-4',5'-dimethyl-2'-phenyl-hexahydro-spiro[piperidine-4,1'-pyrrolo[3,4-c]pyrrole]-6'-one and (3'aRS,4lSR,6'aSR)-(cis-4-Isopropyl-cyclohexyl)-4',5'-dimethyl-2'-phenyl-hexahydro-spiro[piperidine-4,1'-pyrrolo[3,4-c]pyrrole]-6'-one (3'aRS,6'aSR)-1-(cis-4-Isopropyl-cyclohexyl)-2'-phenyl-hexahydro-spiro[piperidine-4,1'-pyrrolo[3,4-c]pyrrole]-4',6'-dione (1.00 g, 2.36 mmol) were dissolved in 25 mL tetrahydrofuran and treated at room temperature with methyl magnesium chloride solution (1.73 mL, 3M in tetrahydrofuran). After stirring for 16 h at room temperature 10 mL 1N HCl and 20 mL 1N NaOH solution were added and then extracted with dichloromethane. The organic phase was dried with MgSO₄ and concentrated. The crude product was dissolved in 25 mL methanol and sodium cyanoborohydride (148 mg, 2.36 mmol) and 3 drops methylene red (indicator) were added. Trifluoro acetic acid was added dropwise until the reaction mixture turned redish and stirring was continued for 2 hours during which further addition of trifluoro acetic acid was necessary (mixture had to be red). 1N NaOH solution was added until pH 8–9 and methanol was evaporated. The residue was taken up in dichloromethane and extracted with water. The organic phase was dried with MgSO₄ and concentrated. Chromatography on silica gel (hexane/ethyl acetate/triethylamine 50:10:1) gave 36 mg (3.6%) pure (3'aRS,4TRS,6'aSR)1-(cis-4-isopropyl-cyclohexyl)-4',5'-dimethyl-2'-phenyl-hexahydro-spiro [piperidine-4,1'-pyrrolo[3,4-c]pyrrole]-6'-one, dec>180° C., MS: m/e=424.5 (M+H⁺) and 207 mg (21%) pure (3'aRS, 4'SR,6'aSR)1-(cis-4-isopropyl-cyclohexyl)-4',5'-dimethyl-2'-phenyl-hexahydro-spiro[piperidine-4,1'-pyrrolo[3,4-c]pyrrole]-6'-one, m.p. 135° C., MS: m/e=424.5 (M+H⁺).

EXAMPLE 104

(3'aRS,4'RS,6'aSR)1-(cis-4-Isopropyl-cyclohexyl)-5'-methyl-2',4'-diphenyl-hexahydro-spiro[piperidine-4,1'-pyrrolo[3,4-c]pyrrole]-6'-one fumarate (1:1)

The title compound, dec>203° C. and MS: m/e=486.6 (M+H⁺) was prepared in accordance with the general method of example 103 from (3'aRS,6'aSR)-1-(cis-4-isopropyl-cyclohexyl)-2'-phenyl-hexahydro-spiro [piperidine-4,1'-pyrrolo[3,4-c]pyrrole]-4',6'-dione and phenyl magnesium chloride.

EXAMPLE 105

(3'aRS,4'SR,6'aRS)-1-(cis-4-Isopropyl-cyclohexyl)-4',5'-dimethyl-2'-phenyl-hexahydro-spiro[piperidine-4,1'-pyrrolo[3,4-c]pyrrole]fumarate (1:4)

The title compound, dec>132° C. and MS: m/e=410.5 (M+H⁺) was prepared in accordance with the general method of example 89 from (3'aRS,4'SR,6'aSR)1-(cis-4-isopropyl-cyclohexyl)-4',5'-dimethyl-2'-phenyl-hexahydro-spiro[piperidine-4,1'-pyrrolo[3,4-c]pyrrole]-6'-one.

EXAMPLE 106

(3'aRS,6'aSR)-4-(cis-4-Isopropyl-cyclohexyl)-2'-phenyl-hexahydro-spiro[piperidine-4,1'(2'H)-pyrrolo[3,4-c]pyrrole]

(3'aRS,6'aSR)-4-(cis-4-Isopropyl-cyclohexyl)-5'-benzyl-2'-phenyl-hexahydro-spiro[piperidine-4,1'(2'H)-pyrrolo[3,4-c]pyrrole] (5.5 g, 11.6 mmol) and 10% Pd/C (0.67 g) in 67 mL methanol and 6.7 mL glacial acetic acid were hydrogenated with 1 atm hydrogen for 20 hours. Pd/C was filtered off and the methanol and acetic acid coevaporated with toluene. Chromatography (dichloromethane/methanol/ammonium hydroxid 140:10:1) of the residue gave 3.77 g (85%) of the desired product, m.p. 127° C. and MS: m/e=382.4 (M+H$^+$).

EXAMPLE 107

(3'aRS,6'aRS)-1-(cis-4-Isopropyl-cyclohexyl)-5'-(2-hydroxy-ethyl)-2'-phenyl-hexahydro-spiro[piperidine-4,1'-pyrrolo[3,4-c]pyrrole]fumarate (1:1)

(3'aRS,6'aRS)-5'-(2-Benzyloxy-ethyl)-1-(cis-4-isopropyl-cyclohexyl)-2'-phenyl-hexahydro-spiro[piperidine-4,1'-pyrrolo[3,4-c]pyrrole] (430 mg, 0.833 mmol) and 10% Pd/C (50 mg) in 10 mL methanol and 5 mL 2.7N HCl/MeOH were hydrogenated with 1 atm hydrogen for 20 hours. Pd/C was filtered off and the methanol was evaporated. The residue was taken up in ethyl acetate and extracted with 2N NaOH solution. The organic phase was dried with MgSO$_4$ and concentrated. Column chromatography (dichloro methane/methanol/ammonium hydroxid 140:10:1) gave 170 mg (48%) of the desired product, which was precipitated as its fumarate salt from methanol and diethyl ether, m.p. 194° C. and MS: m/e=426.6 (M+H$^+$).

EXAMPLE 108

(3'aRS,6'aRS)-1-(cis-4-Isopropyl-cyclohexyl)-5'-methylsulfonyl-2'-phenyl-hexahydro-spiro[piperidine-4,1'-pyrrolo[3,4-c]pyrrole]fumarate (1:1)

(3'aRS,6'aSR)-4-(cis-4-Isopropyl-cyclohexyl)-2'-phenyl-hexahydro-spiro[piperidine-4,1'(2'H)-pyrrolo[3,4-c]pyrrole] (500 mg, 1.31 mmol) was dissolved in 10 mL dichloromethane and treated at 0° C. with triethylamine (166 mg, 1.64 mmol) and methansulfonyl chloride (158 mg, 1.38 mmol). After stirring at room temperature for 1 hour the reaction mixture was diluted with 50 mL dichloromethane and extracted with water. The organic phase was dried with MgSO$_4$ and concentrated. Chromatography on silica gel (hexane/ethyl acetate/triethylamine 70:30:4) gave 440 mg (73%) of the desired compound which was precipitated as its fumarate salt from a mixture of diethyl ether and methanol, dec>243° C., MS: m/e=460.5 (M+H$^+$).

EXAMPLE 109

(3'aRS,6'aRS)-1-[1-(cis-4-Isopropyl-cyclohexyl)-2'-phenyl-hexahydro-spiro[piperidine-4,1'-pyrrolo[3,4-c]pyrrole]-15'-yl]-ethanone fumarate (1:1)

The title compound, dec>218° C. and MS: m/e=424.5 (M+H$^+$) was prepared in accordance with the general method of example 108 from 3'aRS,6'aSR)-4-(cis-4-isopropyl-cyclohexyl)-2'-phenyl-hexahydro-spiro[piperidine-4,1'(2'H)-pyrrolo[3,4-c]pyrrole] and acetic anhydride.

EXAMPLE 110

(3'aRS,6'aRS)-1-[1-(cis-4-Isopropyl-cyclohexyl)-2'-phenyl-hexahydro-spiro[piperidine-4,1'-pyrrolo[3,4-c]pyrrole]-15'-yl-2,2,2-trifluoro-ethanone fumarate (1:1)

The title compound, dec>190° C. and MS: m/e=478.5 (M+H$^+$) was prepared in accordance with the general method of example 108 from (3'aRS,6'aSR)-4-(cis-4-isopropyl-cyclohexyl)-2'-phenyl-hexahydro-spiro[piperidine-4,1'(2'H)-pyrrolo[3,4-c]pyrrole] and trifluoroacetic acid anhydride.

EXAMPLE 111

(3'aRS,6'aRS)-1-[1-(cis-4-Isopropyl-cyclohexyl)-2'-phenyl-hexahydro-spiro[piperidine-4,1'-pyrrolo[3,4-c]pyrrol]-5'-yl]-2-methoxy-ethanone fumarate (1:1.05)

The title compound, dec>238° C. and MS: m/e=454.6 (M+H$^+$) was prepared in accordance with the general method of example 108 from (3'aRS,6'aSR)-4-(cis-4-isopropyl-cyclohexyl)-2'-phenyl-hexahydro-spiro[piperidine-4,1'(2'H)-pyrrolo[3,4-c]pyrrole] and methoxy acetic acid chloride.

EXAMPLE 112

(3'aRS,6'aRS)1-(cis-4-Isopropyl-cyclohexyl)-2'-phenyl-hexahydro-spiro[piperidine-4,1'-pyrrolo[3,4-c]pyrrole]-5'-carboxylic acid diethylamide fumarate (1:1)

The title compound, dec>224° C. and MS: m/e=481.5 (M+H$^+$) was prepared in accordance with the general method of example 108 from (3'aRS,6'aSR)-4-(cis-4-isopropyl-cyclohexyl)-2'-phenyl-hexahydro-spiro[piperidine-4,1'(2'H)-pyrrolo[3,4-c]pyrrole] and dimethyl-carbamoyl chloride.

EXAMPLE 113

(3'aRS,6'aSR)-2-[1-(cis-4-Isopropyl-cyclohexyl)-2'-phenyl-hexahydro-spiro[piperidine-4,1'-pyrrolo[3,4-c]pyrrol]-5'-yl]-N,N-dimethyl-acetamide fumarate (1:1.6)

The title compound, dec>228° C. and MS: m/e=467.4 (M+H$^+$) was prepared in accordance with the general method of example 108 from (3'aRS,6'aSR)-4-(cis-4-isopropyl-cyclohexyl)-2'-phenyl-hexahydro-spiro[piperidine-4,1'(2'H)-pyrrolo[3,4-c]pyrrole] and dimethyl-carbamoyl

EXAMPLE 114

(3'aRS,6'aRS)-1-(cis-4-Isopropyl-cyclohexyl)-2'-phenyl-5'-(thiophene-2-sulfonyl)-hexahydro-spiro[piperidine-4,1'-pyrrolo[3,4-c]pyrrole]fumarate (1:1)

The title compound, dec>254° C. and MS: m/e=528.3 (M+H$^+$) was prepared in accordance with the general method of example 108 from (3'aRS,6'aSR)-4-(cis-4-isopropyl-cyclohexyl)-2'-phenyl-hexahydro-spiro[piperidine-4,1'(2'H)-pyrrolo[3,4-c]pyrrole] and 2-thiophene sulfonyl chloride.

EXAMPLE 115

(3'aRS,6'aRS)-[1-(cis-4-Isopropyl-cyclohexyl)-2'-phenyl-hexahydro-spiro[piperidine-4,1'-pyrrolo[3,4-c]pyrrol]-5'-yl]-pyridin-3-yl-methanone fumarate (1:1)

The title compound, dec>248° C. and MS: m/e=487.4 (M+H$^+$) was prepared in accordance with the general method of example 108 from (3'aRS,6'aSR)-4-(cis-4- isopropyl-cyclohexyl)-2'-phenyl-hexahydro-spiro [piperidine-4,1'(2'H)-pyrrolo[3,4-c]pyrrole] and nicotinic acid chloride.

EXAMPLE 116

(3'aRS,6'aRS)-5-Benzenesulfonyl-1-(cis-4-isopropyl-cyclohexyl)-2'-phenyl-hexahydro-spiro [piperidine-4,1'-pyrrolo[3,4-c]pyrrole]fumarate (1:1)

The title compound, dec>243° C. and MS: m/e=522.3 (M+H$^+$) was prepared in accordance with the general method of example 108 from (3'aRS,6'aSR)-4-(cis-4-isopropyl-cyclohexyl)-2'-phenyl-hexahydro-spiro [piperidine-4,1'(2'H)-pyrrolo[3,4-c]pyrrole] and benzene sulfonyl chloride.

EXAMPLE 117

(3'aRS,6'aRS)-Cyclopropyl-[1-(cis-4-isopropyl-cyclohexyl)-2'phenyl-hexahydro-spiro[piperidine-4, 1'-pyrrolo[3,4-c]pyrrol]-5'-yl]-methanone fumarate (1:1.1)

The title compound, dec>247° C. and MS: m/e=476.3 (M+H$^+$) was prepared in accordance with the general method of example 108 from (3'aRS,6'aSR)-4-(cis-4-isopropyl-cyclohexyl)-2'-phenyl-hexahydro-spiro [piperidine-4,1'(2'H)-pyrrolo[3,4-c]pyrrole] and cyclopropyl carbonyl chloride.

EXAMPLE 118

(3'aRS,6'aSR)-Furan-2-yl-[1-(cis-4-isopropyl-cyclohexyl)-5'-phenyl-hexahydro-spiro[piperidine-4, 1'-pyrrolo[3,4-c]pyrrol]-5'-yl]-methanone fumarate (1:1.5)

The title compound, dec>250° C. and MS: m/e=476.3 (M+H$^+$) was prepared in accordance with the general method of example 108 from 3'aRS,6'aSR)-4-(cis-4-isopropyl-cyclohexyl)-2'-phenyl-hexahydro-spiro [piperidine-4,1'(2'H)-pyrrolo[3,4-c]pyrrole] and furan-2-carboxylic acid chloride.

EXAMPLE 119

(3'aRS,6'aRS)1-(cis-4-Isopropyl-cyclohexyl)-2'-phenyl-hexahydro-spiro[piperidine-4,1'-pyrrolo[3,4-c]pyrrole]-5'-carboxylic acid tert-butyl ester fumarate (1:1.05)

(3'aRS,6aSR)-4-(cis-4-Isopropyl-cyclohexyl)-2'-phenyl-hexahydro-spiro[piperidine-4,1'(2'H)-pyrrolo[3,4-c]pyrrole] (1.40 g, 3.67 mmol) was dissolved in 40 mL 1,4-dioxane and 20 mL water and treated at room temperature with sodium carbonate (620 mg, 7.34 mmol) and di-tert.-butyl dicarbonate (960 mg, 4.40 mmol). After stirring at room temperature for 16 hours the reaction mixture was diluted with 100 mL ethyl acetate and extracted with water. The organic phase was dried with MgSO$_4$ and concentrated. Chromatography on silica gel (hexane/ethyl acetate/triethylamine 40:10:1) gave 1.15 g (65%) of the desired compound which was precipitated as its fumarate salt from a mixture of diethyl ether and methanol, dec>244° C., MS: m/e=482.5 (M+H$^+$).

EXAMPLE 120

(3'aRS,6'aSR)-1-Cyclodecyl-2'-phenyl-hexahydro-spiro[piperidine-4,1'-pyrrolo[3,4-c]pyrrole]fumarate (1:2)

The title compound, white solid, m.p. 200° C. and MS: m/e=396.4 (M+H$^+$) was prepared by hydrogenation of (3'aRS,6'aSR)-5'-benzyl-1-cyclodecyl-2'-phenyl-hexahydro-spiro[piperidine-4,1'-pyrrolo[3,4-c]pyrrole] and subsequent formation of the fumarate in accordance with the general method of example 106.

EXAMPLE 121

(3'aRS,6'aSR)-1-Cyclodecyl-2'-(4-fluoro-phenyl)-5'-methyl-hexahydro-spiro[piperidine-4,1'-pyrrolo[3,4-c]pyrrole]-4',6'-dione fumarate (1:1)

The title compound, white solid, m.p. 244° C. and MS: m/e=456.5 (M+H$^+$) was prepared in accordance with the general method of example 5 from 1-cyclodecyl-piperidin-4-one, p-fluoro-aniline and N-methyl-maleimide and subsequent formation of the fumarate.

EXAMPLE 122

(3'aRS,6'aSR)-2'-(4-Fluoro-phenyl)-1-(cis-4-isopropyl-cyclohexyl)-5'-methyl-hexahydro-spiro [piperidine-4,1'-pyrrolo[3,4-c]pyrrole]-4',6'-dione fumarate (1:1)

The title compound, white solid, m.p. 220° C. and MS: m/e=442.4 (M+H$^+$) was prepared in accordance with the general method of example 5 from cis-1-(4-isopropyl-cyclohexyl)-piperidin-4-one, p-fluoro-aniline and N-methyl-maleimide and subsequent formation of the fumarate.

EXAMPLE 123

(3'aRS,6'aSR)-2'-(4-Fluoro-phenyl)-1-(cis-4-isopropyl-cyclohexyl)-5'-methyl-hexahydro-spiro [piperidine-4,1'-pyrrolo[3,4-c]pyrrole]fumarate (1:1)

The title compound, light red solid, m.p. 200° C. (dec.) and MS: m/e=414.5 (M+H$^+$) was prepared by reduction of (3'aRS,6'aSR)-2'-(4-fluoro-phenyl)-1-(cis-4-isopropyl-cyclohexyl)-5'-methyl-hexahydro-spiro[piperidine-4,1'-pyrrolo[3,4-c]pyrrole]-4',6'-dione and subsequent formation of the fumarate in accordance with the general method of example 15.

EXAMPLE 124

(3'aRS,6'aSR)-1-Cyclodecyl-2'-(3-fluoro-phenyl)-5'-methyl-hexahydro-spiro[piperidine-4,1'-pyrrolo[3,4-c]pyrrole]fumarate (1:2)

The title compound, light orange solid, m.p. 234° C. (dec.) and MS: m/e=428.6 (M+H$^+$) was prepared by reduction of (3'aRS,6'aSR)-1-cyclodecyl-2'-(3-fluoro-phenyl)-5'-methyl-hexahydro-spiro[piperidine-4,1'-pyrrolo[3,4-c] pyrrole]-4',6'-dione and subsequent formation of the fumarate in accordance with the general method of example 15.

(3'aRS,6'aSR)-1-Cyclodecyl-2'-(3-fluoro-phenyl)-5'-methyl-hexahydro-spiro[piperidine-4,1'-pyrrolo[3,4-c] pyrrole]-4',6'-dione was prepared in accordance with the general method of example 5 from 1-cyclodecyl-piperidin-4-one, m-fluoro-aniline and N-methyl-maleimide.

EXAMPLE 125

(3'aRS,6'aSR)-1-Cyclodecyl-2'-(4-fluoro-phenyl)-5'-methyl-hexahydro-spiro[piperidine-4,1'-pyrrolo[3,4-c]pyrrole]fumarate (1:2)

The title compound, light yellow solid, m.p. 236° C. (dec.) and MS: m/e=428.6 (M+H$^+$) was prepared by reduction of (3'aRS,6'aSR)-1-cyclodecyl-2'-(4-fluoro-phenyl)-5'-methyl-hexahydro-spiro[piperidine-4,1'-pyrrolo[3,4-c]pyrrole]-4',6'-dione and subsequent formation of the fumarate in accordance with the general method of example 89.

EXAMPLE 126

(3'aRS,6'aSR)-2'-(3-Fluoro-phenyl)-1-(cis-4-isopropyl-cyclohexyl)-5'-methyl-hexahydro-spiro[piperidine-4,1'-pyrrolo[3,4-c]pyrrole]-4',6'-dione fumarate (1:1)

The title compound, white solid, m.p. 242° C. (dec.) and MS: m/e=442.4 (M+H$^+$) was prepared in accordance with the general method of example 5 from cis-1-( 4-isopropyl-cyclohexyl)-piperidin-4-one, m-fluoro-aniline and N-methyl-maleimide and subsequent formation of the fumarate.

EXAMPLE 127

(3'aRS,6'aSR)-1-Cyclodecyl-5'-methyl-2'-(4-methyl-phenyl)-hexahydro-spiro[piperidine-4,1'-pyrrolo[3,4-c]pyrrole]-4',6'-dione fumarate (1:1)

The title compound, white solid, m.p. 243° C. and MS: m/e=452.5 (M+H$^+$) was prepared in accordance with the general method of example 5 from 1-cyclodecyl-piperidin-4-one, p-methyl-aniline and N-methyl-maleimide and subsequent formation of the fumarate.

EXAMPLE 128

(3'aRS,6'aSR)-2'-(3-Fluoro-phenyl)-1-(cis-4-isopropyl-cyclohexyl)-5'-methyl-hexahydro-spiro[piperidine-4,1'-pyrrolo[3,4-c]pyrrole]-4',6'-dione fumarate (1:2)

The title compound, white solid, m.p. 210° C. (dec.) and MS: m/e=414.5 (M+H$^+$) was prepared by reduction of (3'aRS,6'aSR)-2'-(3-fluoro-phenyl)-1-(cis-4-isopropyl-cyclohexyl)-5'-methyl-hexahydro-spiro[piperidine-4,1'-pyrrolo[3,4-c]pyrrole]-4',6'-dione and subsequent formation of the fumarate in accordance with the general method of example 89.

EXAMPLE 129

(3'aS,6'aR)-1-Cyclononyl-5'-methyl-2'-phenyl-hexahydro-spiro[piperidine-4,1'-pyrrolo[3,4-c]pyrrole]fumarate (1:2.3)

The title compound, light orange solid, m.p. 132° C. (dec.); $[\alpha]_D^{20}$=−78.6° (c=0.1044 in MeOH) and MS: m/e=396.4 (M+H$^+$) was prepared by reduction of (3'aS,6'aR)-1-cyclononyl-5'-methyl-2'-phenyl-hexahydro-spiro[piperidine-4,1'(2'H)-pyrrolo[3,4-c]pyrrole]-4',6'-dione and subsequent formation of the fumarate in accordance with the general method of example 89.

(3'aS,6'aR)-1-Cyclononyl-5'-methyl-2'-phenyl-hexahydro-spiro[piperidine-4,1'(2'H)-pyrrolo[3,4-c]pyrrole]-4',6'-dione was prepared from (3'aS,6'aR)-5'-methyl-1'-phenyl-hexahydro-spiro[piperidine-4,1'(2'H)-pyrrolo[3,4-c]pyrrole]-4',6'-dione and cyclononanone in accordance with the general method of example 3.

EXAMPLE 130

(3'aS,6'aR)-1-Cyclodecyl-2'-(2-fluoro-phenyl)-5'-methyl-hexahydro-spiro[piperidine-4,1'-pyrrolo[3,4-c]pyrrole]fumarate (1:2.1)

The title compound, light orange solid, m.p. 223° C. (dec.) and MS: m/e=428.6 (M+H$^+$) was prepared by reduction of (3'aRS,6'aSR)-1-cyclodecyl-2'-(2-fluoro-phenyl)-5'-methyl-hexahydro-spiro[piperidine-4,1'-pyrrolo[3,4-c]pyrrole]-4',6'-dione and subsequent formation of the fumarate in accordance with the general method of example 89.

(3'aRS,6'aSR)-1-Cyclodecyl-2'-(2-fluoro-phenyl)-5'-methyl-hexahydro-spiro[piperidine-4,1'-pyrrolo[3,4-c]pyrrole]-4',6'-dione was prepared in accordance with the general method of example 5 from 1-cyclodecyl-piperidin-4-one, o-fluoro-aniline and N-methyl-maleimide.

EXAMPLE 131

(3'aRS,6'aSR)-1-Cyclodecyl-5'-methyl-2'-(4-methyl-phenyl)-hexahydro-spiro[piperidine-4,1'-pyrrolo[3,4-c]pyrrole]fumarate (1:2.2)

The title compound, light pink solid, m.p. 249° C. (dec.) and MS: m/e=424.5 (M+H$^+$) was prepared by reduction of (3'aRS,6'aSR)-1-cyclodecyl-2'-(4-methyl-phenyl)-5'-methyl-hexahydro-spiro[piperidine-4,1'-pyrrolo[3,4-c]pyrrole]-4',6'-dione and subsequent formation of the fumarate in accordance with the general method of example 89.

EXAMPLE 132

(3'aRS,6'aSR)-1-Cyclononyl-2'-(4-fluoro-phenyl)-5'-methyl-hexahydro-spiro[piperidine-4,1'-pyrrolo[3,4-c]pyrrole]-4',6'-dione fumarate (1:1)

The title compound, white solid, m.p. 247° C. and MS: m/e=442.4 (M+H$^+$) was prepared in accordance with the general method of example 5 from 1-cyclononyl-piperidin-4-one, p-fluor

EXAMPLE 133

(3'aRS,6'aSR)-1-Cyclodecyl-5'-methyl-2'-(3-methyl-phenyl)-hexahydro-spiro[piperidine-4,1'-pyrrolo[3,4-c]pyrrole]-4,6'-dione fumarate (1:1)

The title compound, off-white solid, m.p. 249° C. (dec.) and MS: m/e=452.5 (M+H$^+$) was prepared in accordance with the general method of example 5 from 1-cyclodecyl-piperidin-4-one, m-methyl-aniline and N-methyl-maleimide and subsequent formation of the fumarate.

EXAMPLE 134

(3'aRS,6'aSR)-2'-(4-Chloro-phenyl)-1-cyclodecyl-5'-methyl-hexahydro-spiro[piperidine-4,1'-pyrrolo[3,4-c]pyrrole]-4',6'-dione fumarate (1:1)

The title compound, light yellow solid, m.p. 241° C. (dec.) and MS: m/e=472.3 (M+H$^+$) was prepared in accordance with the general method of example 5 from 1-cyclodecyl-piperidin-4-one, p-chloro-aniline and N-methyl-maleimide and subsequent formation of the fumarate.

EXAMPLE 135

(3'aRS,6'aSR)-2'-(4-Chloro-phenyl)-1-cyclodecyl 5'-methyl-hexahydro-spiro[piperidine-4,1'-pyrrolo[3,4-c]pyrrole]fumarate (1:2)

The title compound, light pink solid, m.p. 243° C. (dec.) and MS: m/e=444.4 (M+H$^+$) was prepared by reduction of (3'aRS,6'aSR)-1-cyclodecyl-2'-(4-chloro-phenyl)-5'-methyl-hexahydro-spiro[piperidine-4,1'-pyrrolo[3,4-c]

pyrrole]-4',6'-dione and subsequent formation of the fumarate in accordance with the general method of example 89.

EXAMPLE 136

(3'aRS,6'aSR)-1-(cis-4-Isopropyl-cyclohexyl)-5'-methyl-2'-(4-methyl-phenyl)-hexahydro-spiro[piperidine-4,1'-pyrrolo[3,4-c]pyrrole]fumarate (1:2.3)

The title compound, light red solid, m.p. 256° C. (dec.) and MS: m/e=410.6 (M+H$^+$) was prepared by reduction of (3'aRS,6'aSR)-2'-(4-methyl-phenyl)-1-(cis-4-isopropyl-cyclohexyl)-5'-methyl-hexahydro-spiro[piperidine-4,1'-pyrrolo[3,4-c]pyrrole]-4',6'-dione and subsequent formation of the fumarate in accordance with the general method of example 89.

(3'aRS,6'aSR)-2'-(4-Methyl-phenyl)-1-(cis-4-isopropyl-cyclohexyl)-5'-methyl-hexahydro-spiro[piperidine-4,1'-pyrrolo[3,4-c]pyrrole]-4',6'-dione was prepared in accordance with the general method of example 5 from cis-1-(4-isopropyl-cyclohexyl)-piperidin-4-one, p-methyl-aniline and N-methyl-maleimide.

EXAMPLE 137

(3'aRS,6'aSR)-2'-(2-Fluoro-phenyl)-1-(cis-4-isopropyl-cyclohexyl)-5'-methyl-hexahydro-spiro[piperidine-4,1'-pyrrolo[3,4-c]pyrrole]fumarate (1:2.3)

The title compound, light orange solid, m.p. 160° C. (dec.) and MS: m/e=414.4 (M+H$^+$) was prepared by reduction of (3'aRS,6'aSR)-2'-(2-fluoro-phenyl)-1-(cis-4-isopropyl-cyclohexyl)-5'-methyl-hexahydro-spiro[piperidine-4,1'-pyrrolo[3,4-c]pyrrole]-4',6'-dione and subsequent formation of the fumarate in accordance with the general method of example 89.

(3'aRS,6'aSR)-2'-(2-Fluoro-phenyl)-1-(cis-4-isopropyl-cyclohexyl)-5'-methyl-hexahydro-spiro[piperidine-4,1'-pyrrolo[3,4-c]pyrrole]-4',6'-dione was prepared in accordance with the general method of example 5 from cis-1-(4-isopropyl-cyclohexyl)-piperidin-4-one, o-fluoro-aniline and N-methyl-maleimide.

EXAMPLE 138

(3'aRS,6'aSR)-1-Cyclodecyl-5'-methyl-2'-(3-methyl-phenyl)-hexahydro-spiro[piperidine-4,1'-pyrrolo[3,4-c]pyrrole]fumarate (1:2)

The title compound, light pink solid, m.p. 219° C. and MS: m/e=424.5 (M+H$^+$) was prepared by reduction of (3'aRS,6'aSR)-1-cyclodecyl-2'-(3-methyl-phenyl)-5'-methyl-hexahydro-spiro[piperidine-4,1'-pyrrolo[3,4-c]pyrrole]-4',6'-dione and subsequent formation of the fumarate in accordance with the general method of example 89.

EXAMPLE 139

(3'aRS,6'aSR)-1-Cyclononyl-2'-(4-fluoro-phenyl)-5'-methyl-hexahydro-spiro[piperidine-4,1'-pyrrolo[3,4-c]pyrrole]fumarate (1:2)

The title compound, light pink solid, m.p. 225° C. and MS: m/e=414.4 (M+H$^+$) was prepared by reduction of (3'aRS,6'aSR)-1-cyclononyl-2'-(4-fluoro-phenyl)-5'-methyl-hexahydro-spiro[piperidine-4,1'-pyrrolo[3,4-c]pyrrole]-4',6'-dione and subsequent formation of the fumarate in accordance with the general method of example 89.

EXAMPLE 140

(3'aRS,6'aSR)-5'-Benzyl-1-cyclononyl-2'-phenyl-hexahydro-spiro[piperidine-4,1'-pyrrolo[3,4-c]pyrrole]fumarate (1:2)

The title compound, off-white solid, m.p. 210° C. (dec.) and MS: m/e 472.4 (M+H$^+$) was prepared by reduction of (3'aRS,6'aSR)-5'-benzyl-1-cyclononyl-2'-phenyl-hexahydro-spiro[piperidine-4,1'-pyrrolo[3,4-c]pyrrole]-4',6'-dione and subsequent formation of the fumarate in accordance with the general method of example 89.

(3'aRS,6'aSR)-5'-Benzyl-1-cyclononyl-2'-phenyl-hexahydro-spiro[piperidine-4,1'-pyrrolo[3,4-c]pyrrole]-4',6'-dione was prepared in accordance with the general method of example 5 from 1-cyclononyl-piperidin-4-one, aniline and N-benzyl-maleimide.

EXAMPLE 141

(3'aRS,6'aSR)-1-Cyclononyl-2'-phenyl-hexahydro-spiro[piperidine-4,1'-pyrrolo[3,4'-c]pyrrole]fumarate (1:3.5)

The title compound, off-white solid, m.p. 173° C. and MS: m/e=382.4 (M+H$^+$) was prepared by hydrogenation of (3'aRS,6'aSR)-5'-benzyl-1-cyclononyl-2'-phenyl-hexahydro-spiro[piperidine-4,1'-pyrrolo[3,4-c]pyrrole] and subsequent formation of the fumarate in accordance with the general method of example 106.

EXAMPLE 142

(3'aRS,6'aSR)-1-Cyclodecyl-2'-(4-fluoro-phenyl)-hexahydro-spiro[piperidine-4,1'-pyrrolo[3,4-c]pyrrole]-4',6'-dione fumarate (1:1)

The title compound, light yellow solid, m.p. 246° C. (dec.) and MS: m/e=442.4 (M+H$^+$) was prepared in accordance with the general method of example 5 from 1-cyclodecyl-piperidin-4-one, p-fluoro-aniline and maleimide and subsequent formation of the fumarate.

EXAMPLE 143

(3'aRS,6'aSR)-2'-(4-Chloro-phenyl)-1-(cis-4-isopropyl-cyclohexyl)-5'methyl-hexahydro-spiro[piperidine-4,1'-pyrrolo[3,4-c]pyrrole]-4',6'-dione fumarate (1:1)

The title compound, white solid, m.p. 219° C. and MS: m/e=458.4 (M+H$^+$) was prepared in accordance with the general method of example 5 from cis-1-(4-isopropyl-cyclohexyl)-piperidin-4-one, m-chloro-aniline and N-methyl-maleimide and subsequent formation of the fumarate.

EXAMPLE 144

(3'aRS,6'aS-2'-(4-Chloro-phenyl)-1-(cis-4-isopropyl-cyclohexyl)-5'methyl-hexahydro-spiro[piperidine-4,1'-pyrrolo[3,4-c]pyrrole]fumarate (1:2.1)

The title compound, light red solid, m.p. 241° C. (dec.) and MS: m/e=430.5 (M+H$^+$) was prepared by reduction of (3'aRS,6'aSR)-2'-(4-chloro-phenyl)-1-(cis-4-isopropyl-cyclohexyl)-5'-methyl-hexahydro-spiro[piperidine-4,1'-

EXAMPLE 145

(3'aRS,6'aSR)-1-(cis-4-Isopropyl-cyclohexyl)-2'-(4-methoxy-phenyl)-5'-methyl-hexahydro-spiro [piperidine-4,1'-pyrrolo[3,4-c]pyrrole]-4',6'-dione fumarate (1:1)

The title compound, white solid, m.p. 205° C. and MS: m/e=454.5 (M+H$^+$) was prepared in accordance with the general method of example 5 from cis-1-(4-isopropyl-cyclohexyl)-piperidin-4-one, p-methoxy-aniline and N-methyl-maleimide and subsequent formation of the fumarate.

EXAMPLE 146

(3'aRS,6'aSR)-1-(cis-4-Isopropyl-cyclohexyl)-2'-(4-methoxy-phenyl)-5'-methyl-hexahydro-spiro [piperidine-4,1'-pyrrolo[3,4-c]pyrrole]fumarate (1:2)

The title compound, light orange solid, m.p. 245° C. (dec.) and MS: m/e=426.6 (M+H$^+$) was prepared by reduction of (3'aRS,6'aSR)-2'-(4-methoxy-phenyl)-1-(cis-4-isopropyl-cyclohexyl)-5'-methyl-hexahydro-spiro [piperidine-4,1'-pyrrolo[3,4-c]pyrrole]-4',6'-dione and subsequent formation of the fumarate in accordance with the general method of example 89.

EXAMPLE 147

(3'aRS,6'aSR)-1-Cyclodecyl)-5'-cyclopropylmethyl-2'-(4-fluoro-phenyl)-hexahydro-spiro[piperidine-4,1'-pyrrolo[3,4-c]pyrrole]-4',6'-dione fumarate (1:1)

The title compound, light yellow solid, m.p. 247° C. (dec.) and MS: m/e=496.3 (M+H$^+$) was prepared by Mitsunobu-reaction of (3'aRS,6'aSR)-1-cyclodecyl-2'-(4-fluoro-phenyl)-hexahydro-spiro[piperidine-4,1'-pyrrolo[3,4-c]pyrrole]-4',6'-dione and cyclopropyl-methanol and subsequent formation of the fumarate in accordance with the general method of example 81.

EXAMPLE 148

(3'aRS,6'aSR)-1-Cyclodecyl-5'-cyclobutylmethyl-2'-(4-fluoro-phenyl)-hexahydro-spiro[piperidine-4,1'-pyrrolo[3,4-c]pyrrole]-4',6'-dione fumarate (1:1)

The title compound, light yellow solid, m.p. 245° C. (dec.) and MS: m/e=510.5 (M+H$^+$) was prepared by Mitsunobu-reaction of (3'aRS,6'aSR)-1-cyclodecyl-2'-(4-fluoro-phenyl)-hexahydro-spiro[piperidine-4,1'-pyrrolo[3,4-c]pyrrole]-4',6'-dione and cyclobutyl-methanol and subsequent formation of the fumarate in accordance with the general method of example 81.

EXAMPLE 149

(3'aRS,6'aSR)-1-Cyclodecyl-5'-cyclobutylmethyl-2'-(4-fluoro-phenyl)-hexahydro-spiro[piperidine-4,1'-pyrrolo[3,4-c]pyrrole]furmarate (1:2.3)

The title compound, light pink solid, m.p. 249° C. (dec.) and MS: m/e=482.5 (M+H$^+$) was prepared by reduction of (3'aRS,6'aSR)-1-cyclodecyl-5'-cyclobutylmethyl-2'-(4-fluoro-phenyl)-hexahydro-spiro[piperidine-4,1'-pyrrolo[3,4-c]pyrrole]-4',6'-dione and subsequent formation of the fumarate in accordance with the general method of example 89.

EXAMPLE 150

(3'aRS,6'aSR)-1-Cyclodecyl)-5'-cyclopropylmethyl-2'-(4-fluoro-phenyl)-hexahydro-spiro[piperidine-4, 1'-pyrrolo[3,4-c]pyrrole]fumarate (1:2)

The title compound, light pink solid, m.p. 242° C. (dec.) and MS: m/e=468.4 (M+H$^+$) was prepared by reduction of (3'aRS,6'aSR)-1-cyclodecyl-5'-cyclopropylmethyl-2'-(4-fluoro-phenyl)-hexahydro-spiro[piperidine-4,1'-pyrrolo[3, 4-c]pyrrole]-4',6'-dione and subsequent formation of the fumarate in accordance with the general method of example 89.

EXAMPLE 151

(3'aRS,6'aSR)-5'-tert-Butyl-1-cyclononyl)-2'-phenyl-hexahydro-spiro[piperidine-4,1'-pyrrolo[3,4-c] pyrrole]fumarate (1:2.5)

The title compound, light red solid, m.p. 220° C. (dec.) and MS: m/e=438.5 (M+H$^+$) was prepared by reduction of (3'aRS,6'aSR)-5'-tert-butyl-1-cyclononyl-2'-phenyl-hexahydro-spiro[piperidine-4,1'-pyrrolo[3,4-c]pyrrole]-4', 6'-dione and subsequent formation of the fumarate in accordance with the general method of example 89.

(3'aRS,6'aSR)-5'-tert-Butyl-1-cyclononyl-2'-phenyl-hexahydro-spiro[piperidine-4,1'-pyrrolo[3,4-c]pyrrole]-4', 6'-dione was prepared in accordance with the general method of example 5 from 1-cyclononyl-piperidin-4-one, aniline and N-tert-butyl-maleimide.

EXAMPLE 152

(3'aRS,6'aSR)-(1-Cyclononyl-2'-phenyl-hexahydro-spiro[piperine-4,1'-pyrrolo[3,4-c]pyrrol]-5'-yl)-cyclopropyl-methanone fumarate (1:1)

The title compound, light red solid, m.p. 236° C. (dec.) and MS: m/e=450.4 (M+H$^+$) was prepared by reaction of (3'aRS,6'aSR)-1-cyclononyl-2'-phenyl-hexahydro-spiro [piperidine-4,1'-pyrrolo[3,4-c]pyrrole] with cyclopropanecarbonyl chloride and subsequent formation of the fumarate in accordance with the general method of example 108.

EXAMPLE 153

(3'aRS,6'aSR)-1-Cyclononyl-5'-methylsulfonyl-2'-phenyl-hexahydro-spiro[piperine-4,1'-pyrrolo[3,4-c] pyrrole]fumarate (1:1)

The title compound, light red solid, m.p. 179° C. (dec.) and MS: m/e=460.4 (M+H$^+$) was prepared by reaction of (3'aRS,6'aSR)-1-cyclononyl-2'-phenyl-hexahydro-spiro [piperidine-4,1'-pyrrolo[3,4-c]pyrrole] with methanesulfonyl chloride and subsequent formation of the fumarate in accordance with the general method of example 108.

EXAMPLE 154

(3'aRS,6'aSR)-5'-Cyclopropylmethyl-2'-(4-fluoro-phenyl)-1-(cis-4-isopropyl-cyclohexyl)-hexahydro-spiro[piperine-4,1'-pyrrolo[3,4-c]pyrrole]fumarate (1:2)

The title compound, white solid, m.p. 209° C. and MS: m/e=454.6 (M+H$^+$) was prepared by reduction of (3'aRS, 6'aSR)-5'-cyclopropylmethyl-2'-(4-fluoro-phenyl)-1-(cis-4-isopropyl-cyclohexyl)-hexahydro-spiro[piperine-4,1'-pyrrolo[3,4-c]pyrrole]-4',6'-dione and subsequent formation of the fumarate in accordance with the general method of example 89.

EXAMPLE 155

(3'aRS,6'aSR)-5'-Cyclopropylmethyl-2'-(3-fluoro-phenyl)-1-(cis-4-isopropyl-cyclohexyl)-hexahydro-spiro[piperine-4,1'-pyrrolo[3,4-c]pyrrole]fumarate (1:2)

The title compound, light red solid, m.p. 235° C. (dec.) and MS: m/e=454.6 (M+H$^+$) was prepared by reduction of (3'aRS,6'aSR)-5'-cyclopropylnethyl-2'-(3-fluoro-phenyl)-1-(cis-4-isopropyl-cyclohexyl)-hexahydro-spiro[piperine-4,1'-pyrrolo[3,4-c]-4',6'-dione and subsequent formation of the fumarate in accordance with the general method of example 89.

EXAMPLE 156

(3'aRS,6'aSR)-1-Cyclodecyl-5'-cyclopropylmetlyl-2'-phenyl-hexahydro-spiro[piperine-4,1'-pyrrolo[3,4-c]pyrrole]-4',6'-dione fumarate (1:1)

The title compound, light yellow solid, m.p. 236° C. (dec.) and MS: m/e=478.5 (M+H$^+$) was prepared by Mitsunobu-reaction of (3'aRS,6'aSR)-1-cyclodecyl-2'-phenyl-hexahydro-spiro[piperidine-4,1'-pyrrolo[3,4-c]pyrrole]-4,6'-dione and cyclopropyl-methanol and subsequent formation of the fumarate in accordance with the general method of example 81.

EXAMPLE 157

(3'aRS,6'aSR)-(1-Cyclodecyl-2'-phenyl-hexahydro-spiro[piperine-4,1'-pyrrolo[3,4-c]pyrrol]-5'-yl)-phenyl-methanone fumarate (1:1)

The title compound, light pink solid, m.p. 203° C. (dec.) and MS: m/e=500.4 (M+H$^+$) was prepared by reaction of (3'aRS,6'aSR)-1-cyclodecyl-2'-phenyl-hexahydro-spiro[piperidine-4,1'-pyrrolo[3,4-c]pyrrole] with benzoyl chloride and subsequent formation of the fumarate in accordance with the general method of example 108.

EXAMPLE 158

(3'aRS,6'aSR)-(1-Cyclodecyl-2'-phenyl-hexahydro-spiro[piperine-4,1'-pyrrolo[3,4-c]pyrrol]-5'-yl)-cyclopropyl-methanone fumarate (1:1)

The title compound, white solid, m.p. 225° C. (dec.) and MS: m/e=464.4 (M+H$^+$) was prepared by reaction of (3'aRS,6'aSR)-1-cyclodecyl-2'-phenyl-hexahydro-spiro[piperidine-4,1'-pyrrolo[3,4-c]pyrrole] with cyclopropanecarbonyl chloride and subsequent formation of the fumarate in accordance with the general method of example 108.

EXAMPLE 159

(3'aRS,6'aSR)-1-(1-Cyclodecyl-2'-phenyl-hexahydro-spiro[piperine-4,1'-pyrrolo[3,4-c]pyrrol]-5'-yl)-ethanone fumarate (1:1)

The title compound, light yellow solid, m.p. 200° C. (dec.) and MS: m/e=438.5 (M+H$^+$) was prepared by reaction of (3'aRS,6'aSR)-1-cyclodecyl-2'-phenyl-hexahydro-spiro[piperidine-4,1'-pyrrolo[3,4-c]pyrrole] with acetyl chloride and subsequent formation of the fumarate in accordance with the general method of example 108.

EXAMPLE 160

(3'aRS,6'aSR)-1-Cyclodecyl-5-cyclopropylmethyl-2'-phenyl-hexahydro-spiro[piperine-4,1'-pyrrolo[3,4-c]pyrrole]fumarate (1:2.1)

The title compound, light red solid, m.p. 219° C. (dec.) and MS: m/e 450.5 (M+H$^+$) was prepared by reduction of (3'aRS,6'aSR)-1-cyclodecyl-5'-cyclopropylmethyl-2'-phenyl-hexahydro-spiro[piperine-4,1'-pyrrolo[3,4-c]pyrrole]-4',6'-dione and subsequent formation of the fumarate in accordance with the general method of example 89.

EXAMPLE 161

(3'aRS,6'aSR)-1-Cyclodecyl-5'-methylsulfonyl-2'-phenyl-hexahydro-spiro[piperine-4,1'-pyrrolo[3,4-c]pyrrole]fumarate (1:1)

The title compound, white solid, m.p. 252° C. (dec.) and MS: m/e=474.4 (M+H$^+$) was prepared by reaction of (3'aRS,6'aSR)-1-cyclodecyl-2'-phenyl-hexahydro-spiro[piperidine-4,1'-pyrrolo[3,4-c]pyrrole] with methanesulfonyl chloride and subsequent formation of the fumarate in accordance with the general method of example 108.

EXAMPLE 162

(3'aRS,6'aSR)-1-Cyclodecyl-2'-phenyl-hexahydro-spiro[piperidine-4,1'-pyrrolo[3,4-c]pyrrole]-5'-carboxylic acid phenylamide fumarate (1:0.8)

The title compound, white solid, m.p. 202° C. (dec.) and MS: m/e=515.3 (M+H$^+$) was prepared by reaction of (3'aRS,6'aSR)-1-cyclodecyl-2'-phenyl-hexahydro-spiro[piperidine-4,1'-pyrrolo[3,4-c]pyrrole] with phenyl isocyanate and subsequent formation of the fumarate in accordance with the general method of example 108.

EXAMPLE 163

(3'aRS,6'aSR)-1-(1-Cyclodecyl-2'-phenyl-hexahydro-spiro[piperidine-4,1'-pyrrolo[3,4-c]pyrrol]-5'-yl)-2,2-dimethyl-propan-1-one fumarate (1:0.9)

The title compound, white solid, m.p. 232° C. (dec.) and MS: m/e=480.5 (M+H$^+$) was prepared by reaction of (3'aRS,6'aSR)-1-cyclodecyl-2-phenyl-hexahydro-spiro[piperidine-4,1'-pyrrolo[3,4-c]pyrrole] with pivaloyl chloride and subsequent formation of the fumarate in accordance with the general method of example 108.

EXAMPLE 164

(3'aRS,6'aSR)-1-Cyclodecyl-2'-phenyl-hexahydro-spiro[piperidine-4,1'-pyrrolo[3,4-c]pyrrole]-5-carboxylic acid ethyl ester fumarate (1:1)

The title compound, white solid, m.p. 260° C. (dec.) and MS: m/e=468.4 (M+H$^+$) was prepared by reaction of (3'aRS,6'aSR)-1-cyclodecyl-2'-phenyl-hexahydro-spiro[piperidine-4,1'-pyrrolo[3,4-c]pyrrole] with ethyl chloroformate and subsequent formation of the fumarate in accordance with the general method of example 108.

EXAMPLE 165

(3'aRS,6'aSR)-1-Cyclodecyl-2'-phenyl-hexahydro-spiro[piperidine-4,1'-pyrrolo[3,4-c]pyrrole]-5'-sulfonic acid dimethylamide fumarate (1:1)

The title compound, white solid, m.p. 253° C. (dec.) and MS: m/e=503.4 (M+H$^+$) was prepared by reaction of (3'aRS, 6'aSR)-1-cyclodecyl-2'-phenyl-hexahydro-spiro[piperidine-4,1'-pyrrolo[3,4-c]pyrrole] with N,N-dimethylsulfamoyl chloride and subsequent formation of the fumarate in accordance with the general method of example 108.

EXAMPLE 166

(3'aRS,6'aSR)-1-Cyclodecyl-2'-phenyl-5'-benzenesulfonyl-hexahydro-spiro[piperidine-4,1'-pyrrolo[3,4-c]pyrrole]fumarate (1:1)

The title compound, white solid, m.p. 235° C. (dec.) and MS: m/e=536.4 (M+H$^+$) was prepared by reaction of (3'aRS,6'aSR)-1-cyclodecyl-2'-phenyl-hexahydro-spiro[piperidine-4,1'-pyrrolo[3,4-c]pyrrole] with phenylsulfonyl chloride and subsequent formation of the fumarate in accordance with the general method of example 108.

EXAMPLE 167

(3'aRS,6'aSR)-[1-(cis-4-Isopropyl-cyclohexyl)-2'-phenyl-hexahydro-spiro[piperidine-4,1'-pyrrolo[3,4-c]pyrrol]-5'-yl]-pyridin-2-yl-methanone fumarate (1:1.12)

The title compound, dec>240° C. and MS: m/e=487.5 (M+H$^+$) was prepared in accordance with the general method of example 108 from 3'aRS,6'aSR)-4-(cis-4-isopropyl-cyclohexyl)-2'-phenyl-hexahydro-spiro[piperidine-4,1'(2'H)-pyrrolo[3,4-c]pyrrole] and 2-picolinic acid chloride.

EXAMPLE 168

(3'aRS,6'aRS)-1-(cis-4-Isopropyl-cyclohexyl)-2'-phenyl-hexahydro-spiro[piperidine-4,1'-pyrrolo[3,4-c]pyrrol]-5'-yl]-thiophen-2-yl-methanone fumarate (1:1.1)

The title compound, dec>243° C. and MS: m/e=492.4 (M+H$^+$) was prepared in accordance with the general method of example 108 from 3'aRS,6'aSR)-4-(cis-4-isopropyl-cyclohexyl)-2'-phenyl-hexahydro-spiro[piperidine-4,1'(2'H)-pyrrolo[3,4-c]pyrrole] and 2-thiophene carbonyl chloride.

EXAMPLE 169

(3'aRS,6'aRS)-1-(cis-4-Isopropyl-cyclohexyl)-2'-phenyl-hexahydro-spiro[piperidine-4,1'-pyrrolo[3,4-c]pyrrol]-5'-yl]-morpholin-4-yl-methanone fumarate (1:1)

The title compound, dec>253° C. and MS: me=495.5 (M+H$^+$) was prepared in accordance with the general method of example 108 from 3'aRS,6'aSR)-4-(cis-4-isopropyl-cyclohexyl)-2'-phenyl-hexahydro-spiro[piperidine-4,1'(2'H)-pyrrolo[3,4-c]pyrrole] and morpholine N-carbonyl chloride.

EXAMPLE 170

(3'aRS,6'aRS)-1-(cis-4-Isopropyl-cyclohexyl)-2'-phenyl-hexahydro-spiro[piperidine-4,1'-pyrrolo[3,4-c]pyrrol]-5'-yl]-pyridin-4-yl-methanone fumarate (1:1)

The title compound, dec>250° C. and MS: m/e=487.5 (M+H$^+$) was prepared in accordance with the general method of example 108 from 3'aRS,6'aSR)-4-(cis-4-isopropyl-cyclohexyl)-2'-phenyl-hexahydro-spiro[piperidine-4,1'(2'H)-pyrrolo[3,4-c]pyrrole] and isonicotinoyl chloride.

EXAMPLE 171

(3'aRS,6'aRS)-1-(cis-4-Isopropyl-cyclohexyl)-2'-phenyl-hexahydro-spiro[piperidine-4,1'-pyrrolo[3,4-c]pyrrole]-5'-carboxylic acid phenyl ester fumarate (1:1)

The title compound, dec>225° C. and MS: m/e=502.4 (M+H$^+$) was prepared in accordance with the general method of example 108 from 3'aRS,6'aSR)-4-(cis-4-isopropyl-cyclohexyl)-2'-phenyl-hexahydro-spiro[piperidine-4,1'(2'H)-pyrrolo[3,4-c]pyrrole] and phenyl chloroformate.

EXAMPLE 172

(3'aRS,6'aSR)-[1-(cis-4-Isopropyl-cyclohexyl)-2'-(4-fluoro-phenyl)-hexahydro-spiro[piperidine-4,1'-pyrrolo[3,4-c]pyrrol]-5'-yl]-pyridin-3-yl-methanone fumarate (1:1)

The title compound, dec>230° C. and MS: m/e=505.4 (M+H$^+$) was prepared in accordance with the general method of example 108 from (3'aRS,6'aSR)-1-(cis-4-isopropyl-cyclohexyl)-2'-(4-fluoro-phenyl)-hexahydro-spiro[piperidine-4,1'-pyrrolo[3,4-c]pyrrole] and nicotinic acid chloride.

SYNTHESES OF INTERMEDIATES

EXAMPLE AA cis-[1-(4-Isopropyl-cyclohexyl)-piperidin-4-ylidene]phenyl-amine cis-1-(4-Isopropyl-cyclohexyl)-piperidine-4-on (5.0 g, 23.4 mmol), aniline (3.3 g, 35.3 mmol) and molecular sieves (20 g, 4A) were stirred in 100 ml pentane at room temperature for 6 days. The molecular sieves was filtered off and the solvent was evaporated. The crude product was used without any further purification for the following step.

EXAMPLE AB (3'aRS,6'aSR)-1-Benzyl-5'-methyl-1'-phenyl-hexahydro-spiro[piperidine-4,1'(2'H)-pyrrolo[3,4-c]pyrrole]-4',6'-dione The title compound, pale yellow foam, MS: m/e=390.3 (M+H$^+$) was prepared in accordance with the general method of example 5 from 1-benzyl-piperidin-4-one, aniline and N-methyl-maleimide

EXAMPLE AC (3'aRS,6'aSR)-5'-Methyl-1'-phenyl-hexahydro-spiro[piperidine-4,1'(2'H)-pyrrolo[3,4-c]pyrrole]-4',6'-dione The title compound, pale brown foam, MS: m/e=300.3 (M+H$^+$) was prepared by hydrogenation of (3'aRS,6'aSR)-5'-methyl-2'-phenyl-1-[(R)-1-phenyl-ethyl]-hexahydro-spiro[piperidine-4,1'-pyrrolo[3,4-c]pyrrole]-4',6'-dione in accordance with the general method of example 106.

EXAMPLE AD

1-Cyclodecyl-piperidin-4-one

To a solution of cyclodecylamine (6.78 g, 44 mmol) in ethanol (80 ml) was added a solution of potassium carbonate (0.60 g, 3.9 mmol) and 1-ethyl-1-methyl-4-oxo-piperidinium iodide (16.2 g, 60 mmol) in water (40 ml) and the mixture was refluxed for 100 min. The reaction mixture was poured into sat. NaHCO$_3$-solution (120 ml)/ice (400 ml) and extracted with ethylacetate (2×300 ml). The combined organic layers were dried (MgSO$_4$) and evaporated. Column chromatography on silica gel (toluene/ethylacetate 2:1) yielded the title compound (8.8 g, 85%) as a pale brown oil, MS: m/e=238.4 (M$^+$).

EXAMPLE AE

1-Cyclononyl-piperidin-4-one

The title compound, yellow oil, MS: m/e=223 (M$^+$) was prepared by reaction of cyclononylamine and 1-ethyl-1-methyl-4-oxo-piperidinium iodide in accordance with the general method of example AD.

EXAMPLE AF (R)-1-(1-Phenyl-ethyl)-piperidin-4-one

The title compound, pale brown oil, $[\alpha]_D^{20}$=+13.3° (c=0.4286 in CHCl$_3$) and MS: m/e=203 (M$^+$) was prepared by reaction of cyclononylamine and 1-ethyl-1-methyl-4-oxo-piperidinium iodide in accordance with the general method of example AD.

EXAMPLE AG (3'aS,6'aR)-5-methyl-2'-phenyl-1-[(R)-1-phenyl-ethyl]-hexahydro-spiro[piperidine-4,1'-pyrrolo[3,4-c]pyrrole]-4',6'-dione The title compound, white foam, $[\alpha]_D^{20}$=−143.3° (c=0.2855 in CHCl$_3$) and MS: m/e=404.4 (M+H$^+$) was prepared in accordance with the general method of example 5 from (R)-1-(1-phenyl-ethyl)-piperidin-4-one, aniline and N-methyl-maleimide.

EXAMPLE AH (3'aR,6'aS)-5'-methyl-2'-phenyl-1-(R)-1-phenyl-ethyl]-hexahydro-spiro[piperidine-4,1'-pyrrolo[3,4-c]pyrrole]-4',6'-dione The title compound, white foam $[\alpha]_D^{20}$=+104.70 (c=0.2751 in CHCl$_3$) and MS: m/e=404.5 (M+H$^+$) was prepared in accordance with the general method of example 5 from (R)-1-(1-phenyl-ethyl)-piperidin-4-one, aniline and N-methyl-maleimide.

EXAMPLE AI (3'aS,6'aR)-5'-Methyl-2'-phenyl-hexahydro-spiro1piperidine-4,1'-pyrrolo[3,4-c]pyrrole]-4',6'-dione The title compound, white solid, m.p. 159° C.; $[\alpha]_D^{20}$=−124.00 (c=0.2862 in CHCl$_3$) and MS: m/e=300.3 (M+H$^+$) was prepared by hydrogenation of (3'aS,6'aR)-5'-methyl-2'-phenyl-1-[(R)-1-phenyl-ethyl]-hexahydro-spiro[piperidine-4,1'-pyrrolo[3,4-c]pyrrole]-4',6'-dione in accordance with the general method of example 106.

EXAMPLE AJ (3'aR,6'aS)-5'-Methyl-2'-phenyl-hexahydro-spiro[piperine-4,1'-pyrrolo[3,4-c]pyrrole]-4',6'-dione The title compound, white solid, m.p. 160° C. ; $[\alpha]_D^{20}$=+117.00 (c=0.2862 in CHCl$_3$ and MS: m/e=300.3 (M+H$^+$) was prepared by hydrogenation of (3'aR,6'aS)-5'-methyl-2'-phenyl-1-[(R)-1-phenyl-ethyl]-hexahydro-spiro[piperidine-4,1'-pyrrolo[3,4-c]pyrrole]-4',6'-dione in accordance with the general method of example 106.

EXAMPLE AK (3'aRS,6'aSR)-5'-Ethyl-2'-phenyl-hexahydro-spiro[piperidine-4,1'-pyrrolo[3,4-c]pyrrole]fumarate (1:1.4)

The title compound, m.p.>190° C. dec. and MS: m/e=286.2 (M+H$^+$) was prepared in accordance with the general method of example 15 from (3'aRS,6'aSR)-5'-ethyl-2!-phenyl-hexahydro-spiro[piperidine-4,1'(2'H)-pyrrolo[3,4-c]pyrrole]-4',6'-dione.

EXAMPLE AL (4-Fluoro-phenyl)-[1-(cis-4-isopropyl-cyclohexyl)-piperidin-4-ylidene]-amine cis-1-(4-Isopropyl-cyclohexyl)-piperidine-4-on (5.0 g, 23.4 mmol), 4-fluoro aniline (3.3 g, 35.3 mmol) and molecular sieves (20 g, 4A) were stirred in 100 ml pentane at room temperature for 6 days. The molecular sieves was filtered off and the solvent was evaporated. The crude product was used without any further purification for the following step.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

We claim:

1. A compound of formula I

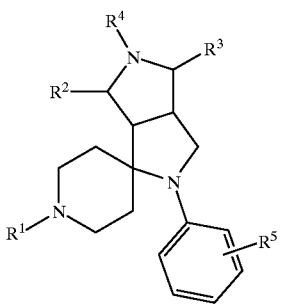

I wherein
- $R^1$ is $C_{5-12}$-cycloalkyl, optionally substituted by lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; bicyclo[3.3.1]non-9-yl; 2,3-dihydro-1H-phenalen-1-yl; 2,3,3a,4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;
- $R^2$, $R^3$ are hydrogen; hydroxy; lower alkyl; =O; or phenyl, which is unsubstituted or substituted by lower alkyl, halogen or alkoxy;
- $R^4$ is hydrogen; lower alkyl; —(CH)$_n$CH(OH)CF$_3$; —(CH$_2$)$_n$C$_{3-6}$-cycloalkyl; phenyl; benzyl; tetrahydrofuran-3-yl; —(CH$_2$)$_n$OCH$_2$C$_6$H$_5$; —(CH$_2$)$_n$ morpholinyl; 3-methyl-oxetan-3-yl-methyl; —(CH$_2$)$_n$CH$_2$OH; —S(O)$_2$-lower alkyl; —C(O)-lower alkyl; —C(O)CF$_3$; —C(O)(CH$_2$)$_n$OCH$_3$; —(CH$_2$)$_n$C(O)N(lower alkyl)$_2$; —S(O)$_2$heteroaryl; —C(O)heteroaryl; —S(O)$_2$-phenyl; —S(O)$_2$—N(lower alkyl)$_2$; —C(O)—C$_{3-6}$-cycloalkyl; —C(O)O-phenyl; or —C(O)O-lower alkyl:
- $R^5$ is hydrogen; halogen; lower alkyl; trifluoromethyl or lower alkoxy;
- n is 0–3;

racemic mixtures and their corresponding enantiomers and pharmaceutically acceptable acid addition salts thereof.

2. A compound according to claim 1, in which $R^1$ is $C_{5-12}$-cycloalkyl, which is unsubstituted or substituted by lower alkyl.

3. A compound according to claim 2, (3'aRS,6'aSR)-1-cyclononyl-5'-methyl-2'-phenyl-hexahydro-spiro[piperidine-4,1'(2'H)-pyrrolo[3,4-c]pyrrolo].

4. A compound according to claim 2, (3'aRS,6'aSR)-1-cyclodecyl-5'-methyl-2'-phenyl-hexahydro-spiro[piperidine-4,1'(2'H)-pyrrolo[3,4-c]pyrrol]-4',6'-dione.

5. A compound according to claim 2, (3'aRS,6'aSR)-1-cyclodecyl-5'-ethyl-2'-phenyl-hexahydro-spiro[piperidine-4,1'(2'H)-pyrrolo[3,4-c]pyrrole].

6. A compound according to claim 2, (3'aRS,6'aSR)1-(cis-4-isopropyl-cyclohexyl)-5'-methyl-2'-phenyl-hexahydro-spiro[piperidine-4,1'-pyrrolo[3,4-c]pyrrolo].

7. A compound according to claim 2, (3'aRS,6'aSR)1-(cis-4-isopropyl-cyclohexyl)-5'-ethyl-2'-phenyl-hexahydro-spiro[piperidine-4,1'-pyrrolo[3,4-c]pyrrole].

8. A compound according to claim 2, (3'aRS,6'aSR)-4-(cis-4-isopropyl-cyclohexyl)-5'-butyl-2'-phenyl-hexahydro-spiro[piperidine-4,1'(2'H)-pyrrolo[3,4-c]pyrrolo].

9. A compound according to claim 2, (3'aRS,6'aSR)-4-(cis-4-isopropyl-cyclohexyl)-5'-cyclopropylmethyl-2'-phenyl-hexahydro-spiro[piperidine-4,1'(2'H)-pyrrolo[3,4-c]pyrrolo].

10. A compound according to claim 2, (3'aRS,4'SR,6'aRS)-1-(cis-4-isopropyl-cyclohexyl)-4',5'-dimethyl-2'-phenyl-hexahydro-spiro[piperidine-4,1'-pyrrolo[3,4-c]pyrrolo].

11. A compound according to claim 2, (3'aRS,6'aSR)-4-(cis-4isopropyl-cyclohexyl)-2'-phenyl-hexahydro-spiro[piperidine-4,1'(2'H)-pyrrolo[3,4-c]pyrrole].

12. A compound according to claim 2, (3'aRS,6'aSR)-1-cyclodecyl-5'-methyl-2'-phenyl-hexahydro-spiro[piperidine-4,1'(2'H)-pyrrolo[3,4-c]pyrrolo].

13. A compound according to claim 2, (3'aRS,6'aSR)-1-cyclononyl-5'-ethyl-2'-phenyl-hexahydro-spiro[piperidine-4,1'(2'H)-pyrrolo[3,4-c]pyrrole].

14. A compound according to claim 2, (3'aRS,6'aSR)-1-(cis-4-isopropyl-cyclohexyl)-5'-methyl-2'-phenyl-hexahydro-spiro[piperidine, 1'-pyrrolo[3,4-c]pyrrole]-4',6'-dione.

15. A compound according to claim 2, (3'aRS,6'aSR)-1-(cis-4-isopropyl-cyclohexyl)-5'-benzyl-2'-phenyl-hexahydro-spiro[piperidine-4,1'-pyrrolo[3,4-c]pyrrol e-4',6'dione.

16. A compound according to claim 2, (3'aRS,6'aSR)-4-(cis-4-isopropyl-cyclohexyl)-5'-benzyl-2'-phenyl-hexahydro-spiro[piperidine-4,1'(2'H)-pyrrolo[3,4-c]pyrrole].

17. A compound according to claim 2, (3'aRS,6'aSR)-4-(cis-4-isopropyl-cyclohexyl)-5'-cyclohexyl-2'-phenyl-hexahydro-spiro[piperidine-4,1'(2'H)-pyrrolo[3,4-c]pyrrole].

18. A compound according to claim 2, (3'aS,6'aR)1-(cis-4isopropyl-cyclohexyl)-5'-methyl-2'-phenyl-hexahydro-spiro[piperidine-4,1'-pyrrolo[3,4-c]pyrrole].

19. A compound according to claim 2, (3'aR,6'aS)1-(cis-4-isopropyl-cyclohexyl)-5'-methyl-2'-phenyl-hexahydro-spiro[piperidine-4,1'-pyrrolo[3,4-c]pyrrole].

20. A compound according to claim 2, (3'aRS,6'aRS)-1-(cis-4-isopropyl-cyclohexyl)-5'-(2-hydroxy-ethyl)-2'-phenyl-hexahydro-spiro[piperidine-4,1'-pyrrolo[3,4-c]pyrrole].

21. A compound according to claim 2, (3'aRS,6'aSR)-2-[1-(cis-4-isopropyl-cyclohexyl)-2'-phenyl-hexahydro-spiro[piperidine-4,1'-pyrrolo[3,4-c]pyrrol]-5'-yl]-N,N-dimethyl-acetamide.

22. A compound according to claim 2, (3'aRS,6'aRS)-[1-(cis-4-isopropyl-cyclohexyl)-2'-phenyl-hexahydro-spiro[piperidine-4,1'-pyrrolo[3,4-c]pyrrol]-5'-yl]-pyridin-3-yl-methanone.

23. A compound according to claim 2, (3'aRS,6'aSR)-2'-(3-fluoro-phenyl)-1-(cis-4-isopropyl-cyclohexyl)-5'-methyl-hexahydro-spiro[piperidine-4,1'-pyrrolo[3,4-c]pyrrole]-4',6'-dione.

24. A compound according to claim 2, (3'aS,6'aR)-1-cyclononyl-5'-methyl-2'-phenyl-hexahydro-spiro[piperidine-4,1'-pyrrolo[3,4-c]pyrrole].

25. A compound according to claim 2, (3'aS,6'aR)-1-cyclodecyl-2'-(2-fluoro-phenyl)-5-methyl-hexahydro-spiro[piperidine-4,1'-pyrrolo[3,4-c]pyrrole].

26. A compound according to claim 2, (3'aRS,6'aSR)-1-cyclononyl-2'-(4-fluoro-phenyl)-5'-methyl-hexahydro-spiro[piperidine-4,1'-pyrrolo[3,4-c]pyrrole].

27. A compound according to claim 2, (3'aRS,6'aSR)-1-cyclononyl-2'-phenyl-hexahydro-spiro[piperidine-4,1'-pyrrolo[3,4-c]pyrrole].

28. A compound according to claim 2, (3'aRS,6'aSR)-(1-cyclononyl-2'-phenyl-hexahydro-spiro[piperine-4,1'-pyrrolo[3,4-c]pyrrol]-5'-yl)-cyclopropyl-methanone.

29. A compound according to claim 2, (3'aRS,6'aRS)-1-(cis-4-isopropyl-cyclohexyl)-2'-phenyl-hexahydro-spiro[piperidine-4,1'-pyrrolo[3,4-copyrrol]-5'-yl]-thiophen-2-yl-methanone.

30. A compound according to claim 2, (3'aRS,6'aSR)-(1-cyclodecyl-2'-phenyl-hexahydro-spiro[piperine-4,1'-pyrrolo[3,4-c]pyrrol]-5'-yl)-cyclopropyl-methanone.

31. A compound according to claim 1, wherein $R^1$ is decahydro-naphthalen-2-yl.

32. A compound according to claim 31, which is a mixture of (3'aSR,6'aRS)- and (3'aRS,6'aSR)-1-[(2RS,4aSR,8aRS)-decahydro-naphthalen-2-yl]-5'-methyl-2'-phenyl-hexahydro-spiro[piperidine-4,1'-pyrrolo[3,4-c]pyrrole].

33. A compound according to claim 31, which is a mixture of (3'aSR,6'aRS)- and (3'aRS,6'aSR)-1-1(2RS,4aSR,8aRS)-decahydro-naphthalen-2-yl]-2'-phenyl-hexahydro-spiro[piperidine-4,1'-pyrrolo[3,4-c]pyrrole].

34. A compound according to claim 31, which is a mixture of (3'aSR,6'aRS)- and (3'aRS,6'aSR)-5'-ethyl-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione.

35. A compound according to claim 31, which is a mixture of (3'aSR,6'aRS)- and (3'aRS,6'aSR)-5'-methyl-1-[(2RS,4aSR,8aRS)-decahydro-naphthalen-2-yl]-2'-phenyl-hexahydro-spiro[piperidine-4,1'-pyrrolol3,4-c]pyrrole]-4',6'-dione.

36. A compound according to claim 31, which is a mixture of (3'aSR,6'aRS)- and (3'aRS,6'aSR)-1-[(2RS,4aSR,8aRS)-decahydro-naphthalen-2-yl]-2'-phenyl-hexahydro-spiro[piperidine-4,1'-pyrrolo[3,4-c]pyrrole]-4',6'-dione.

37. A compound according to claim 31, which is a mixture of (3'aSR,6'aRS)- and (3'aRS,6'aSR)-5'-ethyl-1-[(2RS,4aSR,8aRS)-decahydro-naphthalen-2-yl]-2'-phenyl-hexahydro-spiro[piperidine-4,1'-pyrrolo[3,4-c]pyrrole].

38. A compound according to claim 1, which is a mixture of (3'aRS,6'aSR)- and (3'aSR,6'aRS)-5'-methyl-1-[(RS)-methyl-indan-2-yl]-2'-phenyl-hexahydro-spiro[piperidine-4,1'-pyrrolo[3,4-c]pyrrole].

39. A compound according to claim 1, which is a mixture of (3'aRS,6'aSR)- and (3'aSR,6'aRS)-1-[(RS)-4-methyl-indan-2-yl]-2'-phenyl-hexahydro-spiro[piperidine-4,1'-pyrrolo[3,4-c]pyrrole].

40. A compound according to claim 1, (3'aS,6'aR)-5'-ethyl-2'-phenyl-1-[(R)-1,2,3,4-tetrahydro-naphtalen-1-yl]-hexahydro-spiro[piperidine-4,1'-pyrrolo[3,4-c]pyrrole].

41. A compound according to claim 1, (3'aS,6'aR)-5'-methyl-2'-phenyl-1-[(R)-1,2,3,4-tetrahydro-naphtalen-1-yl]-hexahydro-spiro[piperidine-4,1'-pyrrolo[3,4-c]pyrrole].

42. A compound according to claim 1, (3'aSR,6'aRS)-1-[(RS)-acenaphthen-1-yl]-5'-methyl-1'-phenyl-hexahydro-spiro[piperidine-4,1'(2'H)-pyrrolo[3,4-c]pyrrole].

43. A compound according to claim 1, (3'aRS,6'aSR)-1-[(1 RS,3aRS)-2,3,3a,4,5,6-hexahydro-1H-phenalen-1-yl]-5'-methyl-2'-phenyl-hexahydro-spiro[piperidine-4,1'(2'H)-pyrrolo[3,4-c]pyrrole].

44. A compound according to claim 1, which is a mixture of (3'aRS,6'aSR)- and (3'aSR,6'aRS)-1-[(RS)-2,3-dihydro-1H-phenalen-1-yl]-5'-methyl-2'-phenyl-hexahydro-spiro[piperidine-4,1'(2'H)-pyrrolo[3,4-c]pyrrole.

45. A process for preparing a compound of formula I as defined in claim 1, comprising reductively animating a compound of formula II

II with a compound of formula III

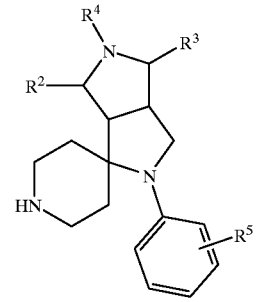

III wherein:
$R^1$ is $C_{5-12}$-cycloalkyl, optionally substituted by lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; bicyclo[3.3.1]non-9-yl; 2,3-dihydro-1H-phenalen-1-yl; 2,3,3a,4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;

$R^2$, $R^3$ are hydrogen; hydroxy; lower alkyl; =O; or phenyl, which is unsubstituted or substituted by lower alkyl, halogen or alkoxy;

$R^4$ is hydrogen; lower alkyl; —(CH)$_n$CH(OH)CF$_3$; —(CH$_2$)$_n$C$_{3-6}$-cycloalkyl; phenyl; benzyl; tetrahydrofuran-3-yl; —(CH$_2$)$_n$OCH$_2$C$_6$H$_5$; —(CH$_2$)$_n$morpholinyl; 3-methyl-oxetan-3-yl-methyl; —(CH$_2$)$_n$CH$_2$OH; —S(O)$_2$-lower alkyl; —C(O)-lower alkyl; —C(O)CF$_3$; —C(O)(CH$_2$)$_n$OCH$_3$; —(CH$_2$)$_n$C(O)N(lower alkyl)$_2$; —S(O)$_2$ heteroaryl; —C(O)heteroaryl; —S(O)$_2$-phenyl; —S(O)$_2$—N(lower alkyl)$_2$; —C(O)—C$_{3-6}$-cycloalkyl; —C(O)O-phenyl; or —C(O)O-lower alkyl:

$R^5$ is hydrogen; halogen; lower alkyl; trifluoromethyl or lower alkoxy;

n is 0–3.

46. A process for preparing a compound of formula I as defined in claim 1, comprising reducing a compound of formula I-1

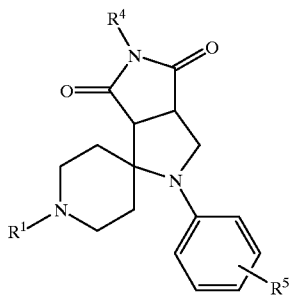

to a compound of one of the formulae

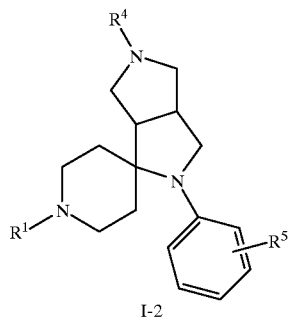

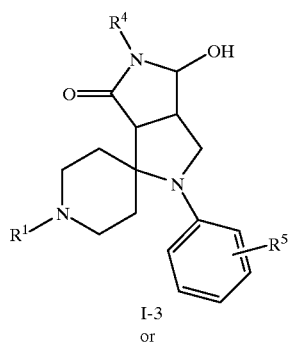

or

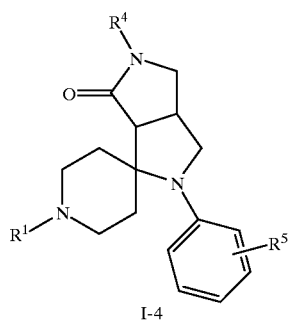

wherein

R¹ is $C_{5-12}$-cycloalkyl, optionally substituted by lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; bicyclo[3.3.1]non-9-yl; 2,3-dihydro-1H-phenalen-1-yl; 2,3,3a,4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;

R⁴ is hydrogen; lower alkyl; —(CH)$_n$CH(OH)CF₃; —(CH₂)$_n$C$_{3-6}$-cycloalkyl; phenyl; benzyl; tetrahydrofuran-3-yl; —(CH₂)$_n$OCH₂C₆H₅; —(CH₂)$_n$morpholinyl; 3-methyl-oxetan-3-yl-methyl; —(CH₂)$_n$CH₂OH; —S(O)₂-lower alkyl; —C(O)-lower alkyl; —C(O)CF₃; —C(O)(CH₂)$_n$OCH₃; —(CH₂)$_n$C(O)N(lower alkyl)₂; —S(O)₂ heteroaryl; —C(O)heteroaryl; —S(O)₂-phenyl; —S(O)₂—N(lower alkyl)₂; —C(O)-C$_{3-6}$-cycloalkyl; —C(O)O-phenyl; or —C(O)O-lower alkyl:

R⁵ is hydrogen; halogen; lower alkyl; trifluoromethyl or lower alkoxy;

n is 0–3.

47. A process for preparing a compound of formula I as defined in claim 1, comprising acylating or sulfonylating a compound of formula I-5

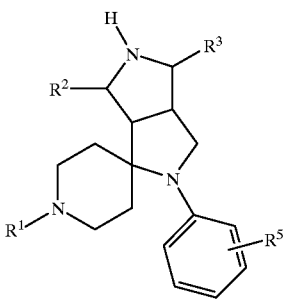

to a compound of formula

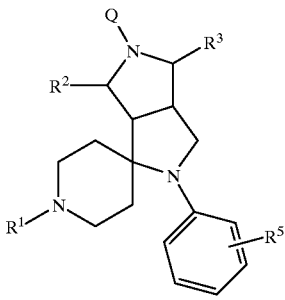

wherein

R¹ is $C_{5-12}$-cycloalkyl, optionally substituted by lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; bicyclo[3.3.1]non-9-yl; 2,3-dihydro-1H-phenalen-1-yl; 2,3,3a,4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;

R², R³ are hydrogen; hydroxy; lower alkyl; =O; or phenyl, which is unsubstituted or substituted by lower alkyl, halogen or alkoxy;

R[5] is hydrogen; halogen; lower alkyl; trifluoromethyl or lower alkoxy;

Q is —S(O)$_2$-lower alkyl; —C(O)CF$_3$; —C(O)(CH$_2$)$_n$OCH$_3$; —(CO)N(lower alkyl)$_2$; —S(O)$_2$-heteroaryl; —C(O)-heteroaryl; —S(O)$_2$-phenyl; —C(O)-C$_{3-6}$— cycloalkyl; or —C(O)O-lower alkyl; and n is 0–3.

48. A process for preparing a compound of formula I as defined in claim 1, comprising debenzylating a compound of formula I-7

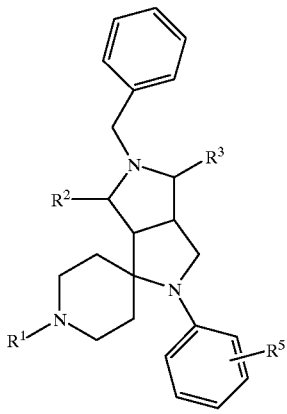

I-7 to a compound of formula

I-5

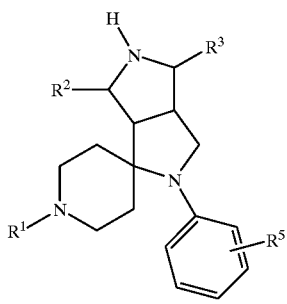

wherein

R[1] is C$_{5-12}$-cycloalkyl, optionally substituted by lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; bicyclo[3.3.1]non-9-yl; 2,3-dihydro-1H-phenalen-1-yl; 2,3,3a,4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;

R[2], R[3] are hydrogen; lower alkyl; or phenyl, which is unsubstituted or substituted by lower alkyl, halogen or alkoxy;

R[5] is hydrogen; halogen; lower alkyl; trifluoromethyl or lower alkoxy; and n is 0–3.

49. A process for preparing a compound of formula I as defined in claim 1, comprising reacting a ketone of formula VI

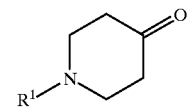

VI with N-phenyl-glycine of formula

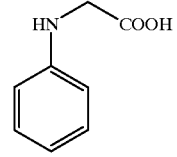

and trapping the forming azomethine-ylides of formula

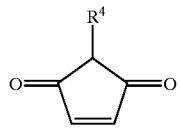

in a compound of formula I-1

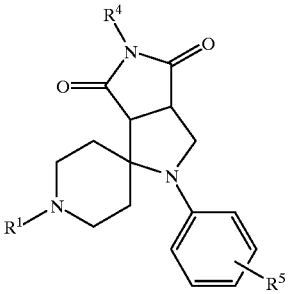

I-1 wherein

R[1] is C$_{5-12}$-cycloalkyl, optionally substituted by lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; bicyclo[3.3.1]non-9-yl; 2,3-dihydro-1H-phenalen-1-yl; 2,3,3a,4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;

R[4] is hydrogen; lower alkyl; —(CH$_2$)$_n$CH(OH)CF$_3$; —(CH$_2$)$_n$C$_{3-6}$-cycloalkyl; phenyl; benzyl; tetrahydrofuran-3-yl; —(CH$_2$)$_n$OCH$_2$C$_6$H$_5$; —(CH$_2$)$_n$morpholinyl; 3-methyl-oxetan-3-yl-methyl; —(CH$_2$)$_n$CH$_2$OH; —S(O)$_2$-lower alkyl; —C(O)-lower alkyl; —C(O)CF$_3$; —C(O)(CH$_2$)$_n$OCH$_3$; —(CH$_2$)$_n$C(O)N(lower alkyl)$_2$; —S(O)$_2$ heteroaryl; —C(O)heteroaryl; —S(O)$_2$-phenyl; —S(O)$_2$—N(lower alkyl)$_2$; —C(O)-C$_{3-6}$-cycloalkyl; —C(O)O-phenyl; or —C(O)O-lower alkyl:

R[5] is hydrogen; halogen; lower alkyl; trifluoromethyl or lower alkoxy;

n is 0–3.

50. The process according to claim 49 further comprising converting a racemic mixture into its enantiomeric components thus obtaining substantially optically pure compounds.

51. The process according to claim 49 further comprising converting a compound of formula I obtained into a pharmaceutically acceptable acid addition salt.

52. A pharmaceutical composition comprising a therapeutically effective amount of a compound of the formula I

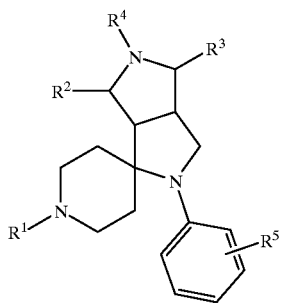

I wherein
$R^1$ is $C_{5-12}$-cycloalkyl, optionally substituted by lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; bicyclo[3.3.1]non-9-yl; 2,3-dihydro-1H-phenalen-1-yl; 2,3,3a,4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;

$R^2$, $R^3$ are hydrogen; hydroxy; lower alkyl; =O; or phenyl, which is unsubstituted or substituted by lower alkyl, halogen or alkoxy;

$R^4$ is hydrogen; lower alkyl; —$(CH_2)_n CH(OH)CF_3$; —$(CH_2)_n C_{3-6}$-cycloalkyl; phenyl; benzyl; tetrahydrofuran-3-yl; —$(CH_2)_n OCH_2C_6H_5$; —$(CH_2)_n$morpholinyl; 3-methyl-oxetan-3-yl-methyl; —$(CH_2)_n CH_2OH$; —$S(O)_2$-lower alkyl; —C(O)-lower alkyl; —$C(O)CF_3$; —$C(O)(CH_2)_n OCH_3$; —$(CH_2)_n C(O)N(\text{lower alkyl})_2$; —$S(O)_2$ heteroaryl; —C(O)heteroaryl; —$S(O)_2$-phenyl; —$S(O)_2$—N(lower alkyl)$_2$; —C(O)-$C_{3-6}$-cycloalkyl; —C(O)O-phenyl; or —C(O)O-lower alkyl:

$R^5$ is hydrogen; halogen; lower alkyl; trifluoromethyl or lower alkoxy;

n is 0–3;

as well as pharmaceutically acceptable salts thereof and a pharmaceutically acceptable carrier.

53. A method of treating diseases in a mammal related to the orphanin FQ receptor comprising administering to said mammal a compound of the formula I

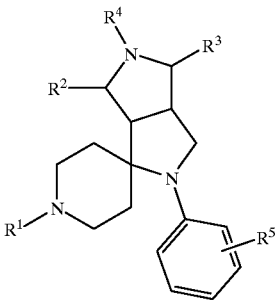

I wherein
$R^1$ is $C_{5-12}$-cycloalkyl, optionally substituted by lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; bicyclo[3.3.1]non-9-yl; 2,3-dihydro-1H-phenalen-1-yl; 2,3,3a,4,5,6-hexahydro-1H-phenalen-1-yl; octahydro-inden-2-yl; 1,2,3,4-tetrahydro-naphthalen-1-yl; 1,2,3,4-tetrahydro-naphthalen-2-yl; naphthalen-lower alkyl-1-yl; naphthalen-lower alkyl-2-yl; acenaphthen-1-yl; and 5-isopropyl-2-methyl-bicyclo[3.1.0]hex-3-yl;

$R^2$, $R^3$ are hydrogen; hydroxy; lower alkyl; =O; or phenyl, which is unsubstituted or substituted by lower alkyl, halogen or alkoxy;

$R^4$ is hydrogen; lower alkyl; —$(CH_2)_n CH(OH)CF_3$; —$(CH_2)_n C_{3-6}$-cycloalkyl; phenyl; benzyl; tetrahydrofuran-3-yl; —$(CH_2)_n OCH_2C_6H_5$; —$(CH_2)_n$morpholinyl; 3-methyl-oxetan-3-yl-methyl; —$(CH_2)_n CH_2OH$; —$S(O)_2$-lower alkyl; —C(O)-lower alkyl; —$C(O)CF_3$; —$C(O)(CH_2)_n OCH_3$; —$(CH_2)_n C(O)N(\text{lower alkyl})_2$; —$S(O)_2$ heteroaryl; —C(O)heteroaryl; —$S(O)_2$-phenyl; —$S(O)_2$—N(lower alkyl)$_2$; —C(O)-$C_{3-6}$-cycloalkyl; —C(O)O-phenyl; or —C(O)O-lower alkyl:

$R^5$ is hydrogen; halogen; lower alkyl; trifluoromethyl or lower alkoxy;

n is 0–3;

as well as pharmaceutically acceptable salts thereof and a pharmaceutically acceptable carrier in an amount which is effective for treating said disease.

* * * * *

UNITED STATES PATENT AND TRADEMARK OFFICE
CERTIFICATE OF CORRECTION

PATENT NO. : 6,075,034
DATED : June 13, 2000
INVENTOR(S) : Geo Adam et al.

It is certified that error appears in the above-indentified patent and that said Letters Patent is hereby corrected as shown below:

In claim 1, column 95, line 50, replace "(CH)" with -- $(CH_2)$ --.

In claim 3, column 96, line 2, replace "2 –phenyl" with -- 2'-phenyl --.

In claim 3, column 96, line 3, replace "pyrrolo", second instance, with -- pyrrole --.

In claim 4, column 96, line 6, replace "pyrrol" with -- pyrrole --.

In claim 6, column 96, line 12, replace "pyrrolo", second instance, with -- pyrrole --.

In claim 8, column 96, line 17, replace "pyrrolo", second instance, with -- pyrrole --.

In claim 9, column 96, line 21, replace "pyrrolo", second instance, with -- pyrrole --.

UNITED STATES PATENT AND TRADEMARK OFFICE
CERTIFICATE OF CORRECTION

PATENT NO.  : 6,075,034
DATED       : June 13, 2000
INVENTOR(S) : Geo Adam et al.

It is certified that error appears in the above-indentified patent and that said Letters Patent is hereby corrected as shown below:

In claim 10, column 96, line 25, replace "pyrrolo", second instance, with -- pyrrole --.

In claim 14, column 96, line 36, after "piperidine", insert -- -4, --.

In claim 18, column 96, line 51, replace "isopropyl" with -- "4-isopropyl--.

In claim 25, column 97, replace "5-methyl" with -- 5'-methyl --.

In claim 29, column 97, line 22, replace "[3,4-copyrrol]" with -- [3,4-c]pyrrol] --.

UNITED STATES PATENT AND TRADEMARK OFFICE
CERTIFICATE OF CORRECTION

PATENT NO. : 6,075,034
DATED : June 13, 2000
INVENTOR(S) : Geo Adam et al

It is certified that error appears in the above-indentified patent and that said Letters Patent is hereby corrected as shown below:

In claim 35, column 97, line 44, replace "pyrrolo1" with -- pyrrolo[ --.

In claim 38, column 97, line 56, at beginning of sentence insert  -- 4- -- in front of "methyl".

In claim 47, column 101, line 3, after "alkyl:" insert  -- -C(O)-lower alkyl; --.

In claim 47, column 101, line 4, replace " (CO)" with  -- C(O) --.

Signed and Sealed this

Seventeenth Day of April, 2001

*Attest:*

NICHOLAS P. GODICI

*Attesting Officer*   Acting Director of the United States Patent and Trademark Office